United States Patent
Serra Pagès et al.

(10) Patent No.: US 10,927,416 B2
(45) Date of Patent: Feb. 23, 2021

(54) METHOD FOR DIAGNOSING COLORECTAL CANCER FROM A HUMAN FECES SAMPLE BY QUANTITATIVE PCR, PRIMERS AND KIT

(71) Applicants: FUNDACIÓ INSTITUT D'INVESTIGACIÓ BIOMÈDICA DE GIRONA DR. JOSEP TRUETA, Salt (ES); UNIVERSITAT DE GIRONA, Girona (ES)

(72) Inventors: Mariona Serra Pagès, Figueres Girona (ES); Librado Jesús García-Gil, Fontcoberta Girona (ES); Teresa Mas De Xaxars, Fontcoberta Girona (ES); Xavier Aldeguer Manté, Girona (ES)

(*) Notice: Subject to any disclaimer, the term of this patent is extended or adjusted under 35 U.S.C. 154(b) by 313 days.

(21) Appl. No.: 15/122,897

(22) PCT Filed: Mar. 3, 2015

(86) PCT No.: PCT/EP2015/054451
§ 371 (c)(1),
(2) Date: Aug. 31, 2016

(87) PCT Pub. No.: WO2015/132273
PCT Pub. Date: Sep. 11, 2015

(65) Prior Publication Data
US 2017/0096709 A1 Apr. 6, 2017

(30) Foreign Application Priority Data
Mar. 3, 2014 (EP) .................... 14382074

(51) Int. Cl.
*C12Q 1/6886* (2018.01)
*C12Q 1/689* (2018.01)

(52) U.S. Cl.
CPC .......... *C12Q 1/6886* (2013.01); *C12Q 1/689* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 6,054,278 A | 4/2000 | Dodge et al. | |
|---|---|---|---|
| 2016/0000838 A1* | 1/2016 | Harmsen | A61K 35/74 424/93.3 |
| 2016/0032363 A1* | 2/2016 | Stintzi | C12Q 1/04 514/503 |

FOREIGN PATENT DOCUMENTS

| WO | WO-01/23608 A2 | 4/2001 |
|---|---|---|
| WO | WO-01/23608 A3 | 4/2001 |
| WO | WO-2009/057695 A1 | 5/2009 |
| WO | WO-2010/010914 A1 | 1/2010 |
| WO | WO-2012/170478 A2 | 12/2012 |
| WO | WO-2012/170478 A3 | 12/2012 |

OTHER PUBLICATIONS

Lucentini, "Gene Association Studies Typically Wrong", The Scientist, Dec. 20, vol. 18, issue 24, print out pp. 1-4. (Year: 2004).*
Ioannidis et al., "Replication validity of genetic association studies," Nature Genetics, Oct. 15, vol. 29, pp. 306-309. (Year: 2001).*
Wacholder et al., "Assessing the Probability That a Positive Report is False: An Approach for Molecular Epidemiology Studies," Journal of the National Cancer Institute, Mar. 17, vol. 96, No. 6, pp. 434-442. (Year: 2004).*
Sobhani et al., "Microbial Dysbiosis in Colorectal Cancer (CRC) Patients," PLoS One, Jan. 27, vol. 6, No. 1, e16393, pp. 1-7. (Year: 2011).*
GenBank Accession No. MN904971 [retrieved on-line from: https://www.ncbi.nlm.nih.gov/nucleotide/MN904971; retrieval date Mar. 4, 2020] (Year: 2020).*
Brim, H. et al. (Dec. 20, 2013). "Microbiome analysis of stool samples from African Americans with colon polyps," *PLoS One* 8(12):e81352.
Chen, W. et al. (2012, e-published Jun. 28, 2012). "Human intestinal lumen and mucosa-associated microbiota in patients with colorectal cancer," *PLoS One* 7(6):e39743.
Database Accession No. BD423679, "Single nucleotide polymorphism in a human gene encoding receptor protein," created Nov. 9, 2005, 1 page.
Database Accession No. GQ411111, Uncultured bacterium isolate DGGE gel band Eub_316S ribosomal RNA gene, partial sequence, created Sep. 3, 2009, 1 page.
Database Accession No. GQ411118, Uncultured bacterium isolate DGGE gel band Eub_1016S ribosomal RNA gene, partial sequence, created Sep. 3, 2009, 1 page.
Database Accession No. GQ411150, Uncultured bacterium isolate DGGE gel band Eub_4616S ribosomal RNA gene, partial sequence, created Sep. 3, 2009, 1 page.
Database Accession No. GQ411152, Uncultured bacterium isolate DGGE gel band Eub_4816S ribosomal RNA gene, partial sequence, created Sep. 3, 2009, 1 page.
Lepage, P. et al. (May 1, 2005). "Biodiversity of the mucosa-associated microbiota is stable along the distal digestive tract in healthy individuals and patients with IBD," *Inflamm Bowel Dis* 11(5):473-480.
Teresa Mas De Xaxars Rivero (Feb. 10, 2012). "Descripcio i quantificacio de la microbiota intestinal associada al cancer colorectal," 239 pages.

(Continued)

*Primary Examiner* — Young J Kim
(74) *Attorney, Agent, or Firm* — Mintz Levin Cohn Ferris Glovsky and Popeo PC; Terri Shieh-Newton; David Dang

(57) ABSTRACT

The present invention relates to the field of detection of colorectal cancer (CRC). Specifically it relates to methods for the early detection, risk screening and monitoring of CRC and/or adenomatous polyps in a human subject based on the quantification of one or more 16S rDNA bacterial sequences in feces. It further relates to the use of said bacterial sequences as biomarkers of colorectal cancer and/or adenomatous polyps; to a kit comprising a reagent and instructions for the quantification of said bacterial sequences; and to nucleic acids for the quantification of said 16S rDNA bacterial sequences.

30 Claims, 27 Drawing Sheets

Specification includes a Sequence Listing.

(56) References Cited

OTHER PUBLICATIONS

Wu, N. et al. (Aug. 2013, e-published Jun. 4, 2013). "Dysbiosis signature of fecal microbiota in colorectal cancer patients," *Microb Ecol* 66(2):462-470.
International Search Report dated May 19, 2015, for PCT Application No. PCT/EP2015/054451, filed Mar. 3, 2015, 7 pages.
Written Opinion dated May 19, 2015, for PCT Application No. PCT/EP2015/054451, filed Mar. 3, 2015, 9 pages.
Russian Search Report dated Jan. 29, 2018, for Russian Application No. 2016138766/10(061779), 4 pages.
Digestive Disease Characteristic Diagnosis and Treatment Technology, Jan. 2004, 2 pages.

\* cited by examiner

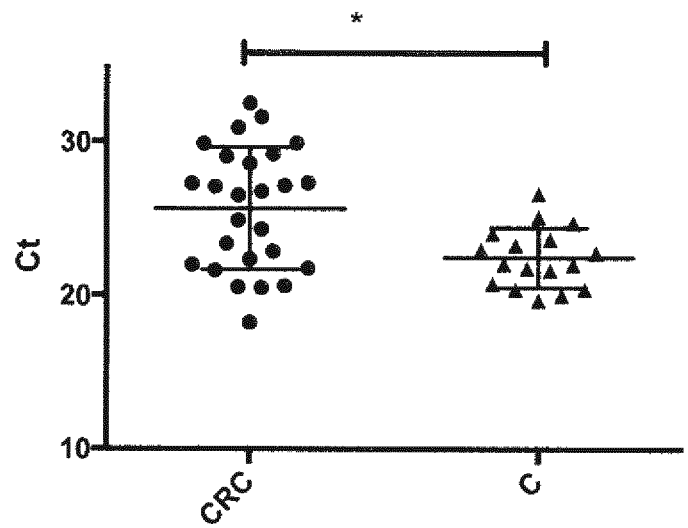
Figure 14. Ct value of B3 in CRC and C groups.
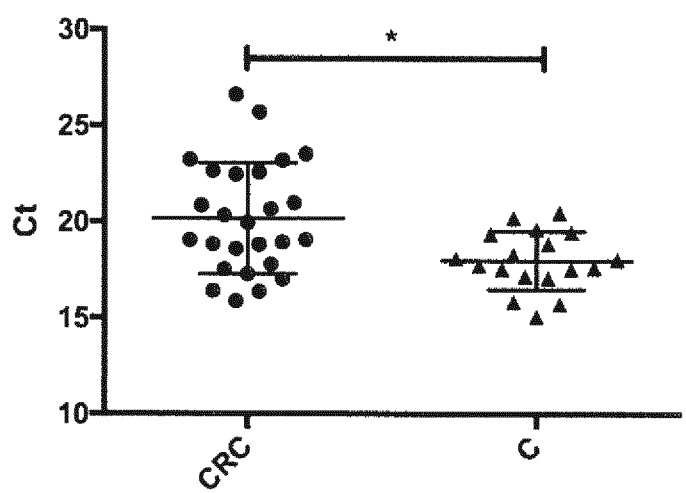
Figure 15. Ct value of B48 in CRC and C groups.

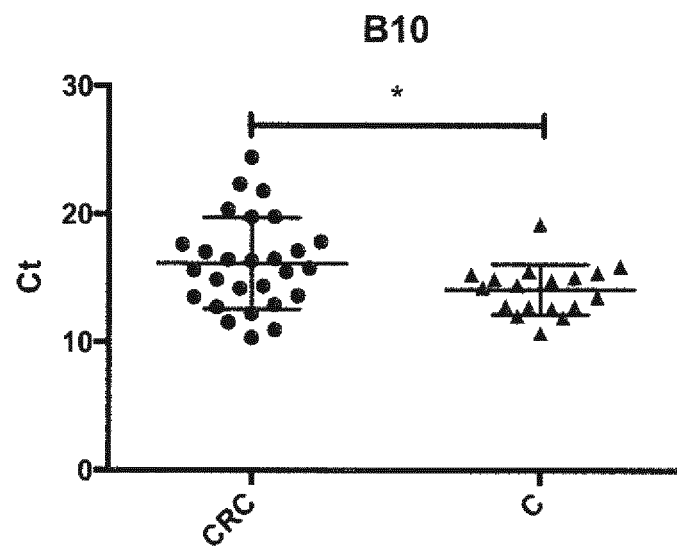
Figure 16. Ct value of B10 in CRC and C groups.
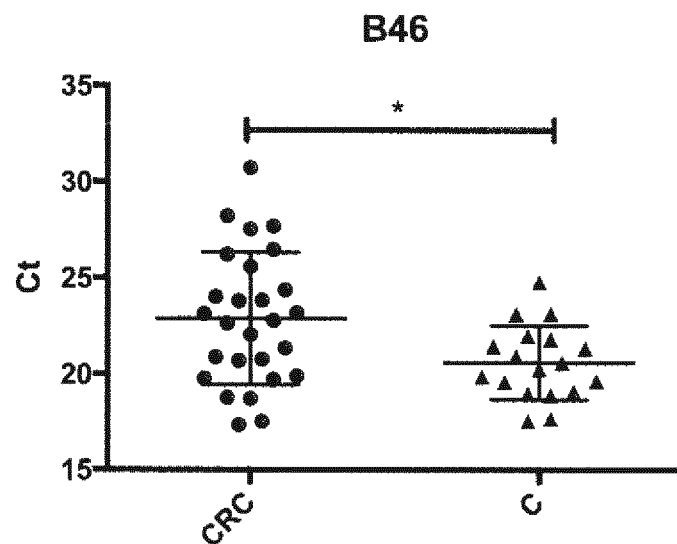
Figure 17. Ct value of B46 in CRC and C groups.

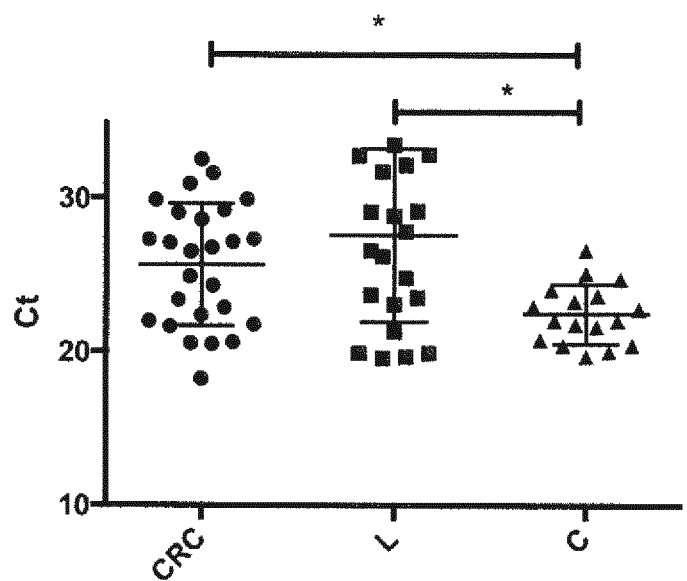
Figure 18. Ct value of B3 in CRC, L and C groups.
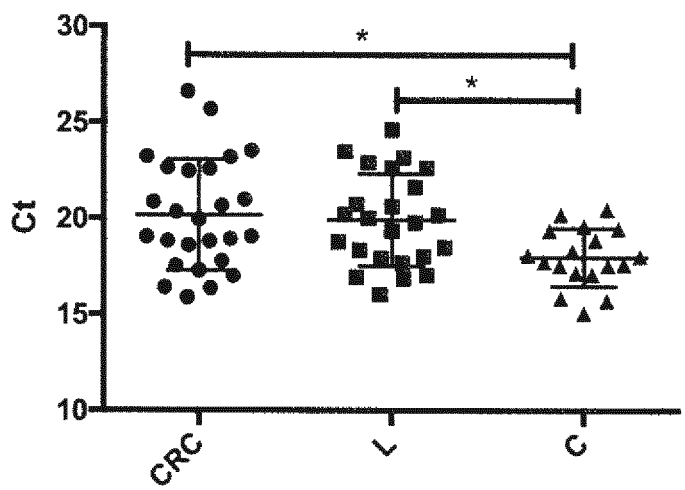
Figure 19. Ct value of B48 in CRC, L and C groups.

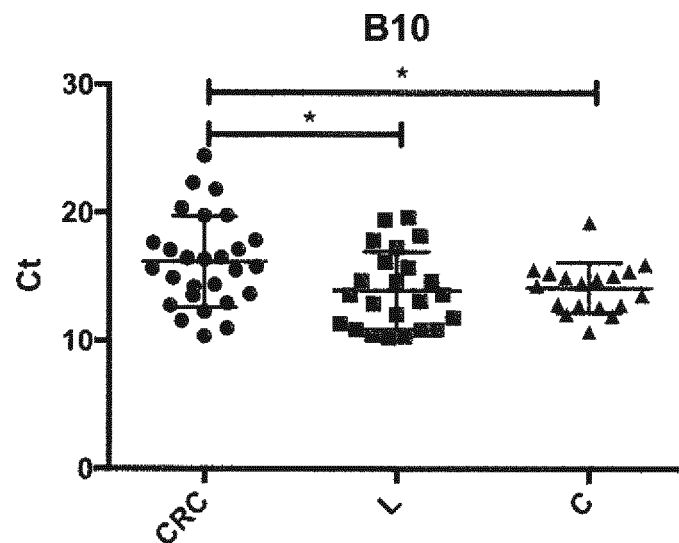
Figure 20. Ct value of B10 in CRC, L and C groups.
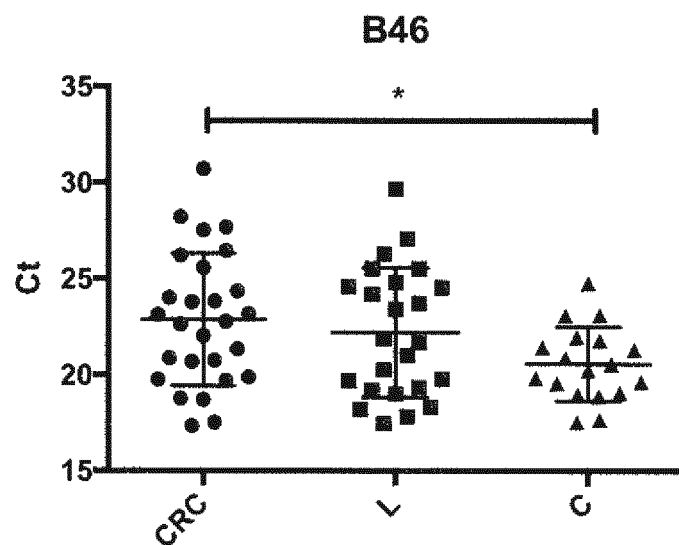
Figure 21. Ct value of B46 in CRC, L and C groups.

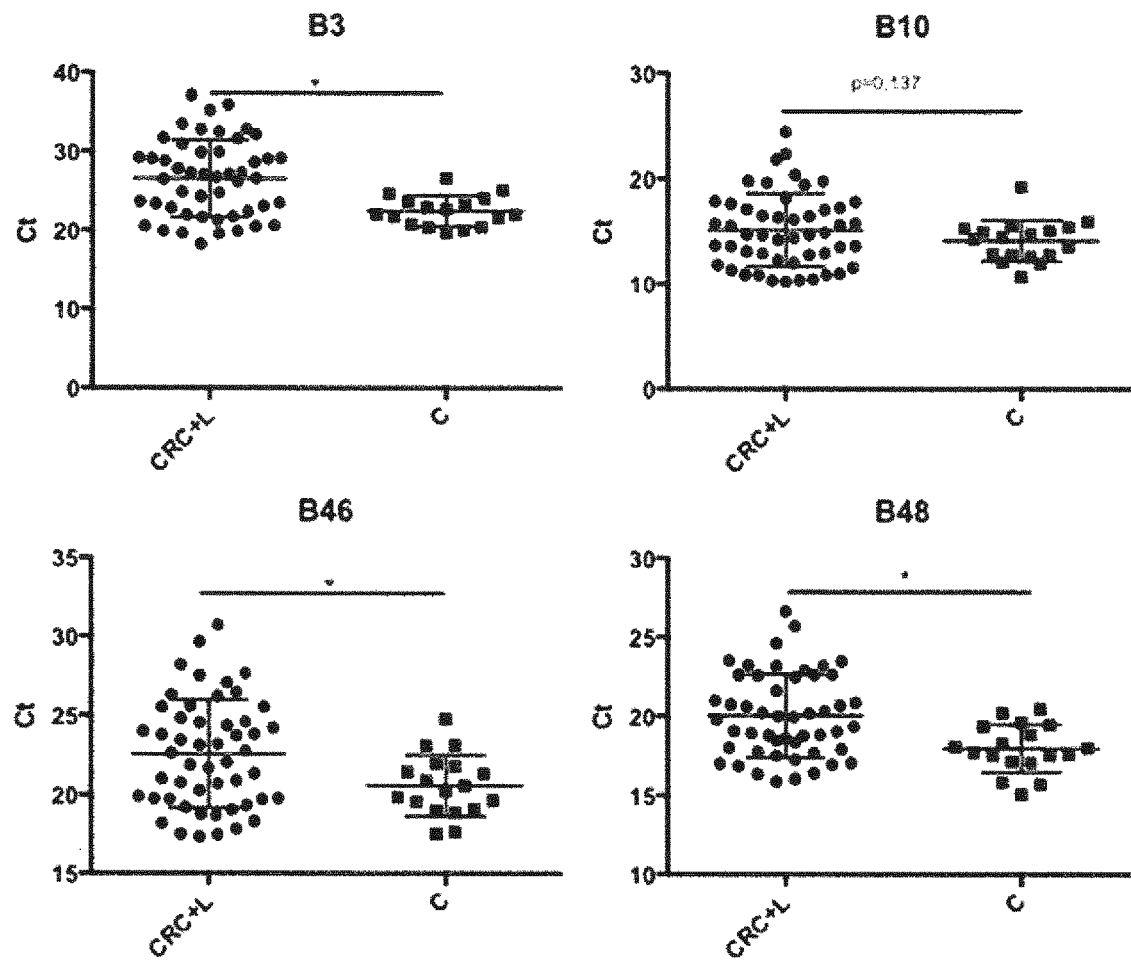
Figure 22: Ct value of B3, B10, B46 and B48 in CRC+L vs C

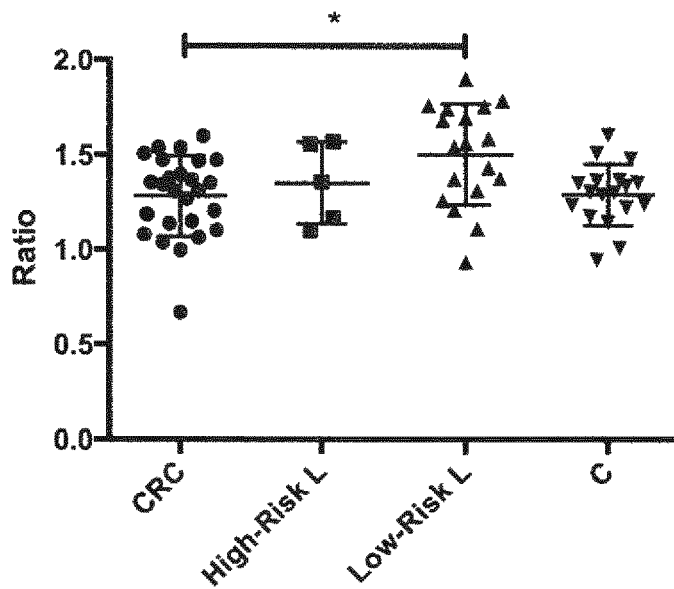
Figure 23. B48/B10 ratio value in CRC, High Risk L, Low Risk L and C groups.
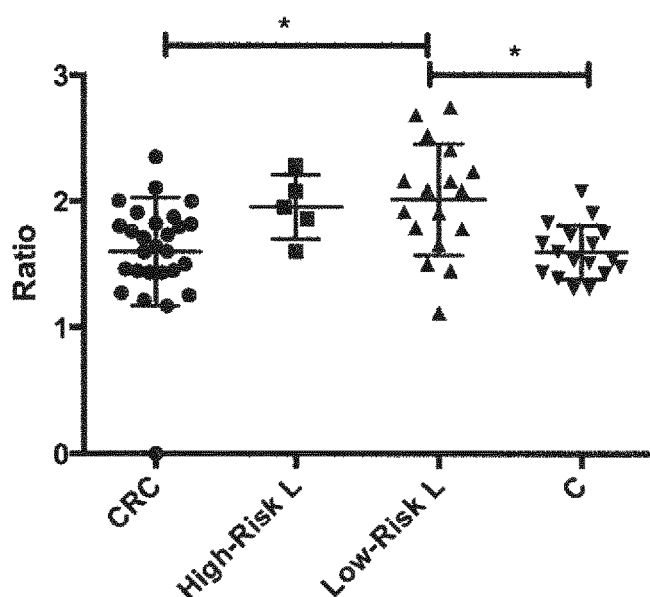
Figure 24. B3/B10 ratio value in CRC, High Risk L, Low Risk L and C groups.

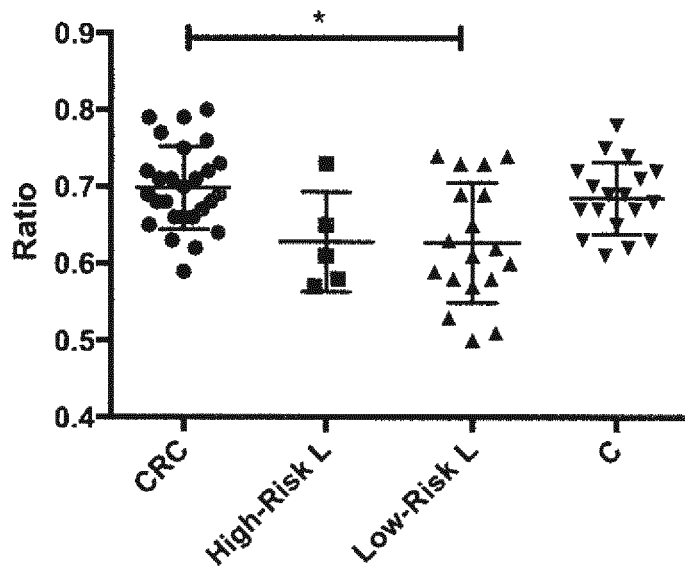
Figure 25. B46/B10 ratio value in CRC, High Risk L, Low Risk L and C groups.
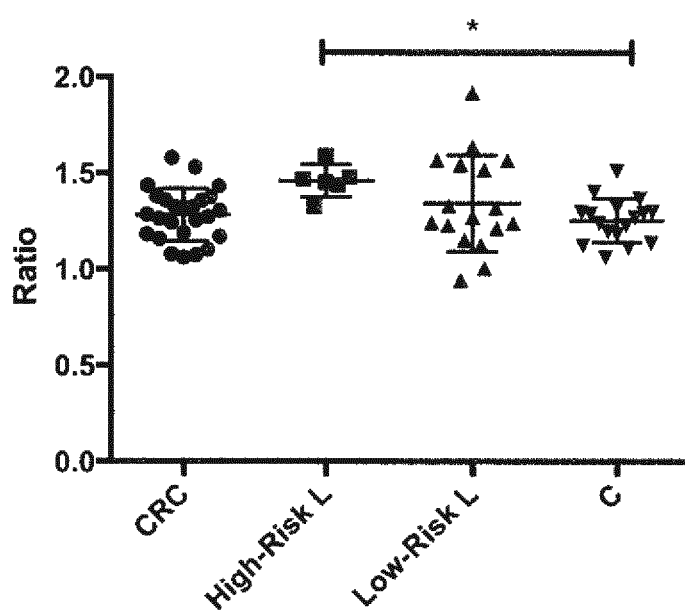
Figure 26. B3/B48 ratio value in CRC, High Risk L, Low Risk L and C groups.

METHOD FOR DIAGNOSING COLORECTAL CANCER FROM A HUMAN FECES SAMPLE BY QUANTITATIVE PCR, PRIMERS AND KIT

CROSS-REFERENCE TO RELATED PATENT APPLICATIONS

This application is a U.S. National Phase patent application, filed under 35 U.S.C. § 371, of International Application No. PCT/EP2015/054451, filed Mar. 3, 2015, which claims the priority benefit of European Patent Application No. 14382074.4, filed Mar. 3, 2014, the entire contents of each of which are incorporated herein by reference in their entireties and for all purposes.

INCORPORATION-BY-REFERENCE OF SEQUENCE LISTING

The content of the following submission on ASCII text file is incorporated herein by reference in its entirety: a computer readable form (CRF) of the Sequence Listing (file name: 51549-501N01US_Sequence_Listing.txt, date recorded: Aug. 30, 2016, size: 8,192 bytes).

FIELD OF INVENTION

The present invention relates to the field of detection of colorectal cancer (CRC). Specifically it relates to methods for the early detection, risk screening and monitoring of CRC and/or adenomatous polyps in a human subject based on the quantification of one or more 16S rDNA bacterial sequences in feces. It further relates to the use of said bacterial sequences as biomarkers of colorectal cancer and/or adenomatous polyps; to a kit comprising a reagent and instructions for the quantification of said bacterial sequences; and to nucleic acids for the quantification of said 16S rDNA bacterial sequences.

BACKGROUND OF THE INVENTION

Colorectal cancer (CRC) is the second leading cause of cancer death in Europe and in the United States, and is the most frequently diagnosed cancer in Europe, with over 400,000 new cases and 200,000 deaths in 2008. These data reflect that preventive measures need to be taken.

The most effective and economic measure to reduce CRC incidence and mortality are CRC risk screening and monitoring tests. Screening tests are grouped into those that primarily detect cancer early; and those that can detect cancer early and also can detect adenomatous polyps, thus providing a greater potential for prevention through polypectomy (i.e., polyps removal), see American Cancer Society (ACS) 2008 screening and surveillance guidelines, Levin et al. (CA Cancer J Clinicians, 2008; 58(3)130-160). Different screening guidelines being of application at people of average risk and at people with increased or high risk (www.cancer.org/cancer/colonandrectumcancer/moreinformation/colonandrectumcanc erearlydetection/colorectal-cancer-early-detection-acs-recommendations).

Currently, the tests that primarily detect CRC are fecal tests, which include: i) fecal blood tests: the fecal occult blood test ("FOBT") and the fecal immunochemical test ("FIT"); and ii) the stool DNA ("sDNA") test (see, www.cancer.org/cancer/colonandrectumcancer/moreinformation/colonandrectumcance rearlydetection/colorectal-cancer-early-detection-screening-tests-used).

i) Fecal Blood Tests

Both the FOBT and FIT screen for CRC by detecting the amount of blood in a feces sample. The tests are based on the premise that neoplastic tissue, particularly malignant tissue, bleeds more than typical mucosa, with the amount of bleeding increasing with polyp size and cancer stage. Multiple testing is recommended because of intermittent bleeding. While fecal blood tests may detect some early stage tumors in the lower colon, they are unable to detect (i) CRC in the upper colon because any blood will be metabolized and/or (ii) smaller adenomatous polyps, thus creating false negatives. Any gastro-intestinal bleeding due to hemorrhoids, fissures, inflammatory disorders (ulcerative colitis, Crohn's disease), infectious diseases, even long distance running, will create false positives (Beg et al., J Indian Acad Clin Med, 2002; 3(2)153-158). Current ACS guidelines (Levin et al., CA Cancer J Clinicians, 2008; 58(3)130-160) recommend annual screening of average-risk adults aged 50 and older using Guaiac-based fecal occult blood test (gFOBT). FOBT is the only recommended test in the European Union (Segnan N. et al., 2010, European guidelines for quality assurance in colorectal cancer screening and diagnosis. Luxembourg: Office for Official Publications of the European Communities). Both guidelines recommend that any positive FOBT test should be followed up with colonoscopy.

ii) Stool DNA ("sDNA") Test

The sDNA test measures a variety of DNA markers from a stool sample. The sDNA test currently available Cologuard™ from Exact Sciences Corp. (Madison, Wis.), measures a multiple marker panel which includes separate point mutations in K-ras, APC, and P53 genes; a probe for BAT-26; a marker for DNA integrity (DIA); and methylation of the vimentin gene (Levin et al., CA Cancer J Clinicians, 2008; 58(3)130-160). While some guidelines recommend sDNA testing other guidelines are more conservative and do not recommend it. In one study a version of the sDNA test was superior to FOBT, but it still only detected 15% of the advanced adenomas (Imperiale et al., N Engl J Med, 2004; 351:2704-2714).

The tests indicated in the ACS guidelines as being able to detect adenomatous polyps and cancer are structural tests which include: (i) colonoscopy, (ii) flexible sigmoidoscopy ("FSIG"), (iii) double-contrast barium enema ("DCBE"), and (iv) CT colonography ("CTC", virtual colonoscopy). All these methods require both purging of a patient's bowels and pumping air into the colon to aid visualization. Current guidelines encourage the use of tests designed to detect both early cancer and adenomatous polyps if resources are available and patients are willing to go an invasive test.

A colonoscopy is an invasive technique that allows direct inspection of all mucosal extraction biopsies and resection of the colon and rectum polyps in one session. This not only improves the prognosis of colorectal cancer but prevents the disease. The main disadvantages associated with this technique are however: high cost because it requires trained personnel, the risk of death associated with anesthesia and risk of intestinal perforation (Garborg K. et al., Ann Oncol., 2013; 24(8):1963-72).

Colonoscopy in the hands of an experienced professional is 100% sensitive and 100% specific, but because of colonoscopy's risk and cost, previous to colonoscopy it is required to carry out a screening of risk population using non-invasive tests such as the above mentioned fecal tests for detection of blood in feces, i.e., gFOBT or FIT, which as above mentioned lead to an important number of false positive results, thus to an equal number of unnecessary colonoscopies. This reflects the need for an effective non-invasive CRC screening tool. The current lack of an efficient CRC screening tool results in long waiting lists (>6 weeks) for colonoscopy and high amount of economic resources allocated for colonoscopies that were wrongly indicated. This situation represents both for public and private health a significant spending and results in a saturation of the system (Allison J. et al., Practical Gastroenterology, 2007, 3: 21-32).

Therefore, there is a need for an improvement of the sensitivity, specificity, invasiveness and/or cost-effectiveness of the actual methods for the early detection and monitoring of CRC and/or adenomatous polyps.

The genetic basis and natural history of CRC are well defined, considering that less than 5% of CRCs are hereditary, and majority are sporadic, diagnosed in patients with no personal or family history of colonic neoplasm. The etiology of this disease is still unknown, although a multifactorial origin in which endogenous and exogenous factors are actively involved in tumor development is suspected. These factors are: age, tobacco, personal history of inflammatory bowel disease, diet, lifestyle, and microbiota.

Lately, it has been shown that bacterial communities in the colonic mucosa of CRC patients differ from healthy individuals and the intestinal microbiota has been proposed as a determining agent in the development and progression of CRC along its stages (Chen W et al., PLoS One, 2012; 7(6):e39743; Zhu Q et al., Tumour Biol., 2013; 34(3):1285-300; Ahn J et al., J Natl Cancer Inst., 2013; 105(24):1907-11; Na wu et al., Microbial ecology, 2013; 66(2):462-470).

WO2012/170478 refers to methods for detecting adenomas and colorectal cancer using a bacterial signature. 16rRNA gene pyrosequencing to characterize adherent bacterial communities from mucosal biopsies was carried out. Relative abundances between adenoma and non-adenoma subjects were calculated, concluding that development of adenomas in associated with changes in the relative abundance of various bacterial taxa present in gut mucosa. Specifically, it was determined abundance of *Fusobacterium nucleatum* in the normal rectal mucosa of subjects with and without adenomas by qPCR quantification of the 16S rRNA gene (16sDNA), concluding that abundance is higher in adenoma cases compared to controls. According to said data, the use of *F. nucleatum* as biomarker of colorectal carcinogenesis is suggested.

The importance of gut microbiota as an agent in the development and evolution of CRC throughout its stages has also been confirmed in a study conducted by one of the inventors in mucosal biopsy samples, which shows the association of abundance of [W]Firmicutes, Actinobacteria and *Escherichia coli* in patients with colorectal cancer and of *Faecalibacterium prausnitzii* in healthy subjects (Mas de Xaxars T., 2012, Dipósit legal: GI. 1664-2012, hdl.handle-.net/10803/94513).

It is well known in the art, however, that there are differences between the microbiota composition in mucosal biopsies and feces samples. Lepage et al. (Inflamm Bowel Dis., 2005; 11(5):473-80) shows that in a given individual the dominant species differ between mucosa-associated and fecal microbiota. Similarly, Eckburg et al. (Science, 2005; 308(5728):1635-1638) reported statistically significant differences between the phylogenetic lineages found in mucosal and feces samples, postulating that the fecal microbiota represents a combination of shed mucosal bacteria and separate non-adherent luminal population.

Nechvatal et al. (J Microbiol Methods., 2008; 72(2):124-32) showed that fecal DNA might be used as a source for epidemiological studies of intestinal bacteria and human cancer markers. Notably, it describes the quantification by real-time quantitative PCR of bacterial and human sequences in DNA extracts from human feces. Balamurugan et al. (J Gastroenterol Hepatol., 2008; 23:1298-303) describe the quantification by real-time quantitative PCR of specific bacteria with metabolism products which are know to have a protective effect (i.e., *Eubacterium rectale* and *Faecalibacterium prausnitzii*, which are butyrate-producing bacteria) or to be toxic or carcinogenic (i.e., *Desulfovibrio* (sulphate-reducing bacteria) and *Enterococcus faecaelis* (that produces extracellular superoxide) in the feces of patients with colorectal cancer. However, both are silent on the determination of the diagnostic or predictive value of such bacterial sequences as biomarkers for CRC.

In US2014/0024036, Wang et al. describe a method for CRC detection comprising the quantification of the nusG gene of *F. nucleatum* (FNN) by qPCR from human feces of CRC patients and controls, detecting CRC with a sensitivity of 57% and specificity of 89.5%.

Although, methods for the detection and/or quantification of DNA biomarkers for CRC in feces have been described, there is still a need for reliable methods of early diagnosis, risk screening or patient monitoring of CRC in a human subject from feces samples. The availability of such a method would enable to effectively prevent CRC through early detection and to reduce the number of unnecessary structural examination tests, such as colonoscopies, which are nowadays performed in individuals suspected of CRC more often than necessary due to the low accuracy of the FOBT and FIT tests which are the current standard screening methods for CRC detection.

SUMMARY OF THE INVENTION

The first aspect of the invention relates to a method of screening for colorectal cancer (CRC) and/or adenomatous polyps in a human subject which comprises:
  i. quantifying at least one 16S rDNA bacterial sequence selected from the list consisting of SEQ ID NO:1, SEQ ID NO:4, SEQ ID NO:7 and SEQ ID NO:10 or the complementary 16S rRNA sequence thereof, from a feces sample from said subject; and
  ii. diagnosing, early detecting, determining recurrence, determining risk of developing, or predicting for CRC and/or polyps in a human subject; or determining whether a colonoscopy should be performed in said human subject; or determining prognosis wherein said human subject is a patient diagnosed with CRC and/or polyps; or guiding a therapy in a patient with CRC and/or polyps from the quantification levels of at least one of said sequences.

In a second aspect, the invention relates to the use of at least one 16S rDNA bacterial sequence selected from the list consisting of SEQ ID NO:1, SEQ ID NO:4, SEQ ID NO:7 and SEQ ID NO:10 or the complementary 16S rRNA sequence thereof, as a biomarker for diagnosing, early detecting, determining recurrence, determining risk of developing, or predicting for CRC and/or polyps in a human subject; or determining whether a colonoscopy should be performed in said human subject; or determining prognosis wherein said human subject is a patient diagnosed with CRC and/or polyps; or guiding a therapy in a patient with CRC and/or polyps, wherein said bacterial sequences are quantified from a feces sample of said human subject.

In a third aspect, the invention relates to a kit comprising:
a. a reagent selected from the group consisting of:
   i. nucleic acid probes capable of specifically hybridizing with at least one 16S rDNA sequence selected from the list consisting of SEQ ID NO:1, SEQ ID NO:4, SEQ ID NO:7 and SEQ ID NO:10 or the complementary 16S rRNA sequence thereof; or
   ii. a pair of nucleic acid primers capable of specifically amplifying at least one 16S rDNA sequence selected from the list consisting of SEQ ID NO:1, SEQ ID NO:4, SEQ ID NO:7 and SEQ ID NO:10; and
b. instructions for quantifying the levels of one or more of said sequences from a human feces sample according to a method of the present invention.

In a forth aspect, the invention relates to a nucleic acid sequence selected from the group consisting of SEQ ID NO: 2, SEQ ID NO: 13, SEQ ID NO: 5, SEQ ID NO: 6, SEQ ID NO: 8, SEQ ID NO: 9, SEQ ID NO: 11, and SEQ ID NO: 12 or with at least 90% identity thereof.

In a fifth aspect, the invention relates to the use of a nucleic acid sequence selected from the group consisting of SEQ ID NO: 2, SEQ ID NO: 13, SEQ ID NO: 5, SEQ ID NO: 6, SEQ ID NO: 8, SEQ ID NO: 9, SEQ ID NO: 11, and SEQ ID NO:12; or with at least 90% identity thereof in a method of screening of the invention.

BRIEF DESCRIPTION OF THE DRAWINGS

The following symbols are used in the figures from 1 to 7 with the following meaning:
* means that statistical significance is p=0.05
** means that statistical significance is p=0.01
** means that statistical significance is p=0.005
The figures from 8 to 26 statistical significance is represented by * and the p-value appears in the corresponding tables.

FIG. 14. Absolute Ct values for B3 in CRC and C groups.

FIG. 15. Absolute Ct values for B48 in CRC and C groups.

FIG. 16. Absolute Ct values for B10 in CRC and C groups.

FIG. 17. Absolute Ct values for B46 in CRC and C groups.

FIG. 18. Absolute Ct values for B3 in CRC, L and C groups.

FIG. 19. Absolute Ct values for B48 in CRC, L and C groups.

FIG. 20. Absolute Ct values for B10 in CRC, L and C groups.

FIG. 21. Absolute Ct values for B46 in CRC, L and C groups.

FIG. 22. Absolute Ct values for B3, B10, B46 and B48 in CRC+L vs C.

FIG. 23. B48/B10 ratio of absolute Ct values in CRC, High Risk L, Low Risk L and C groups.

FIG. 24. B3/B10 ratio of absolute Ct values in CRC, High Risk L, Low Risk L and C groups.

FIG. 25. B46/B10 ratio of absolute Ct values in CRC, High Risk L, Low Risk L and C groups.

FIG. 26. B3/B48 ratio of absolute Ct values in CRC, High Risk L, Low Risk L and C groups.

DETAILED DESCRIPTION OF THE INVENTION

Figure 1:
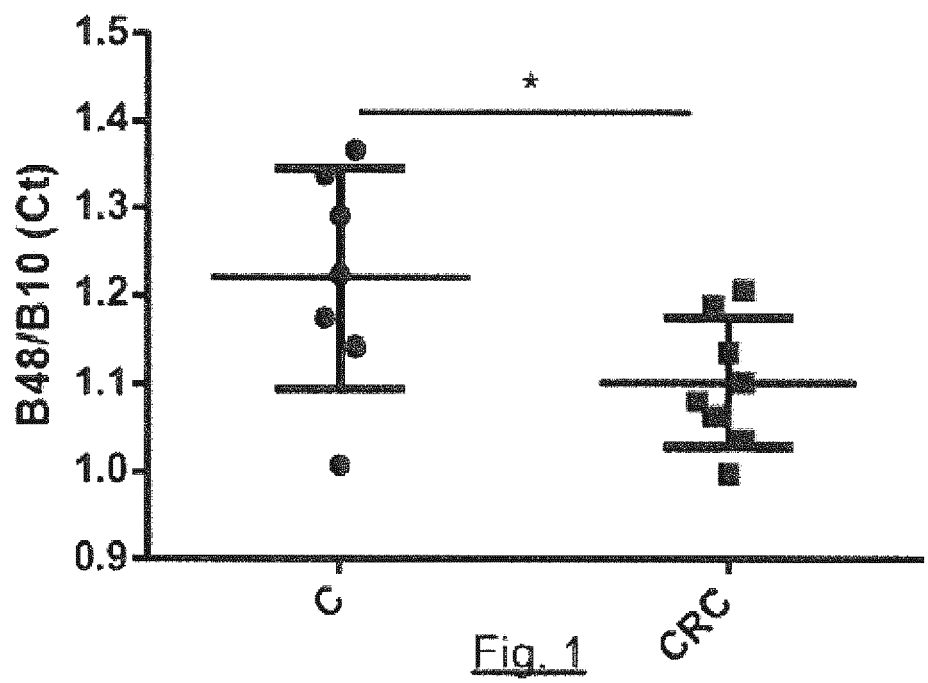
FIG. 1. Ratio of Ct values for 2 sequences: SEQ ID NO: 10/SEQ ID NO: 4. CRC represents the values obtained from feces samples of cancer colorectal patients, and C represents the control values obtained from healthy patients.

In the present invention, specific bacterial sequences associated to diagnosis, early detection, risk screening and monitoring of CRC and/or adenomatous polyps have been identified.

The first aspect of the invention relates to a method of screening for colorectal cancer (CRC) and/or adenomatous polyps in a human subject which comprises:
   i. quantifying at least one 16S rDNA bacterial sequence selected from the list consisting of SEQ ID NO:1, SEQ ID NO:4, SEQ ID NO:7 and SEQ ID NO:10 or the complementary rRNA sequence thereof, from a feces sample of said subject; and ii. diagnosing, early detecting, determining recurrence, determining risk of developing, or predicting for CRC and/or polyps in a human subject; or determining whether a colonoscopy should be performed in said human subject; or determining prognosis wherein said human subject is a patient diagnosed with CRC and/or polyps; or guiding a therapy in a patient with CRC and/or polyps from the quantification levels of at least one of said sequences.

In the present application, the sequence identified by SEQ ID NO: 1 is also identified as "B3". Similarly, SEQ ID NO: 4 is also identified as "B10", SEQ ID NO: 7 is also identified as "B46" and SEQ ID NO: 10 is also identified as "B48", and these designations are used interchangeably. B3, B10, B46 and B48 were the names used by the inventors of the present application to identify the sequences during performance of all experiments carried out to arrive at the present invention. The sequences identified by SEQ ID NO: 1, 4, 7 and 10 are available in the EMBL-EBI public sequences database under the following accession numbers: GQ411111.1 (SEQ ID NO: 1), GQ411118.1 (SEQ ID NO: 4), GQ411150.1 (SEQ ID NO: 7), GQ411152.1 (SEQ ID NO: 10).

B3, B10, B46 and B48 sequences correspond to denaturing gradient gel electrophoresis (DGGE) gel bands previously isolated from uncultured bacterium isolates. BLAST analyses were carried out with the aim to identify the corresponding bacterial species:

Best match BLAST for B3 16S rDNA: *Collinsella aerofaciens*;

Best match BLAST for B10 16S rDNA: *Faecalibacterium prausnitzii*;

Best match BLAST for B46 16S rDNA: *Faecalibacterium prausnitzii, Subdoligranulum variabil*;

Best match BLAST for B48 16S rDNA: *Ruminococcus, Roseburia, Coprococcus*.

As used herein, the term "colorectal cancer", "CCR" or "CRC" is used for cancer that starts in the colon or the rectum. These cancers can also be referred to separately as colon cancer or rectal cancer, depending on where they start. Colon cancer and rectal cancer have many features in common.

According to the ACS, several types of cancer can start in the colon or rectum. More than 95% of colorectal cancers are a type of cancer known as adenocarcinomas. These cancers start in cells that form glands that make mucus to lubricate the inside of the colon and rectum. Other, less common types of tumors may also start in the colon and rectum. These include: carcinoid tumors, gastrointestinal stromal tumors (GISTs), lymphomas and sarcomas.

The goal of cancer screening is to reduce mortality through a reduction in incidence of advanced disease. To this end, modem CRC screening can achieve this goal through the detection of early-stage adenocarcinomas and the detection and removal of adenomatous polyps, the latter generally accepted as nonobligate precursor lesions.

An "adenomatous polyp" is a non-cancerous growth of abnormal glandular cells on the inner lining of an organ such as the colon. For example, three types of adenomatous polyps that can grow in the colon are tubular, villous, and tuberovillous adenomas. Adenomatous polyps are common in adults over age 50 years, but the majority of polyps will not develop into adenocarcinoma; histology and size determine their clinical importance.

According to the ACS, tests that have the best chance of finding both polyps and cancer are preferred, as having their polyps found and removed keeps some people from getting colorectal cancer. Preferably, the method of the invention is a method for the screening of CRC and adenomatous polyps.

In a particular embodiment, the method of the invention is a method of screening for the diagnosis or detection of CRC and/or adenomatous polyps, preferably for the early detection of CRC and/or adenomatous polyps. The expression "early detection" refers to detection before the presence of clinical signs. The terms "detection" and "diagnosis" are used interchangeably in the present application. The method of the invention is found to be a potent tool to prevent colorectal cancer through an early stage disease diagnostic.

In a particular embodiment, the screening method of the invention is carried out in subjects aged 50 years and older. Average risk women and men aged 50 years and older are encouraged to follow colorectal cancer screening tests (see Table 2 of Levin et al., CA Cancer J Clinicians, 2008; 58(3)130-160, which is hereby incorporated by reference).

In another embodiment, the screening method of the invention is carried out in increased and/or high risk subjects. Specific guidelines are of application to increased or high risk patients.

According to the ACS (see Table 3 of Levin et al., CA Cancer J Clinicians, 2008; 58(3)130-160, which is hereby incorporated by reference), increased and high risk subjects include the following:

Increased Risk
subjects with a history of polyps on prior colonoscopy;
subjects with colorectal cancer, and
subjects with a family history of colorectal cancer or adenomatous polyps.

High Risk
subjects with familial adenomatous polyposis (FAP) diagnosed by genetic testing, or suspected FAP without genetic testing;
subjects with hereditary non-polyposis colon cancer (HNPCC or Lynch syndrome), or at increased risk of HNPCC based on family history without genetic testing; and
subjects with Inflammatory bowel disease, such as chronic ulcerative colitis or Crohn's disease.

One goal of the present invention is to provide a pre-diagnosis tool. Specifically, the present invention provides a method for diagnosing colorectal cancer before having clinical signs by identifying subjects with predisposition or risk of developing CRC and/or adenomatous polyps.

In a particular embodiment, the method of screening of the present invention is a method for determining the risk of developing CRC and/or adenomatous polyps in a human subject which comprises:

i. quantifying at least one 16S rDNA bacterial sequence selected from the list consisting of SEQ ID NO:1, SEQ ID NO:4, SEQ ID NO:7 and SEQ ID NO:10 or the complementary 16S rRNA sequence thereof, from a feces sample of said subject; and ii. determining the risk of developing CRC and/or adenomatous polyps from the quantification levels of at least one of said sequences.

In a preferred embodiment, the method of screening of the present invention is a method for determining the risk of developing CRC and/or adenomatous polyps in increased and/or high risk subjects, preferably in Lynch syndrome carriers.

The term "Lynch syndrome" refers to hereditary non-polyposis colorectal cancer or HNPCC, which is an inherited condition that greatly increases a person's risk for colorectal cancer, as well as cancer of the lining of the uterus (endometrial cancer), ovarian cancer, and some other cancers. People with this condition tend to develop cancer at a young age, often without first having many polyps.

The method of screening of the invention has shown in Example 4 (Tables 3 and 4) the ability to discriminate in a statistically significant manner between Lynch syndrome patients with polyps (high risk population) and without polyps (low risk population). Quantification of SEQ ID NO: 4 (B10) and determination of the SEQ ID NO: 7 (B46)/SEQ ID NO: 4 (B10) ratio appear to be good indicators according to the results in Example 4. Accordingly, SEQ ID NO: 4 (B10) and SEQ ID NO: 7 (B46)/SEQ ID NO: 4 (B10) ratio are preferred biomarkers for use in the method of the invention for screening of presence of polyps.

In subjects with a history of polyps on prior colonoscopy or with history of colorectal cancer after cancer resection, screening tests are carried out for monitoring or surveillance purposes, i.e. to detect cancer and/or adenomatous polyps recurrence in said human subjects.

In a further particular embodiment, the method of screening of the present invention is a method of monitoring for the detection of colorectal cancer (CRC) and/or adenomatous polyps in a human subject with a previous history of polyps and/or colorectal cancer which comprises:
  i. quantifying at least one 16S rDNA bacterial sequence selected from the list consisting of SEQ ID NO:1, SEQ ID NO:4, SEQ ID NO:7 and SEQ ID NO:10 or the complementary 16S rRNA sequence thereof, from a feces sample of said subject; and
  ii. determining recurrence of CRC and/or adenomatous polyps from the quantification levels of at least one of said sequences.

The method of screening of the invention has shown in Example 8 (Table 8) the ability to discriminate in a statistically significant manner between Lynch patients with previous history of CRC and polyps in his last colonoscopy (high risk population) and Lynch patients without previous history of CRC and without polyps in his last colonoscopy (low risk population). Particularly remarkable results being obtained with the quantification of SEQ ID NO: 1/SEQ ID NO: 4 (B3/B10), SEQ ID NO: 4/SEQ ID NO: 7 (B10/B46), SEQ ID NO: 1/SEQ ID NO: 10 (B3/B48) and SEQ ID NO: 10/SEQ ID NO: 4 (B48/B10) ratios.

Accordingly, SEQ ID NO: 1/SEQ ID NO: 4 (B3/B10), SEQ ID NO: 4/SEQ ID NO: 7 (B10/B46), SEQ ID NO: 1/SEQ ID NO: 10 (B3/B48) and SEQ ID NO: 10/SEQ ID NO: 4 (B48/B10) ratios are preferred biomarkers for use in the method of the invention for screening/monitoring of presence of polyps, preferably in increased or high risk patients, such as Lynch patients with a history of CRC.

In a further particular embodiment, the method of screening of the present invention is a method for determining whether a colonoscopy should be performed in a human subject which comprises:
  i. quantifying at least one 16S rDNA bacterial sequence selected from the list consisting of SEQ ID NO:1, SEQ ID NO:4, SEQ ID NO:7 and SEQ ID NO:10 or the complementary 16S rRNA sequence thereof, from a feces sample of said subject; and
  ii. determining whether a colonoscopy should be performed in said human subject from the quantification levels of at least one of said sequences.

One of ordinary skill in the art knows several methods and devices for the quantification and analysis of the bacterial markers of the present invention. The term "quantifying" refers to the ability to quantify the amount of a specific nucleic acid sequence in a sample. Molecular biology methods for measuring quantities of target nucleic acid sequences are well known in the art. These methods include but are not limited to end pointPCR, competitive PCR, reverse transcriptase-PCR (RT-PCR), quantitative PCR (qPCR), reverse transcriptase qPCR (RT-qPCR), PCR-ELISA, DNA microarrays, in situ hybridization assays such as dot-blot or Fluorescence In Situ Hybridization assay (FISH), branched DNA (Nolte, Adv. Clin. Chem., 1998, 33:201-235) and to multiplex versions of said methods (see for instance, Andoh et al., Current Pharmaceutical Design, 2009; 15, 2066-2073). Preferred primers and/or probes react in a predictable manner, typically by offering a direct and linear response to increasing amounts of bacterial nucleic acid sequences. By preparation of and by comparison to appropriate standards, one can readily quantify the amount of a given nucleic acid sequence in a sample.

Preferably, said nucleic acid sequence is a 16S rDNA sequence selected from the list consisting of SEQ ID NO:1, SEQ ID NO:4, SEQ ID NO:7 and SEQ ID NO:10.

One particularly preferred quantification method is FISH, which combines probe hybridization with fluorescent light microscopy, confocal laser microscopy or flow cytometry for direct quantification of individual bacterial sequences. For reviews of FISH methodology, see, e.g., Harmsen et al., Appl Environ Microbiol, 2002; 68 2982-2990, Kalliomaki et al., J Allerg Clin Immunol, 2001; 107 129-134; Tkachuk et al., Genet. Anal. Tech. Appl., 1991; 8: 67-74; Trask et al., Trends Genet., 1991; 7 (5): 149-154; and Weier et al., Expert Rev. Mol. Diagn., 2002, 2(2):109-119; and U.S. Pat. No. 6,174,681.

Another particularly preferred quantification method is quantitative PCR (qPCR), also known as real-time PCR. The PCR process is well known in the art and is thus not described in detail herein. Q-PCR technology overview and protocols are available from vendors such as from Sigma-Aldrich on SYBR Green qPCR applications, see for instance www.sigmaaldrich.com/technical-documents/protocols/biology/sybr-green-qper.html or www.sigmaaldrich.com/life-science/molecular-biology/pcr/quantitative-pcr/qpcr-technical-guide.html. For a review of qPCR methods to quantify the abundance and expression of bacterial gene markers see, e.g., Smith CJ and Osborn AM., FEMS Microbiol Ecol., 2009; 67(l):6-20.

The term "quantification levels" might be the concentration (DNA amount per unit of volume), the DNA amount per number of cells, the cycle threshold value (Ct value) or any mathematical transformation thereof. In a preferred embodiment, the quantification of said bacterial sequences is performed by qPCR. I a more preferred embodiment, the quantification of said bacterial sequences is performed by qPCR and the quantification levels is the Ct value. The Ct (cycle threshold) value is defined as the number of qPCR cycles required for the fluorescent signal to cross the threshold. Ct levels are inversely proportional to the amount of target nucleic acid in the sample (i.e., the lower the Ct level the greater the amount of target nucleic acid in the sample).

Quantification of the abundance of a target nucleic acid sequence (e.g. SEQ ID NO: 1) in a faecal sample might be absolute or relative. Relative quantification is based on one or more internal reference genes, i.e., 16S rRNA genes from reference strains, such as determination of total bacteria (Eubacteria) using universal primers and expressing the abundance of the target nucleic acid sequence as a percentage of Eubacteria (e.g. SEQ ID NO: 1/Eubacteria ratio). Absolute quantification gives the exact number of target molecules by comparison with DNA standards.

In a particular embodiment, the method of the invention further comprises after step i) comparing the subject sample levels with the levels in a control sample, wherein when there is a deviation of the levels of one or more of the sequences selected from the list consisting of SEQ ID NO: 1, SEQ ID NO: 4, SEQ ID NO: 7 and SEQ ID NO: 10 (preferably, a statistically significantly deviation) from the levels of the respective sequence(s) in the control sample is indicative of CRC and/or adenomatous polyps. For example, wherein quantification levels present a deviation from the median (cut-off) value plus(+)/minus(−) the standard deviation of the respective level(s) measured in a control sample is indicative of CRC and/or adenomatous polyps.

In a preferred embodiment, wherein concentration levels of one or more of said sequences in said subject sample are lower than the median(cut-off) value minus the standard deviation of the levels of the respective sequence(s) measured in a control sample is indicative of CRC and/or adenomatous polyps. In another preferred embodiment, wherein Ct levels of one or more of said sequences in said subject sample are higher than the median (cut-off) value plus the standard deviation of the levels of the respective sequence(s) measured in a control sample is indicative of CRC and/or adenomatous polyps.

The term "control sample" may refer to a collection of control samples of the population of reference, for instance the control samples may be samples from healthy subjects, from subjects without adenomatous polyps, from subjects without previous history of adenomatous polyps and/or colorectal cancer and combinations thereof.

Classification of human subjects under one of the abovementioned populations of reference is carried out by a colonoscopy exploration. For instance, "healthy subjects" are those who in a previous colonoscopy did not present either adenomatous polyps or colorectal cancer.

Preferably, the method of the invention comprises quantifying 2, 3 or 4 sequences selected from the list consisting of SEQ ID NO: 1, SEQ ID NO: 4, SEQ ID NO: 7 and SEQ ID NO: 10, preferably all 4 sequences.

In one particular embodiment, the method of the invention comprises the quantification of at least two sequences selected from the list consisting of SEQ ID NO: 1, SEQ ID NO: 4, SEQ ID NO: 7 and SEQ ID NO: 10 and determining the relationship between at least two of said sequences. Preferably, the relationship between two, three or four of said sequences (e.g. ratio, multivariant analysis, etc.) is determined.

In a preferred embodiment, the ratio between these at least two sequences is obtained by dividing the quantification levels of a first sequence by the quantification levels of a second sequence. For instance, the ratio of concentration of the sequences SEQ ID NO: 10/SEQ ID NO: 4 is obtained by dividing the concentration of the sequence SEQ ID NO: 10 by the concentration of the sequence SEQ ID NO: 4. The SEQ ID NO: 10/SEQ ID NO: 4 ratio could also be obtained by dividing the Ct value of the sequence identified by SEQ ID NO: 10 by the Ct value of the sequence identified by SEQ ID NO: 4.

In a further embodiment of the method of the invention, at least two of said bacterial sequences are quantified in step i) and at least one of the ratios of the levels of said sequences in the subject sample is determined, further comprising comparing at least one of said ratios in said subject with the respective ratio(s) in a control sample, wherein a deviation from the ratio in said control sample (preferably, a statistically significant deviation) is indicative of CRC and/or adenomatous polyps. For example, wherein one or more of said ratios present a deviation from the median (cut-off) value plus(+)/minus(−) the standard deviation of the respective ratio(s) measured in a control sample is indicative of CRC and/or adenomatous polyps.

The term "statistically significant" when referring to differences between the test sample and the control sample, relates to the condition when using the appropriate statistical analysis the probability of the groups being the same is less than 5%, e.g. p<0.05. In other words, the probability of obtaining the same results on a completely random basis is less than 5 out of 100 attempts. A person skilled in the art will know how to choose the appropriate statistical analysis. Typically, the appropriate statistical analysis is determined based on whether the variable under study has a normal distribution, for instance by using the test of Kolmogorov-Smirnov. Preferably, in those cases where there is a normal distribution, a parametric model such as t-test or ANOVA test might be used; and where there is not a normal distribution then a non-parametric model such as Mann-Whitney U test or Kruskal-Wallis test might be used.

In a particular embodiment, sensitivity, specificity, accuracy, ROC analysis results or a combination thereof are used to describe the screening method of the invention. In particular, they are used to quantify how good and reliable the method is.

There are several terms that are commonly used along with the description of sensitivity, specificity and accuracy. They are true positive (TP), true negative (TN), false negative (FN), and false positive (FP). If a disease is proven present in a patient, the given screening test also indicates the presence of disease, the result of the test is considered true positive. Similarly, if a disease is proven absent in a patient, the screening test suggests the disease is absent as well, the test result is true negative (TN). Both true positive and true negative suggest a consistent result between the screening test and the proven condition (also called standard of truth). However, no medical test is perfect. If the screening test indicates the presence of disease in a patient who actually has no such disease, the test result is false positive (FP). Similarly, if the result of the screening test suggests that the disease is absent for a patient with disease for sure, the test result is false negative (FN). Both false positive and false negative indicate that the test results are opposite to the actual condition.

Sensitivity, specificity and accuracy are described in terms of TP, TN, FN and FP.

Sensitivity=TP/(TP+FN)=(Number of true positive assessment)/(Number of all positive assessment);

Specificity=TN/(TN+FP)=(Number of true negative assessment)/(Number of all negative assessment);

Accuracy=(TN+TP)/(TN+TP+FN+FP)=(Number of correct assessments)/Number of all assessments).

In a preferred embodiment, the method of screening of the present invention diagnoses, early detects, determines recurrence, determines risk of developing, or predicts for CRC and/or polyps in a human subject; or determines whether a colonoscopy should be performed in said human subject; or determines prognosis wherein said human subject is a patient diagnosed with CRC and/or polyps; or guides a therapy in a patient with CRC and/or polyps in an statistically significant manner with a sensitivity and/or specificity of at least 60%, at least 65%, at least 70%, at least 75%, at least 80%, at least 85%, at least 90%, at least 95% or preferably 100%.

As suggested by above equations, the term "sensitivity" as used herein refers to the proportion of true positives that are correctly identified by a screening test. It shows how good the test is at detecting a disease. Sensitivity ("sens") may be within the range of 0 (0%)<sens<1 (100%) and ideally, the number of false negatives equaling zero or close to equaling zero and sensitivity equaling one (100%) or close to equaling one (100%). Preferably, it has a sensitivity of 70% to 90%, 75% to 95%, 80% to 95%, 85% to 100%, or 90% to 100%. More preferably, the method of the invention has sensitivity values of at least 85%, such as about 86%, 87%, 88%, 89%, 90%, 91%, 92%, 93%, 94%, 95%, 96%, 97%, 98%, 99% or 100%.

The term "specificity" as used herein refers to the proportion of the true negatives correctly identified by a screening test. It suggests how good the test is at identifying normal (negative) condition. Specificity ("spec") may be within the range of 0 (0%)<spec<1 (100%) and ideally, the number of false positives equaling zero or close to equaling zero and specificity equaling one (100%) or close to equaling one (100%). Preferably, it has a specificity of 70% to 90%, 75% to 95%, 80% to 95%, 85% to 100%, or 90% to 100%. More preferably, the method of the invention has specificity values of at least 85%, such as about 86%, 87%, 88%, 89%, 90%, 91%, 92%, 93%, 94%, 95%, 96%, 97%, 98%, 99% or 100%.

The term "accuracy" as referred herein is the proportion of true results, either true positive or true negative, in a population. It measures the degree of veracity of a screening test on a condition, i.e., how correct is the determination and exclusion of a given condition. Accuracy ("acc") may be within the range of 0 (0%)<acc<1 (100%) and ideally, the number of false positives equaling zero or close to equaling zero and accuracy equaling one (100%) or close to equaling one (100%). Preferably, the accuracy of the method of the invention is of at least 60%, at least 65%, at least 70%, at least 75%, at least 80%, at least 85%, at least 90%, at least 95% or preferably 100%. In a preferred embodiment, it has an accuracy of 70% to 90%, 75% to 95%, 80% to 95%, 85% to 100%, or 90% to 100%. Preferably, the method of the invention has accuracy values of at least 85%, such as about 86%, 87%, 88%, 89%, 90%, 91%, 92%, 93%, 94%, 95%, 96%, 97%, 98%, 99% or 100%.

"ROC curve" is a graphic presentation of the relationship between both sensitivity and specificity and it helps to decide the optimal model through determining the best threshold (optimal cut-point) for the screening test. The area under ROC curve (AUC) provides a way to measure the accuracy of a screening test. Preferably, the AUC range values of the method of the invention are from 0.6 to 1, more preferably 0.7 to 1, more preferred values being in the range of 0.8 to 1, more preferably of 0.9 to 1. In a particular embodiment, AUC is from 0.6 to 0.8, such as from 0.6 to 0.75 or 0.65 to 0.75.

Furthermore, the sensitivity, specificity and accuracy are proportions, thus the according confidence intervals can be calculated by using standard methods for proportions well known in the art. Two types of 95% confidence intervals are generally defined around proportions. The exact confidence interval is defined by using binomial distribution to reach an exact estimate. Asymptotic confidence interval is calculated by assuming a normal approximation of the sample distribution. A person skilled in the art will know how to define the appropriate confidence interval. The choice of one or another type of confidence interval will typically depend on whether the sample proportion is a good approximation to a normal distribution.

In a particular embodiment of the method of the invention, prior to the quantification of said bacterial sequences, DNA is extracted from the feces sample. Several DNA extraction methods from fecal samples are known, all these methods relying on chemical or mechanical disruption, lysis using detergents, or a combination of these approaches (Kennedy A. et al., PLoS One, 2014; 9(2):e88982). Methods for extraction of bacterial DNA in fecal samples are known from instance from M Corist et al., Journal of Microbiological Methods, 2002; 50(2):131-139, Whitney D et al., Journal of Molecular Diagnostics, American Society for Investigative Pathology, 2004; 6(4):386-395 and WO2003/068788.

Preferred, methods use a combination of mechanical disruption, such as high speed bead beating extraction, chemical lysis and a final purification step, preferably using silica mebrane column such as those included in the commercially available DNA extraction kits "MobioPowerSoil@ DNA extraction procedure" (Mo-Bio Laboratories Inc.), FastDNA® SPIN Kit for soil procedure (MP biomedicals) and NucleoSpin® Soil (Macherey-Nagel Gmbh& Co. KG). The presence of PCR inhibitors in the DNA extracts from faecal samples such as bilirubins, bile salts and complex carbohydrates is one of the difficulties faced for the determination of DNA biomarkers in DNA extracts from feces (Fleckna et al., Mol Cell Probes, 2007; 21(4):282-7). Preferred DNA extraction methods are those that provide fecal extracts with a low amount of PCR inhibitors, such as less than 5%, preferably less than 2%, more preferably less than 1%, even more preferably less than 0.5%, such as less than 0.25%, 0.1%, 0.05% or 0.01%.

In a particular embodiment, the method of the invention comprises:

(a) determining by quantitative PCR from said human feces sample the levels of at least one 16S rDNA bacterial sequence selected from the group consisting of SEQ ID NO: 1, SEQ ID NO: 4, SEQ ID NO: 7 and SEQ ID NO: 10, wherein SEQ ID NO: 1 levels are determined using primers with at least 90% identity with respect to SEQ ID NO: 2-13, SEQ ID NO: 4 levels are determined using primers with at least 90% identity with respect to SEQ ID NO: 5-6, SEQ ID NO: 7 levels are determined using primers with at least 90% identity with respect to SEQ ID NO: 8-9 and SEQ ID NO: 10 levels are determined using primers with at least 90% identity with respect to SEQ ID NO: 11-12; and/or (b) determining by quantitative PCR from said human feces sample the levels of at least two 16S rDNA bacterial sequences selected from the group consisting of SEQ ID NO: 1, SEQ ID NO: 4, SEQ ID NO: 7 and SEQ ID NO: 10 as recited in step a), and determining at least one of the ratios selected from the group consisting of SEQ ID NO: 10/SEQ ID NO: 4, SEQ ID NO: 7/SEQ ID NO: 4, SEQ ID NO: 4/SEQ ID NO: 1, SEQ ID NO: 7/SEQ ID NO: 1; SEQ ID NO:7/SEQ ID NO:10 and SEQ ID NO: 10/SEQ ID 1.

In one preferred embodiment, the method of screening for CRC and/or adenomatous polyps from a human feces sample of the invention, comprises:

(a) determining by quantitative PCR from said human feces sample the concentration of at least one 16S rDNA bacterial sequences selected from the group consisting of SEQ ID NO: 1, SEQ ID NO: 4, SEQ ID NO: 7 and SEQ ID NO: 10, wherein SEQ ID NO: 1 concentration is determined using primers with at least 90% identity with respect to SEQ ID NO: 2-13, SEQ ID NO: 4 concentration is determined using primers with at least 90% identity with respect to SEQ ID NO: 5-6, SEQ ID NO: 7 concentration is determined using primers with at least 90% identity with respect to SEQ ID NO: 8-9 and SEQ ID NO: 10 concentration is determined using primers with at least 90% identity with respect to SEQ ID NO: 11-12, (b) optionally, determining by quantitative PCR from said human feces sample the levels of at least two 16S rDNA bacterial sequences selected from the group consisting of SEQ ID NO: 1, SEQ ID NO: 4, SEQ ID NO: 7 and SEQ ID NO: 10 as recited in step a), and determining at least one of the ratios of concentrations selected from the group consisting of SEQ ID NO: 10/SEQ ID NO: 4, SEQ ID NO: 7/SEQ ID NO: 4, SEQ ID NO: 4/SEQ ID NO: 1, SEQ ID NO: 7/SEQ ID NO: 1; SEQ ID NO:7/SEQ ID NO:10 and SEQ ID NO: 10/SEQ ID 1 and (c) diagnosing, determining risk or determining recurrence of CRC and/or adenomatous polyps from the concentration of at least one of the sequences of step (a) and/or the value of at least one ratio obtained in step (b).

In another embodiment of the method of the invention, said primers with at least 90% identity with respect to SEQ ID NO: 2-13 are primers with at least 95% identity with respect to SEQ ID NO: 2-13, said primers with at least 90% identity with respect to SEQ ID NO: 5-6 are primers with at least 95% identity with respect to SEQ ID NO: 5-6, said primers with at least 90% identity with respect to SEQ ID NO: 8-9 are primers with at least 95% identity with respect to SEQ ID NO: 8-9 and said primers with at least 90% identity with respect to SEQ ID NO: 11-12 are primers with at least 95% identity with respect to SEQ ID NO: 11-12.

In a particularly preferred embodiment, said primers with at least 95% identity with respect to SEQ ID NO: 2-13 are primers identified by SEQ ID NO: 2-13, said primers with at least 95% identity with respect to SEQ ID NO: 5-6 are primers identified by SEQ ID NO: 5-6, said primers with at least 95% identity with respect to SEQ ID NO: 8-9 are primers identified by SEQ ID NO: 8-9 and said primers with at least 95% identity with respect to SEQ ID NO: 11-12 are primers identified by SEQ ID NO: 11-12.

In the present application, a problem sequence has 95% identity with respect to a determined sequence if 95% of residues of the problem sequence are identical to the residues of the determined sequence.

In a preferred embodiment, the method of the present invention is a method for diagnosis of colorectal cancer and colorectal cancer is diagnosed in step (c) if the Ct value of SEQ ID NO: 1 is above the cutoff Ct value of 37.2, or if the Ct value of SEQ ID NO: 4 is above the cutoff Ct value of 16.56, or if the Ct value of SEQ ID NO: 7 is above the cutoff Ct value of 22.97, or if the Ct value of SEQ ID NO: 10 is above the cutoff Ct value of 19.24, or if the value of the ratio SEQ ID NO: 10/SEQ ID NO: 4 is below the cutoff value of 1.16, or if the value of the ratio SEQ ID NO: 7/SEQ ID NO: 4 is below the cutoff value of 1.40, or if the value of the ratio SEQ ID NO: 4/SEQ ID NO: 1 is above the cutoff value of 0.44, or if the value of the ratio SEQ ID NO: 7/SEQ ID NO: 1 is above the cutoff value of 0.62, or if the value of the ratio and SEQ ID NO: 10/SEQ ID: 1 is above the cutoff value of 0.52, or if the SEQ ID NO: 10/SEQ ID: 7 is above the cutoff value of 1.2.

In another preferred embodiment, the method of the present invention is a method for diagnosing the risk of developing colorectal cancer, wherein a risk of developing colorectal cancer is diagnosed in step (c) if the Ct value of SEQ ID NO: I is above the cutoff Ct value of 36.45, or if the Ct value of SEQ ID NO: 4 is above the cutoff Ct value of 14.02, or if the Ct value of SEQ ID NO: 7 is above the cutoff Ct value of 24.76, or if the Ct value of SEQ ID NO: 10 is above the cutoff Ct value of 21.42, or if the value of the ratio SEQ ID NO: 10/SEQ ID NO: 4 is below the cutoff value of 1.56, or if the value of the ratio SEQ ID NO: 7/SEQ ID NO: 4 is below the cutoff value of 1.78, or if the value of the ratio SEQ ID NO: 4/SEQ ID NO: 1 is above the cutoff value of 0.38, or if the value of the ratio SEQ ID NO: 7/SEQ ID NO: 1 is above the cutoff value of 0.68, or if the value of the ratio and SEQ ID NO: 10/SEQ ID 1 is above the cutoff value of 0.59, or if the SEQ ID NO: 10/SEQ ID: 7 is above the cutoff value of 1.16.

In another embodiment, the method of the present invention further comprises detecting and/or quantifying one or more molecular biomarkers which are known to be indicative of CRC. Preferably, a multiple marker panel is used. Said multiple marker panel might comprise the determination of point mutations present in one or more of the following genes: APC, K-ras, BRAF, p53, NRAS, PIK3CA, CDK8, CMYC, CCNE1, CTNNBI, NEU (HER2), MYB, FBXW7, PTEN, SMAD4, SMAD2, SMAD3, TGFBIIR, TCF7L2, ACVR2 and BAX (Fearon, E. R., Annu. Rev. Pathol. Mech. Dis., 2011; 6:479-507). Other known CRC markers which might be determined are CpG island methylation, the quantity of human DNA per unit of stool weight, and the quantity of total DNA per unit of stool weight.

In a further embodiment, the method of the present invention further comprises storing the results of the determination in a computer readable medium. As used herein, "a computer readable medium" can be any apparatus that may include, store, communicate, propagate, or transport the results of the determination of the method of the invention. The medium can be an electronic, magnetic, optical, electromagnetic, infrared, or semiconductor system (or apparatus or device) or a propagation medium.

A second aspect, the invention relates to the use of at least one 16S rDNA bacterial sequence selected from the list consisting of SEQ ID NO:1, SEQ ID NO:4, SEQ ID NO:7 and SEQ ID NO:10 or the complementary rRNA sequence thereof as a biomarker for diagnosing, early detecting, determining recurrence, determining risk of developing, or predicting for CRC and/or polyps in a human subject; or determining whether a colonoscopy should be performed in said human subject; or determining prognosis wherein said human subject is a patient diagnosed with CRC and/or polyps; or guiding a therapy in a patient with CRC and/or polyps wherein said bacterial sequences are quantified from a feces sample of said human subject.

Preferably, said nucleic acid sequence is a 16S rDNA sequence selected from the list consisting of SEQ ID NO:1, SEQ ID NO:4, SEQ ID NO:7 and SEQ ID NO:10.

The term "biomarker" as used herein refers to markers of disease which are typically substances found in a bodily sample that can be easily measured. The measured amount can correlate to underlying disease pathophysiology, such as presence or absence of CRC and/or polyps, or probability of CRC and/or polyps in the future. In patients receiving treatment for their condition the measured amount will also correlate with responsiveness to therapy.

In a third aspect, the invention relates to a kit comprising:
a. a reagent selected from the group consisting of:
   i) nucleic acid probes capable of specifically hybridizing with at least one 16S rDNA sequence selected from the list consisting of SEQ ID NO:1, SEQ ID NO:4, SEQ ID NO:7 and SEQ ID NO:10 or the complementary rRNA sequence thereof; or
   ii) a pair of nucleic acid primers capable of specifically amplifying at least one 16S rDNA sequence selected from the list consisting of SEQ ID NO:1, SEQ ID NO:4, SEQ ID NO:7 and SEQ ID NO:10; and b. instructions for quantifying the levels of one or more of said sequences from a human feces sample according to a method of the present invention.

The term "probe" as used herein refers to synthetic or biologically produced nucleic acids, between 10 and 285 base pairs in length which contain specific nucleotide sequences that allow specific and preferential hybridization under predetermined conditions to target nucleic acid sequences, and optionally contain a moiety for detection or for enhancing assay performance. A minimum of ten nucleotides is generally necessary in order to statistically obtain specificity and to form stable hybridization products, and a maximum of 285 nucleotides generally represents an upper limit for length in which reaction parameters can be easily adjusted to determine mismatched sequences and preferential hybridization. Probes may optionally contain certain constituents that contribute to their proper or optimal functioning under certain assay conditions. For example, probes may be modified to improve their resistance to nuclease degradation (e.g., by end capping), to carry detection ligands (e.g., fluorescein) or to facilitate their capture onto a solid support (e.g., poly-deoxyadenosine "tails").

The term "primers" as used herein refers to oligonucleotides that can be used in an amplification method, such as a polymerase chain reaction ("PCR"), to amplify a nucleotide sequence. Primers are designed based on the polynucleotide sequence of a particular target sequence, e.g., one specific 16S rDNA sequence.

Design and validation of primers and probes is well known in the art. For quantitative real-time PCR methods, see for instance Rodriguez A et al. (Methods Mol Biol., 2015, 1275:31-56).

"Specific" as used herein means that a nucleotide sequence will hybridize to/amplify a predetermined target sequence and will not substantially hybridize to/amplify a non-target sequence under the assay conditions, generally stringent conditions are used.

"Hybridization" as used herein refers to a process by which, under predetermined reaction conditions, two partially or completely complementary strands of nucleic acid are allowed to come together in an antiparallel fashion to form a double-stranded nucleic acid with specific and stable hydrogen bonds, following explicit rules pertaining to which nucleic acid bases may pair with one another.

"Substantial hybridization" means that the amount of hybridization observed will be such that one observing the results would consider the result positive with respect to hybridization data in positive and negative controls. Data which is considered "background noise" is not substantial hybridization.

"Stringent hybridization conditions" means approximately 35 C to 65 C in a salt solution of approximately 0.9 molar NaCl. Stringency may also be governed by such reaction parameters as the concentration and type of ionic species present in the hybridization solution, the types and concentrations of denaturing agents present, and the temperature of hybridization. Generally as hybridization conditions become more stringent, longer probes are preferred if stable hybrids are to be formed. As a rule, the stringency of the conditions under which hybridization is to take place will dictate certain characteristics of the preferred probes to be employed.

Preferably, said nucleic acid sequence is a 16S rDNA sequence selected from the list consisting of SEQ ID NO:1, SEQ ID NO:4, SEQ ID NO:7 and SEQ ID NO:10.

In a particular embodiment, said kit is used for diagnosing, early detecting, determining recurrence, determining risk of developing, or predicting CRC and/or polyps in a human subject; or for determining whether a colonoscopy should be performed in said human subject; or for determining prognosis in a patient diagnosed with CRC and/or polyps; or for guiding a therapy in a patient with CRC and/or polyps. In a preferred embodiment, the kit may further comprise DNA extraction means, means for carrying out the hybridization and/or amplification, detection means, and/or one or more containers for collecting and/or holding the biological sample.

In a particular embodiment, the present invention relates to a kit for diagnosing colorectal cancer from a human feces sample comprising at least one pair of PCR primers selected from the pair of primers group consisting of SEQ ID NO: 2-13, SEQ ID NO: 5-6, SEQ ID NO: 8-9 and SEQ ID NO: 11-12.

In a forth aspect, the present invention relates to a nucleic acid sequence selected from the group consisting of SEQ ID NO: 2, SEQ ID NO: 13, SEQ ID NO: 5, SEQ ID NO: 6, SEQ ID NO: 8, SEQ ID NO: 9, SEQ ID NO: 11, and SEQ ID NO:12; or with at least 90% identity thereof, preferably with a 95% identity thereof, more preferably with 96%, 97%, 98%, 99% or 100% identity. Preferably, said sequences are used as primers in an amplification assay (such as qPCR) or as nucleic acid probes in an hybridization assay for the quantification of at least one 16S rDNA sequence selected from the list consisting of SEQ ID NO:1, SEQ ID NO:4, SEQ ID NO:7 and SEQ ID NO:10.

In a particular embodiment, said nucleic acid sequence is a pair of PCR primers selected from the group consisting of SEQ ID NO: 2-13, SEQ ID NO: 5-6, SEQ ID NO: 8-9 and SEQ ID NO: 11-12. In another particular embodiment, said nucleic acid sequence is as nucleic acid probe selected from the group consisting of SEQ ID NO: 2, SEQ ID NO: 13, SEQ ID NO: 5, SEQ ID NO: 6, SEQ ID NO: 8, SEQ ID NO: 9, SEQ ID NO: 11, and SEQ ID NO:12.

In a fifth aspect, the invention relates to the use of a nucleic acid sequence selected from the group consisting of SEQ ID NO: 2, SEQ ID NO: 13, SEQ ID NO: 5, SEQ ID NO: 6, SEQ ID NO: 8, SEQ ID NO: 9, SEQ ID NO: 11, and SEQ ID NO:12; or with at least 90% identity thereof in a method of screening of the invention, wherein SEQ ID NO: 2 and/or SEQ ID NO: 13 are used for the quantification of SEQ ID NO: 1; SEQ ID NO: 5 and/or SEQ ID NO: 6 are used for the quantification of SEQ ID NO: 4; SEQ ID NO: 8 and/or SEQ ID NO: 9 are used for the quantification of SEQ ID NO: 7; and SEQ ID NO: 11 and/or SEQ ID NO:12 are used for the quantification of SEQ ID NO: 10.

It will be understood that particular embodiments described in the Examples are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" may mean "one," but it is also consistent with the meaning of "one or more", "at least one," and "one or more than one."

Throughout this application, the term "about" means the indicated value ±5% of its value, preferably the indicated value ±2% of its value, most preferably the term "about" means exactly the indicated value (±0%).

EXAMPLES

Example 1.—Material and Methods

1. Biological Samples

Fecal samples were obtained from 27 patients recently diagnosed of a colorectal cancer (CRC) (phase 0-I), 24 patients Lynch syndrome carriers (L) and 19 healthy individuals (C). All patients had a colonoscopy at least 15 days before sample collection.

All of them signed up the corresponding informed consent. Exclusion criteria included antibiotic treatment within the 1 month before the study and age <18 years.

2. 16S rDNA Bacterial Sequences

B3, B10, B41, B46, B48 and B50 sequences correspond to denaturating gradient gel electrophoresis (DGGE) gel bands previously isolated from uncultured bacterium isolates.

16S rDNA bacterial sequence SEQ ID NO: 1 (B3), published in the EMBL-EBI European Nucleotide Archive (ENA) database under GQ411111.1;
  16S rDNA bacterial sequence SEQ ID NO: 4 (B10), published in the EMBL-EBI European Nucleotide Archive (ENA) database under GQ411118.1;
  16S rDNA bacterial sequence SEQ ID NO: 7 (B46), published in the EMBL-EBI European Nucleotide Archive (ENA) database under GQ411150.1;
  16S rDNA bacterial sequence SEQ ID NO: 10 (B48), published in the EMBL-EBI European Nucleotide Archive (ENA) database under GQ411152.1;
  16S rDNA bacterial sequence B41, published in the EMBL-EBI European Nucleotide Archive (ENA) database GQ411145.1; and
  16S rDNA bacterial sequence B50, published in the EMBL-EBI European Nucleotide Archive (ENA) database under GQ411154.1

3. Sample Collection, Preservation and Storage

Fecal samples from 24 h were collected in fecal container and storage at −20° C. for one month and transported to −80° C. freezer under conditions of ISO 9001.

4. Sample Processing and DNA Extraction

For fecal 16s-DNA extraction NucleoSpin® Soil. (Macherey-Nagel) was used.

Under bio class II safety conditions, 200 mg-500 mg of fecal sample were placed in Nucleospin bead-tube. 700 µl of SL1 and 150 µl of Enhancer SX were added to bead-tube.

5. Afterwards, DNA was Extracted and Purified Following the Instructions from the Manufacturer, and Eluted with 50 Ul of Elution Buffer or 10 mM Tris HCl pH=7.4

6. Calculation of DNA Concentration

DNA concentration of the extract was determined by fluorimetric analyses with the Qubit® 2.0 Fluorometer Catalog no Q32866 using the Quant-IT dsDNA Broad-Range Assay Kit. This method is highly selective for dsDNA with respect RNA and it provides an accurate quantification with in a range from 2 ng to 1,000 ng. With in this range fluorescence is linearly related to DNA concentration. DNA measurements were performed on 5 ul of the extract.

7. Quantitative Real-Time PCR (aPCR) of DNA Extracted from Fecal Samples

DNA from fecal samples was analysed by quantitative real-time PCR. In particular, we assessed the quantity of four bacterial populations per sample: B3, B10, B48 and B46. The bacterial sequences were quantified using a quantitative real time PCR with a fluorescent dsDNA stain. In this work we have used the pre-mix BRYT® from Promega (Madison, USA). Eubacteria were amplified following the procedure described by Furet. et al. (FEMS Microbiol Ecol., 2009; 68(3):351-62).

Bacterial abundances for each sample were expressed as Ct normalized to total DNA concentration.

The Ct (cyclethreshold) is defined as the number of q-PCR circles required for the fluorescent signal to cross the threshold. Ct levels are inversely proportional to the logarithm of target nucleic acid concentration in the sample (ie, the lower the Ct level the greater the amount of target nucleic acid in the sample). The real time assays undergo 40 cycles of amplification.

8. Methods of Statistical Analysis

Statistical normal distribution of the data was analysed through Test Kolmogorov—Smirnov.

According to whether there was an statistical normal distribution of the data or not, an adequate statistical test to compare the following groups was used.

Analyzed groups were: CRC vs healthy; CRC vs Lynch vs healthy; CRC+Lynch vs healthy; and CRC vs Lynch-high risk vs Lynch-low risk vs healthy.

For these groups, analysed variables were:
Four bacterial sequences quantification expressed in Ct;
Ratio of four bacterial sequences quantification;
Weight; and
DNA concentration.

Using a binary regression and ROC analyses correlation of bacterial sequence(s) quantification between healthy and CRC condition and the risk (in outfit and separated in two risk condition) and the sensitivity and specificity of the test were determined.

No difference between groups was observed in DNA and weight. Eubacteria (Eub) amount was found to be different between Lynch and CRC+Lynch and healthy donors (C), but it was considered normal because the condition of the disease implies a change of the phylogenetic core, which includes bacteria with less number of DNA copies. It does not imply a decrease of total bacteria (see for instance, Sobhani et al., PLoS One, 2011, 27; 6(1):e16393). For this reason, Eub quantification was not used as internal reference for normalization purposes.

Example 2. Primer Design and Validation

Primer for the quantification of the bacterial markers B3, B10, B46, B48, B41 and B50 in biopsy were designed from the comparative analysis with sequences previously obtained from phylogenetic groups using bioinformatics tools: ClustalX from European Bioinformatics Institute (www.ebi.ac.uk), Netprimer (Premier Biosoft) and PrimerExpress (Life Tecnologies—Thermo Fischer).

The detection system chosen was SybrGreen®. Set of primers with less than 3 positions different with respect to groups nearby were discarded. Set of primers with Tm values in dissociation curves different of expected ones were also discarded. Primer validation was done in biopsy sample and fecal sample. Dissociation curve was determined in order to analysis primer performance.

In FIGS. 8a to 13b are shown the amplification plots and dissociation curves for the validation of the designed primers for the amplification of B3, B10, B46, B48, B41 and B50, respectively. Primers showing an adequate dissociation curve (single peak for each primer set) were selected for the bacterial quantification of 16S rDNA in fecal samples. Notably, primers amplifying B3, B10, B46 and B48 were selected, these are specified in Table 9 below. B51 and B40 were discarded because of lack of specificity (multiple peaking for each primer set in melting curves).

TABLE 9

Primer pairs selected for qPCR amplification of 16S rDNA bacterial sequences B3, B10, B46 and B48 in fecal samples.

| | |
|---|---|
| B3 Forward (SEQ ID NO: 2) | GGAGGCCTTCGGGTCGTAA |
| B3 Reverse (SEQ ID NO: 13) | AGGTTCCGGGGGCTTCGG |
| B10 Forward (SEQ ID NO: 5) | CAACAAGGTAAGTGACGGC |
| B10 Reverse (SEQ ID NO: 6) | CGCCTACCTGTGCACTACTC |
| B46 Forward (SEQ ID NO: 8) | TCCACGTAAGTCACAAGCG |
| B46 Reverse (SEQ ID NO: 9) | CGCCTACCTGTGCACTACTC |
| B48 Forward (SEQ ID NO: 11) | GTACGGGGAGCAGCAGTG |
| B48 Reverse (SEQ ID NO: 12) | GACACTCTAGATGCACAGTTTCC |

Example 3: 16S rDNA Biomarkers Analysis in Colorectal Cancer Patients Vs Healthy Subjects A total of 16 samples of feces in 7 controls and 9 colorectal cancer patients have been analyzed. The quantification of each of the bacteria markers cited in Example 1 in feces samples analyzed is expressed in Ct values. The Ct (cyclethreshold) is defined as the number of q-PCR cycles required for the fluorescent signal to cross the threshold. Ct levels are inversely proportional to the logarithm of target nucleic acid concentration in the sample (ie, the lower the Ct level the greater the amount of target nucleic acid in the sample). The real time assays undergo 40 cycles of amplification. The obtained results are shown below, in Tables 1 and 2. Table 1 represents Ct absolute values and Table 2 represents Ct ratios. Two sample t-test was applied.

TABLE 1

Ct absolute values

| ID | Group | Condition | B48 | B46 | B10 | B3 |
|---|---|---|---|---|---|---|
| F10 | CRC | 1 | 18.59 | 22.78 | 16.33 | 33.64 |
| F11 | CRC | 1 | 20.33 | 26.45 | 20.37 | 41.57 |
| F3 | CRC | 1 | 23.52 | 26.2 | 19.8 | 38.45 |
| F4 | CRC | 1 | 16.41 | 20.87 | 14.88 | |
| F5 | CRC | 1 | 19.04 | 24 | 17.61 | 35.68 |
| F6 | CRC | 1 | 23.22 | 27.67 | 21.82 | |
| F16 | CRC | 1 | | 20.75 | 14.35 | |
| F7 | CRC | 1 | 23.19 | 28.2 | 22.34 | |
| F8 | CRC | 1 | 18.82 | 22.04 | 15.61 | |
| F12 | C | 0 | 17.55 | 20.9 | 14.95 | |
| F13 | C | 0 | 19.36 | 24.78 | 19.22 | |
| F14 | C | 0 | 19.46 | 21.44 | 15.07 | 37.34 |
| F15 | C | 0 | 17.55 | 19.85 | 12.84 | 36.98 |
| F9 | C | 0 | 17.61 | 21.8 | 15.41 | 35.66 |
| F1 | C | 0 | 18.09 | 21.97 | 14.79 | 38.3 |
| F2 | C | 0 | 17.07 | 20.57 | 12.76 | |
| Mean | CRC | | 20.39 | 24.329 | 18.12 | 37.34 |
| | C | | 18.099 | 21.616 | 15.01 | 37.07 |
| Standard deviation | CRC | | 2.65 | 2.89 | 3.04 | 3.44 |
| | C | | 0.94 | 1.58 | 2.15 | 1.09 |
| P-value | CRC vs C | | 0.025 | 0.021 | 0.019 | 0.444 |
| Mid-point (cutoffvalues) | | | 19.244 | 22.972 | 16.56 | 37.2 |
| Sensitivity % | | | 66.67 | 83.33 | 83.33 | 50 |
| Specificity % | | | 55.56 | 60 | 60 | 50 |
| Accuracy* | | | 60 | 68.75 | 68.75 | 50 |

*Accuracy is determined as (TN + TP)/(TN + TP + FN + FP)

TABLE 2

Ct ratios

| ID | Group | Condition | B48/B10 | B10/B3 | B46/B10 | B46/B48 | B46/B3 | B48/B3 |
|---|---|---|---|---|---|---|---|---|
| F10 | CRC | 1 | 1.14 | 0.49 | 1.39 | 1.23 | 0.68 | 0.55 |
| F11 | CRC | 1 | 1 | 0.49 | 1.3 | 1.3 | 0.64 | 0.49 |
| F3 | CRC | 1 | 1.19 | 0.51 | 1.32 | 1.11 | 0.68 | 0.61 |
| F4 | CRC | 1 | 1.1 | | 1.4 | 1.27 | | |
| F5 | CRC | 1 | 1.08 | 0.49 | 1.36 | 1.26 | 0.67 | 0.53 |
| F6 | CRC | 1 | 1.06 | | 1.27 | 1.19 | | |
| F16 | CRC | 1 | | | 1.45 | | | |
| F7 | CRC | 1 | 1.04 | | 1.26 | 1.22 | | |
| F8 | CRC | 1 | 1.21 | | 1.41 | 1.17 | | |
| F12 | C | 0 | 1.17 | | 1.4 | 1.19 | | |
| F13 | C | 0 | 1.01 | | 1.29 | 1.28 | | |
| F14 | C | 0 | 1.29 | 0.4 | 1.42 | 1.1 | 0.57 | 0.52 |
| F15 | C | 0 | 1.37 | 0.35 | 1.55 | 1.13 | 0.54 | 0.47 |

TABLE 2-continued

| | | | Ct ratios | | | | | |
|---|---|---|---|---|---|---|---|---|
| ID | Group | Condition | B48/B10 | B10/B3 | B46/B10 | B46/B48 | B46/B3 | B48/B3 |
| F9 | C | 0 | 1.14 | 0.43 | 1.41 | 1.24 | 0.61 | 0.49 |
| F1 | C | 0 | 1.22 | 0.39 | 1.49 | 1.21 | 0.57 | 0.47 |
| F2 | C | 0 | 1.34 | | 1.61 | 1.21 | | |
| Mean | | CRC | 1.1 | 0.5 | 1.35 | 1.22 | 0.67 | 0.55 |
| | | C | 1.22 | 0.39 | 1.45 | 1.19 | 0.57 | 0.49 |
| Standard deviation | | CRC | 0.07 | 0.01 | 0.07 | 0.06 | 0.02 | 0.05 |
| | | C | 0.13 | 0.04 | 0.11 | 0.06 | 0.03 | 0.02 |
| P-value | | CRC vs C | 0.02 | 0.001 | 0.018 | 0.224 | 0.001 | 0.045 |
| Mid-point (cutoffvalues) | | | 1.16123 | 0.4441 | 1.40243 | 1.20669 | 0.62 | 0.52 |
| Sensitivity % | | | 75 | 100 | 77.78 | 55.56 | 100.00 | 75.00 |
| Specificity % | | | 71.43 | 100 | 71.43 | 42.86 | 100.00 | 75.00 |
| Accuracy* | | | 73.33 | 100 | 75 | 50 | 100.00 | 75.00 |

*Accuracy is determined as (TN + TP)/(TN + TP + FN + FP)

The sensitivity and specificity of the diagnosis of colorectal cancer is 75 and 71% for the ratio SEQ ID NO: 10/SEQ ID NO: 4; 77% and 71%, respectively, for the ratio SEQ ID NO: 7/SEQ ID NO: 4; 100% and 100%, respectively, for the ratio SEQ ID NO: 4/SEQ ID NO: 1; 100% and 100%, respectively, for the ratio SEQ ID NO: 7/SEQ ID NO: 1; and 75% and 75%, respectively, for the ratio SEQ ID NO: 10/SEQ ID NO: 1.

Figure 2:
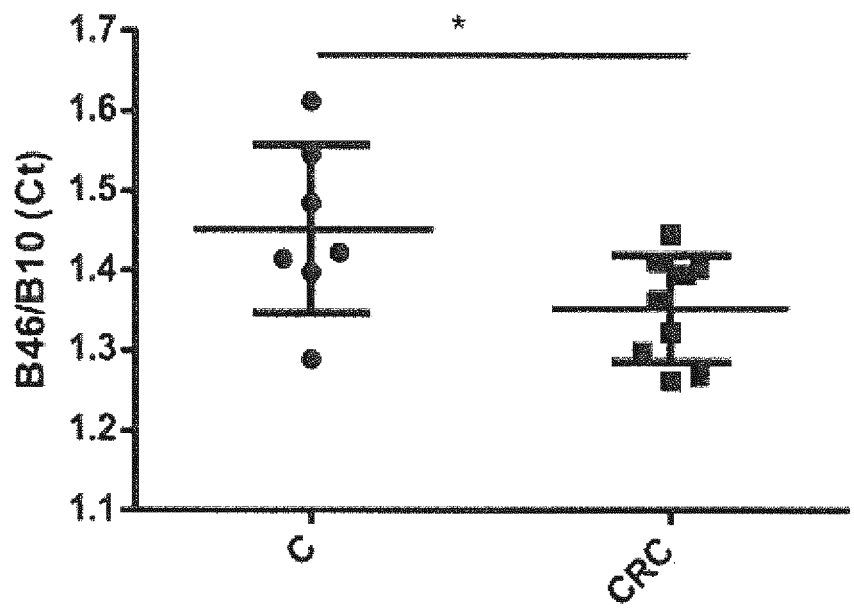
FIG. 2. Ratio of Ct values for 2 sequences: SEQ ID NO: 7/SEQ ID NO: 4. CRC represents the values obtained from feces samples of cancer colorectal patients, and C represents the control values obtained from healthy patients.
Figure 3:
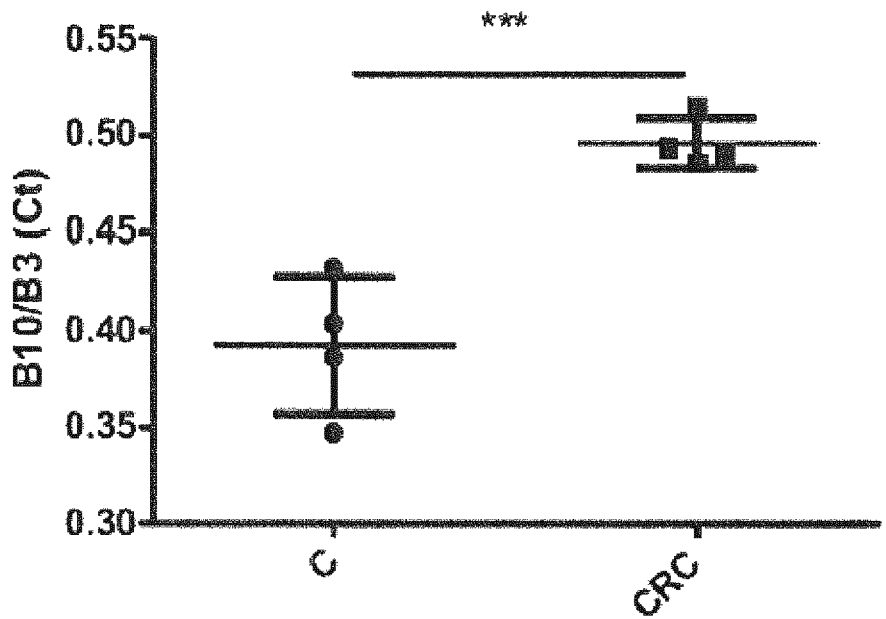
FIG. 3. Ratio of Ct values for 2 sequences: SEQ ID NO: 4/SEQ ID NO: 1. CRC represents the values obtained from feces samples of cancer colorectal patients, and C represents the control values obtained from healthy patients.

FIGS. 1, 2 and 3 are graphical representations of ratios of Ct values (SEQ ID NO: 10/SEQ ID NO: 4, SEQ ID NO: 7/SEQ ID NO: 4 and SEQ ID NO: 4/SEQ ID NO: 1).

Figure 4:
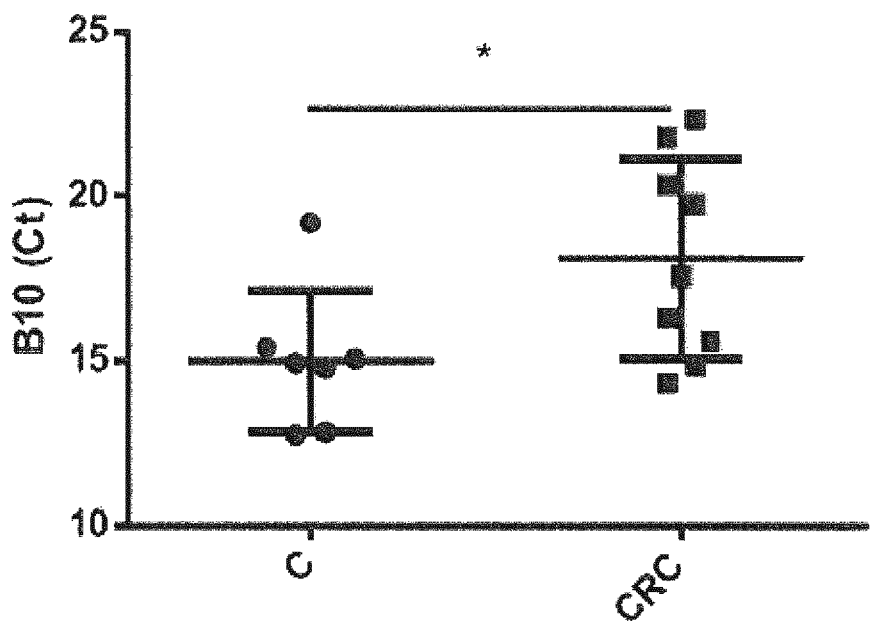
FIG. 4. Absolute Ct values for the sequence SEQ ID NO: 4. CRC represents the values obtained from feces samples of cancer colorectal patients, and C represents the control values obtained from healthy patients.
Figure 5:
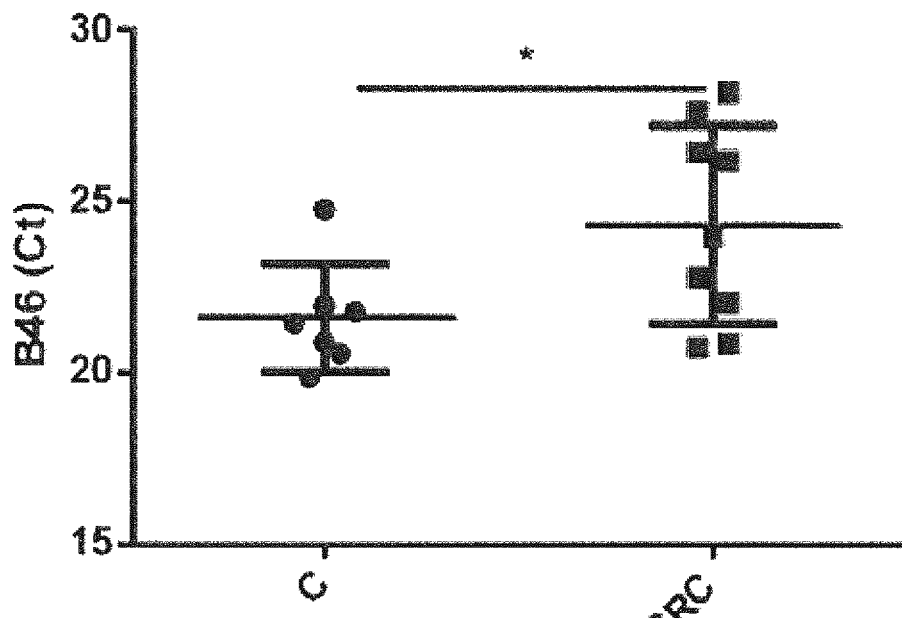
FIG. 5. Absolute Ct values for the sequence SEQ ID NO: 7. CRC represents the values obtained from feces samples of cancer colorectal patients, and C represents the control values obtained from healthy patients.

FIGS. 4 and 5 are graphical representations of the Ct absolutes (SEQ ID NO: 4, SEQ ID NO: 7).

Example 4. 16S rDNA Biomarkers Analysis in Lynch Syndrome Patients: CRC Vs High Risk (with Polyps) Vs Low Risk (Without Polyps)

The aim of this analysis is to determine the biomarkers predictive value for detecting colorectal cancer risk before clinical signs.

A total of 8 individuals with Lynch Syndrome (with genetic increased risk to develop colorectal cancer) were analyzed. All individuals had a colonoscopy, in the maximum period of one year, before the fecal sample collection. According to endoscopic exam 4 of them had had malign polyp (named as High Risk) and 4 had not any polyp (named as Low Risk).

The quantification of each of the bacteria markers cited in Example 1 in human feces samples analyzed were determined using the primers described in Example 2 and were quantified in Ct values.

The obtained results are shown below, in Tables 3 and 4. Table 3 represents Ct absolute values and Table 4 represents Ct ratios. Two sample t-test was applied.

TABLE 3

| | | | Ct absolute values | | | |
|---|---|---|---|---|---|---|
| ID | Group | Condition | B48 | B46 | B10 | B3 |
| F10 | CRC | 1 | 18.59 | 22.78 | 16.33 | 33.64 |
| F11 | CRC | 1 | 20.33 | 26.45 | 20.37 | 41.57 |
| F3 | CRC | 1 | 23.52 | 26.20 | 19.80 | 38.45 |
| F4 | CRC | 1 | 16.41 | 20.87 | 14.88 | |
| F5 | CRC | 1 | 19.04 | 24.00 | 17.61 | 35.68 |
| F6 | CRC | 1 | 23.22 | 27.67 | 21.82 | |
| F16 | CRC | 1 | | 20.75 | 14.35 | |
| F7 | CRC | 1 | 23.19 | 28.20 | 22.34 | |
| F8 | CRC | 1 | 18.82 | 22.04 | 15.61 | |
| MIL1 | High Risk | 2 | 22.58 | 25.87 | 14.56 | 35.56 |
| MIL2 | High Risk | 2 | 24.53 | 25.79 | 14.73 | 37.06 |
| MIL5 | High Risk | 2 | 22.56 | 24.57 | 14.16 | 38.44 |
| MIL4 | High Risk | 2 | 20.00 | 29.90 | 18.41 | 37.99 |
| MIL6 | LowRisk | 3 | 20.15 | 24.90 | 15.20 | 37.58 |
| MIL3 | LowRisk | 3 | 18.11 | 20.45 | 10.34 | 31.16 |
| MIL7 | LowRisk | 3 | 22.81 | 24.70 | 13.35 | 41.40 |
| MIL8 | LowRisk | 3 | 20.60 | 21.88 | 11.38 | 32.42 |
| Mean | | CRC | 20.39 | 24.33 | 18.12 | 37.34 |
| | | High Risk | 22.42 | 26.53 | 15.46 | 37.26 |
| | | LowRisk | 20.42 | 22.98 | 12.57 | 35.64 |
| Standard deviation | | CRC | 2.65 | 2.89 | 3.04 | 3.44 |
| | | High Risk | 1.86 | 2.32 | 1.98 | 1.27 |
| | | LowRisk | 1.93 | 2.18 | 2.15 | 4.74 |
| P-value | | CRC vs High Risk | 0.10 | 0.10 | 0.070 | 0.48 |
| | | CRC vs LowRisk | 0.49 | 0.21 | 0.004 | 0.29 |
| | | High Risk vs Low Risk | 0.09 | 0.03 | 0.047 | 0.27 |
| Mid-point (cut-off values) High Risk vs Low Risk | | | 21.42 | 24.76 | 14.02 | 36.45 |
| Sensitivity % High Risk vs Low Risk | | | 75.00 | 75.00 | 80.00 | 60.00 |
| Specificity % High Risk vs Low Risk | | | 75.00 | 75.00 | 100.00 | 66.67 |
| Accuracy High Risk vs Low Risk | | | 75.00 | 75.00 | 87.50 | 62.50 |

TABLE 4

| | | | Ct ratios | | | | | |
|---|---|---|---|---|---|---|---|---|
| ID | Group | Condition | B48/B10 | B10/B3 | B46/B10 | B46/B48 | B46/B3 | B48/B3 |
| F10 | CRC | 1 | 1.14 | 0.49 | 1.39 | 1.23 | 0.68 | 0.55 |
| F11 | CRC | 1 | 1.00 | 0.49 | 1.30 | 1.30 | 0.64 | 0.49 |
| F3 | CRC | 1 | 1.19 | 0.51 | 1.32 | 1.11 | 0.68 | 0.61 |
| F4 | CRC | 1 | 1.10 | | 1.40 | 1.27 | | |
| F5 | CRC | 1 | 1.08 | 0.49 | 1.36 | 1.26 | 0.67 | 0.53 |

TABLE 4-continued

Ct ratios

| ID | Group | Condition | B48/B10 | B10/B3 | B46/B10 | B46/B48 | B46/B3 | B48/B3 |
|---|---|---|---|---|---|---|---|---|
| F6 | CRC | 1 | 1.06 | | 1.27 | 1.19 | | |
| F16 | CRC | 1 | | | 1.45 | | | |
| F7 | CRC | 1 | 1.04 | | 1.26 | 1.22 | | |
| F8 | CRC | 1 | 1.21 | | 1.41 | 1.17 | | |
| MIL1 | High Risk | 2 | 1.55 | 0.41 | 1.78 | 1.15 | 0.73 | 0.63 |
| MIL2 | High Risk | 2 | 1.67 | 0.40 | 1.75 | 1.05 | 0.70 | 0.66 |
| MIL5 | High Risk | 2 | 1.59 | 0.37 | 1.74 | 1.09 | 0.64 | 0.59 |
| MIL4 | High Risk | 2 | 1.09 | 0.48 | 1.62 | 1.49 | 0.79 | 0.53 |
| MIL6 | LowRisk | 3 | 1.33 | 0.40 | 1.64 | 1.24 | 0.66 | 0.54 |
| MIL3 | LowRisk | 3 | 1.75 | 0.33 | 1.98 | 1.13 | 0.66 | 0.58 |
| MIL7 | LowRisk | 3 | 1.71 | 0.32 | 1.85 | 1.08 | 0.60 | 0.55 |
| MIL8 | LowRisk | 3 | 1.81 | 0.35 | 1.92 | 1.06 | 0.67 | 0.64 |
| Mean | | CRC | 1.10 | 0.50 | 1.35 | 1.22 | 0.67 | 0.55 |
| | | High Risk | 1.47 | 0.41 | 1.72 | 1.20 | 0.71 | 0.60 |
| | | LowRisk | 1.65 | 0.35 | 1.85 | 1.13 | 0.65 | 0.58 |
| Standard deviation | | CRC | 0.07 | 0.01 | 0.07 | 0.06 | 0.02 | 0.05 |
| | | High Risk | 0.26 | 0.05 | 0.07 | 0.20 | 0.06 | 0.06 |
| | | LowRisk | 0.22 | 0.04 | 0.15 | 0.08 | 0.03 | 0.04 |
| P-value | | CRC vs High Risk | 0.001491 | 0.009755 | 0.000001 | 0.38 | 0.11 | 0.10 |
| | | CRC vs LowRisk | 0.000029 | 0.000159 | 0.000002 | 0.02 | 0.19 | 0.21 |
| | | High Risk vs Low Risk | 0.172991 | 0.044382 | 0.087799 | 0.28 | 0.06 | 0.25 |
| Mid-point (cut-off values) High Risk vs Low Risk | | | 1.56 | 0.38 | 1.78 | 1.16 | 0.68 | 0.59 |
| Sensitivity % High Risk vs Low Risk | | | 66.67 | 75.00 | 80.00 | 50.00 | 75.00 | 75.00 |
| Specificity % High Risk vs Low Risk | | | 60.00 | 75.00 | 100.00 | 50.00 | 75.00 | 75.00 |
| AccuracyHigh Risk vs Low Risk | | | 62.50 | 75.00 | 87.50 | 50.00 | 75.00 | 75.00 |

The microbiological ratio markers were able to discern the group of individuals with High Risk to develop colorectal cancer (patients with Lynch syndrome and polyps). The sensitivity and specificity in detecting the colorectal cancer high risk population were 80% and 100% for the SEQ ID NO: 4; 75% and 75%, respectively, for the ratio SEQ ID NO: 4/SEQ ID NO: 1; 80% and 100%, respectively, for the ratio SEQ ID NO: 7/SEQ ID NO: 4; 75% and 75%, respectively, for the ratio SEQ ID NO: 7/SEQ ID NO: 1; and 75% and 75% for the ratio SEQ ID NO: 10/SEQ ID NO: 1.

Figure 6:
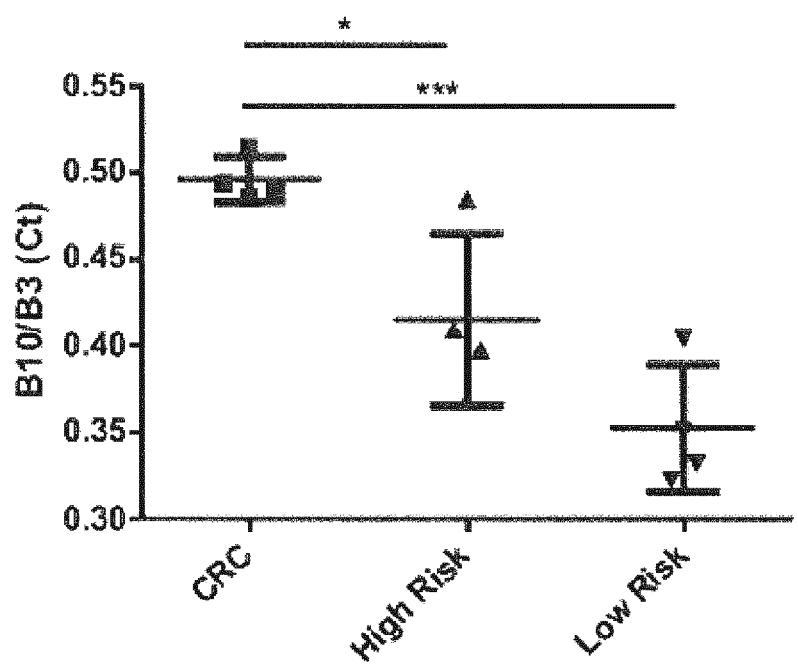
FIG. 6. Ratio Ct values for 2 sequences: SEQ ID NO: 4/SEQ ID NO: 1. CRC represents the values obtained from feces samples of cancer colorectal cancer, High Risk represents values obtained from individuals with Lynch syndrome who had polyps in his last colonoscopy and have an increased risk of developing colorectal cancer, Low Risk represents values obtained from individuals with Lynch syndrome who had no polyps in his last colonoscopy.
Figure 7:
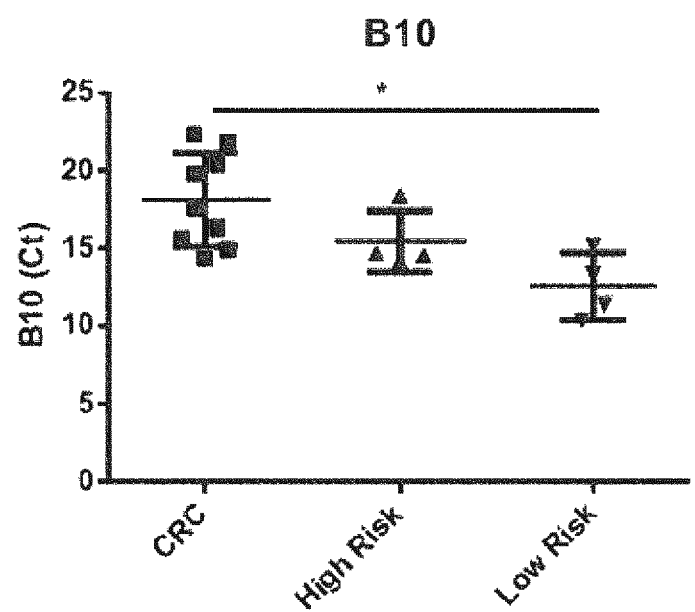
FIG. 7. Absolute Ct values for the sequence SEQ ID NO: 4. CRC represents the values obtained from feces samples of cancer colorectal cancer, High Risk represents values obtained from individuals with Lynch syndrome who had polyps in his last colonoscopy and have an increased risk of developing colorectal cancer, Low Risk represents values obtained from individuals with Lynch syndrome who had no polyps in his last colonoscopy.
Figure 8A:
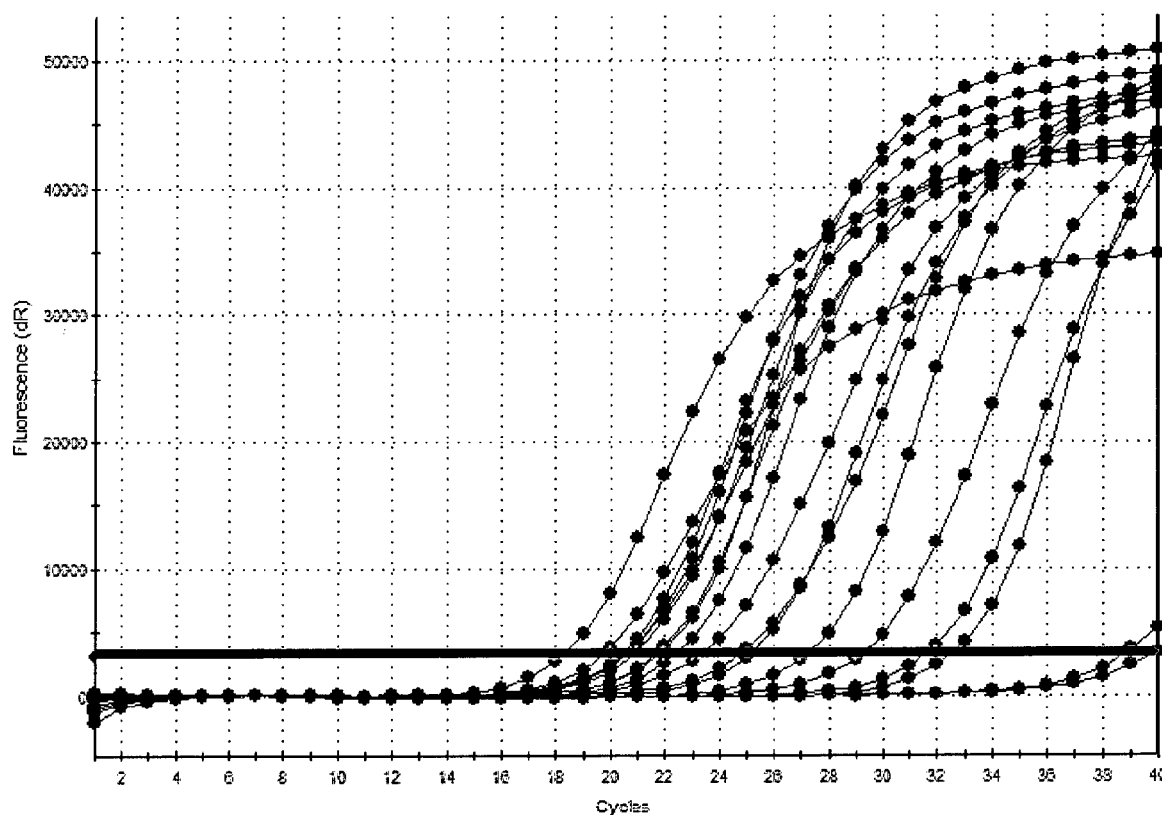
FIG. 8. Validation of primers for B3 amplification: Amplification plots (8a) and dissociation curve (8b).
Figure 8B:
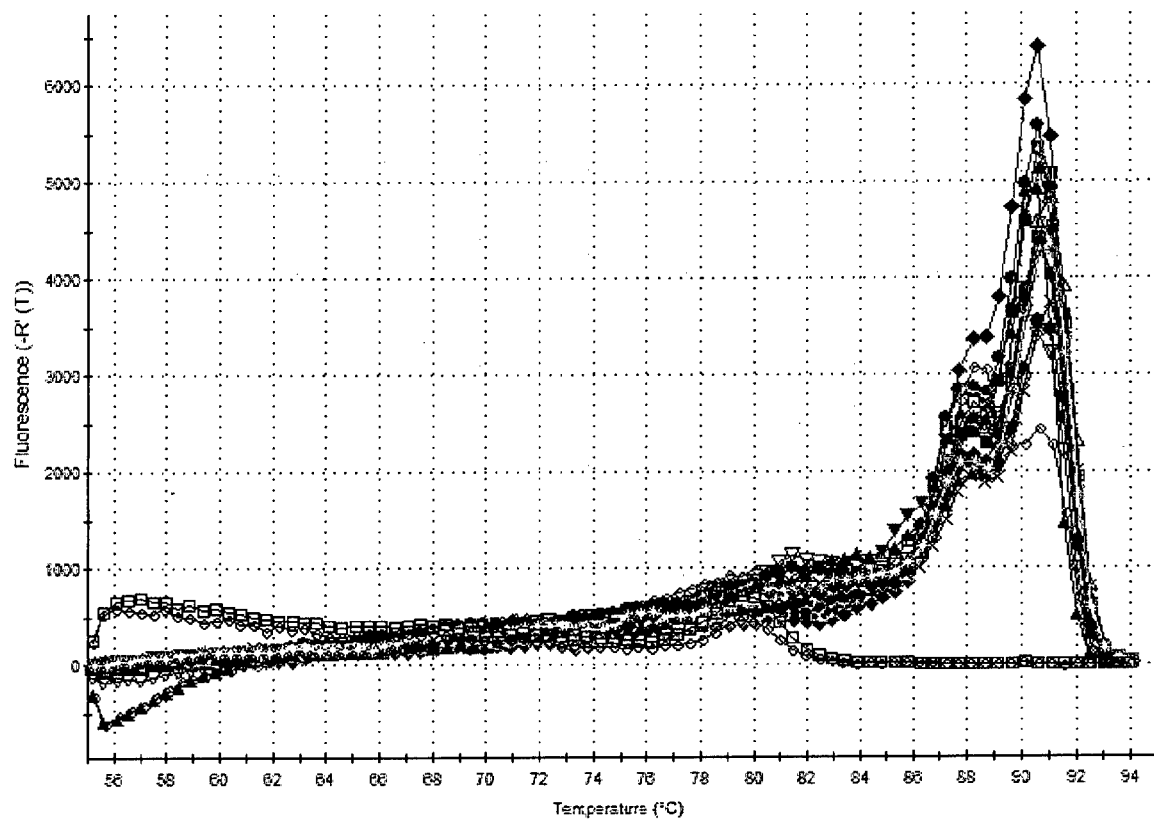
Figure 9A:
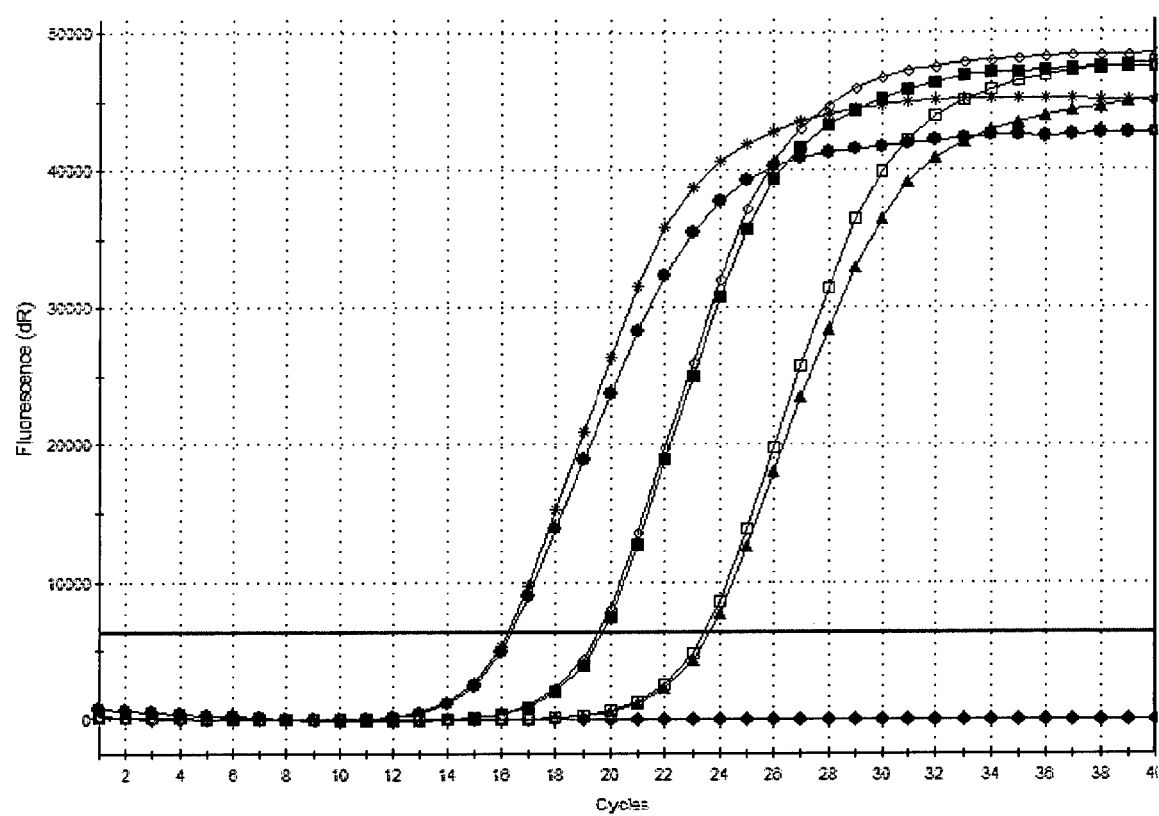
FIG. 9. Validation of primers for B10 amplification: Amplification plots (9a) and dissociation curve (9b).
Figure 9B:
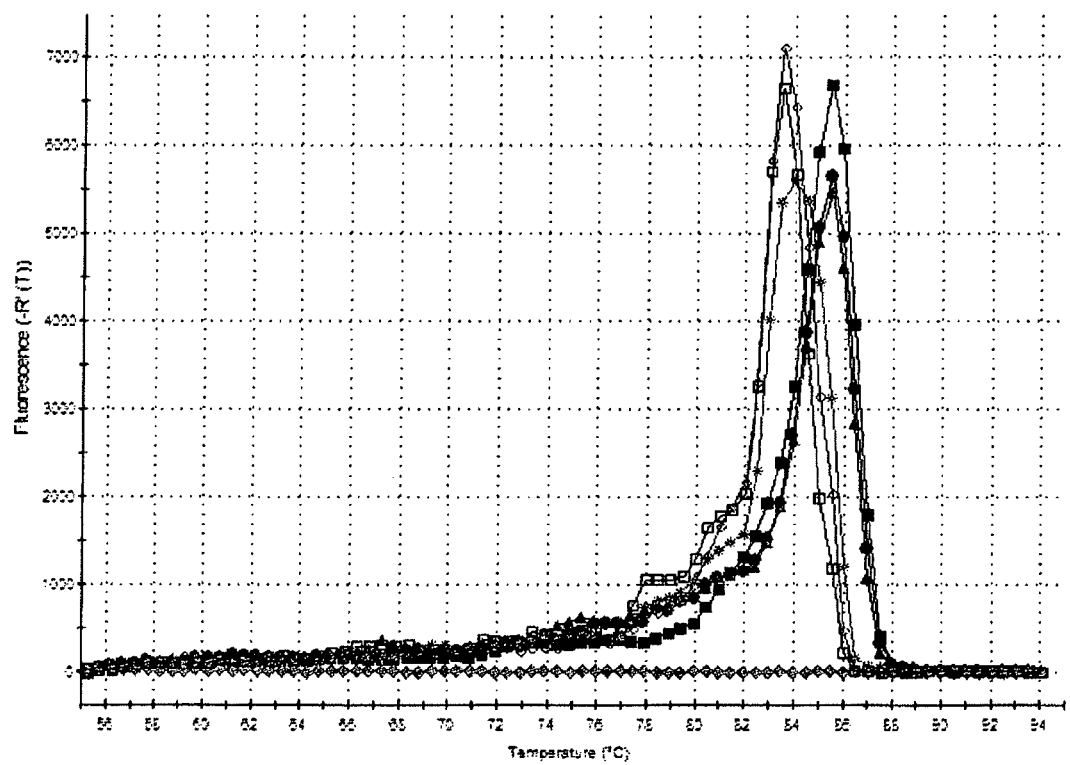
Figure 10A:
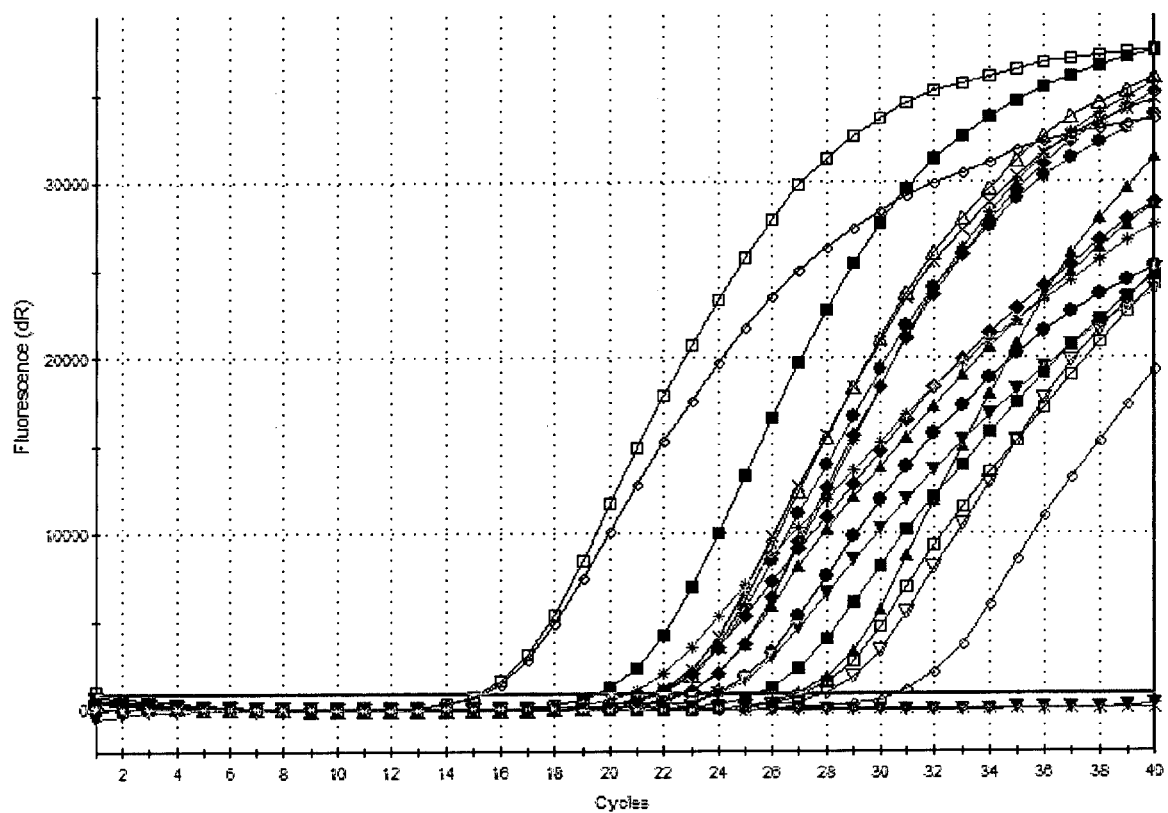
FIG. 10. Validation of primers for B41 amplification: Amplification plots (10a) and dissociation curve (10b).
Figure 10B:
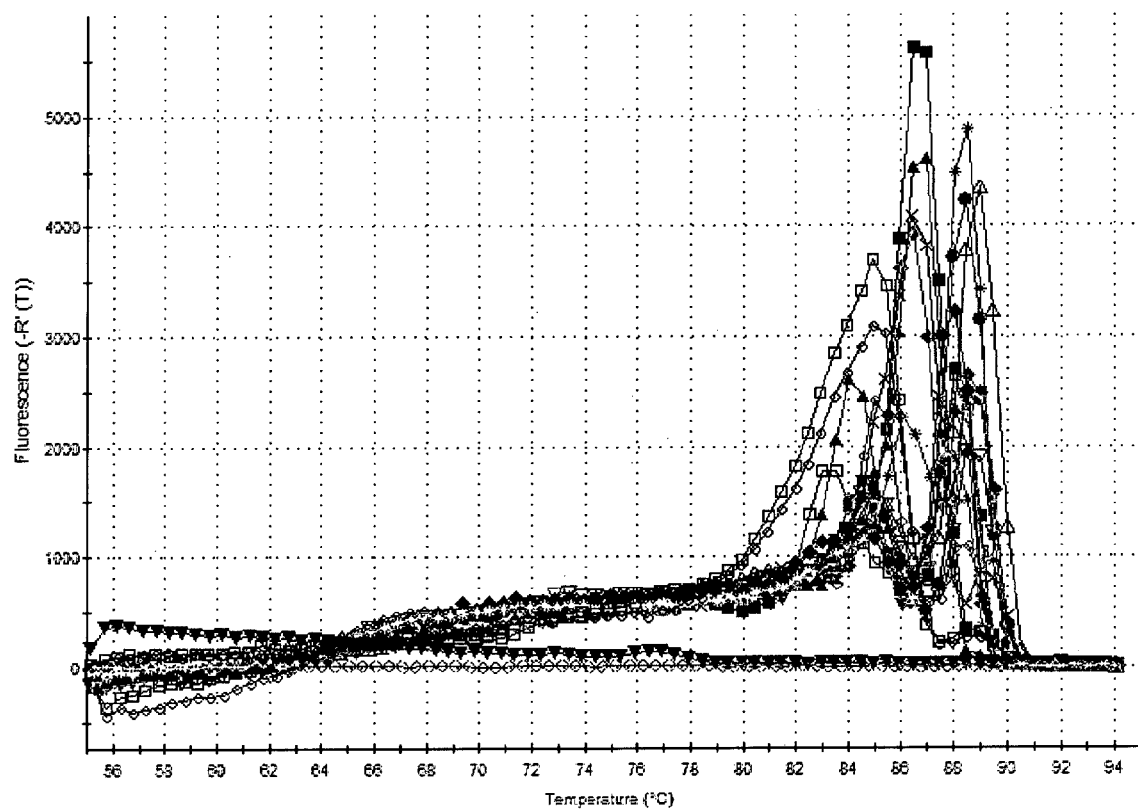
Figure 11A:
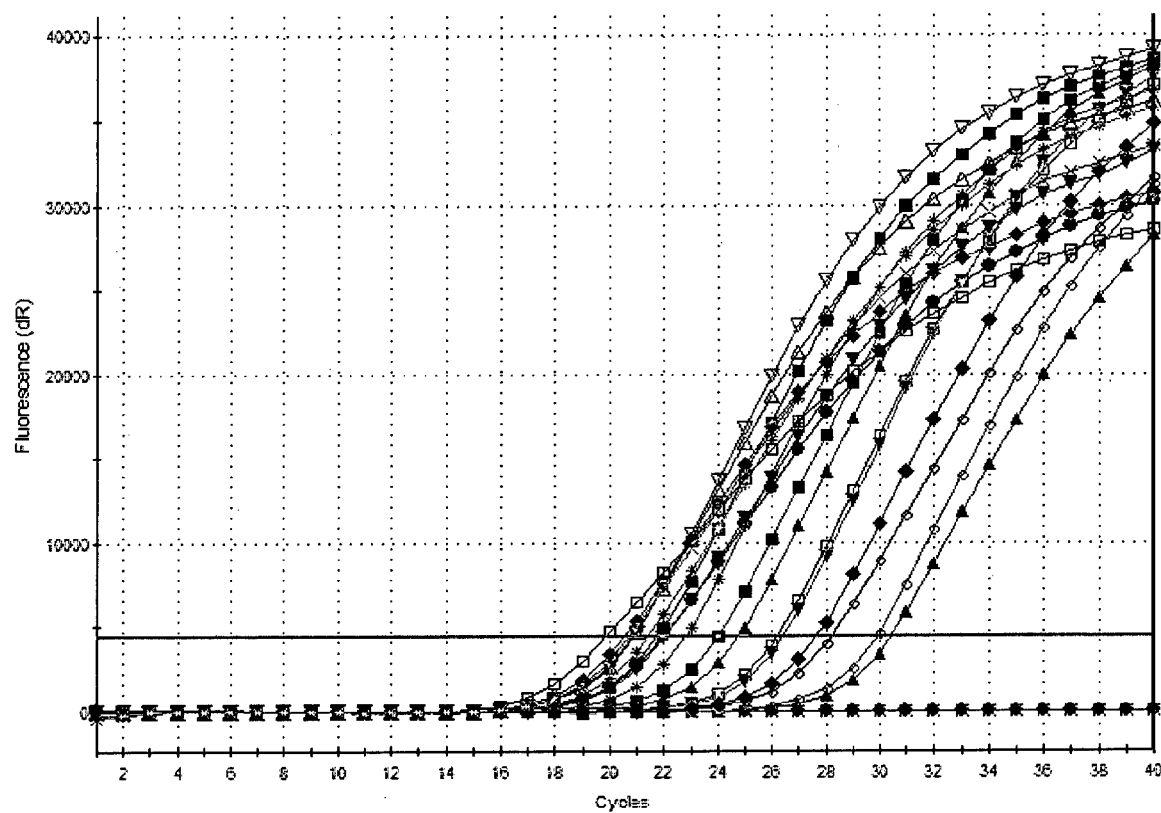
FIG. 11. Validation of primers for B46 amplification: Amplification plots (11a) and dissociation curve (11b).
Figure 11B:
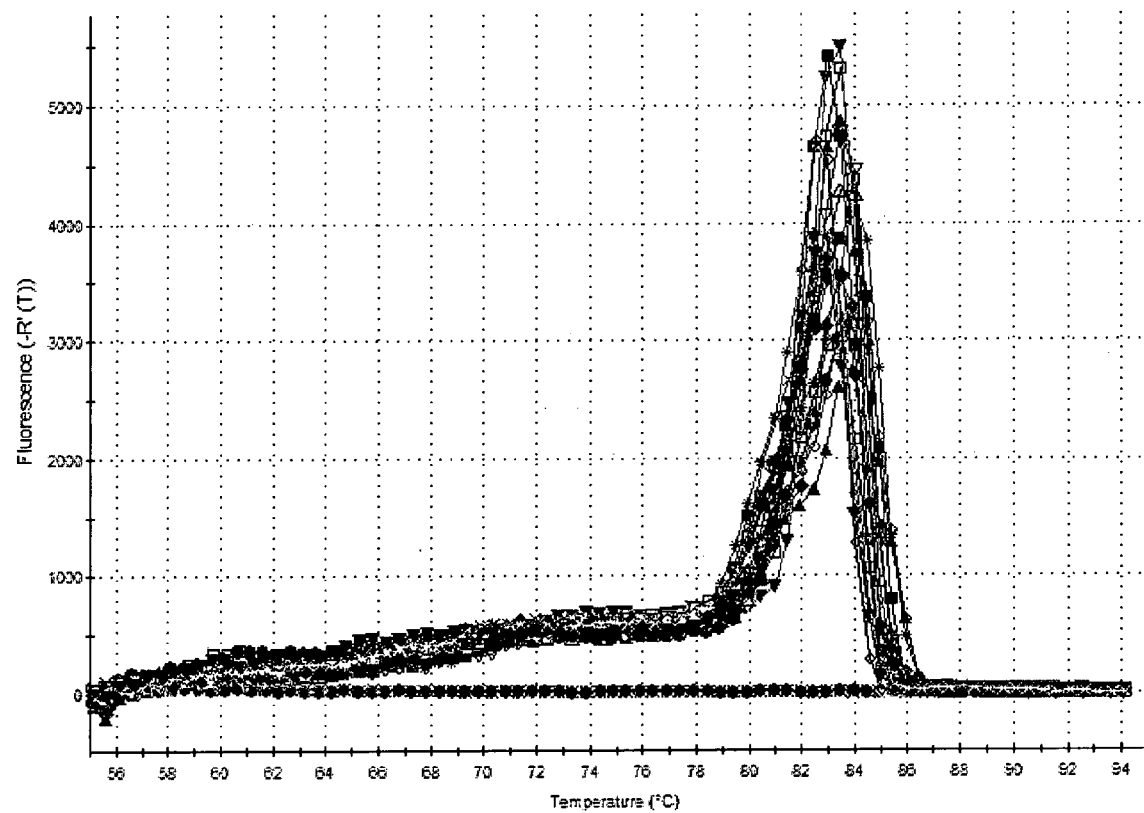
Figure 12A:
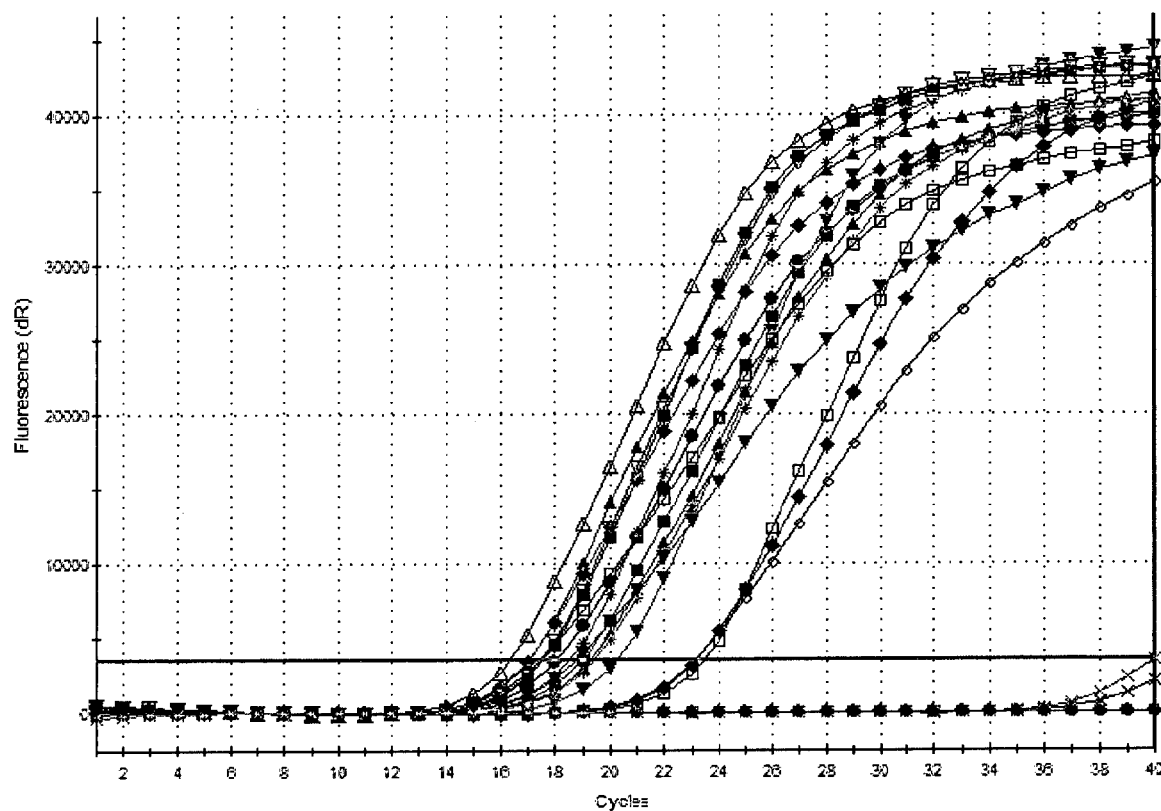
FIG. 12. Validation of primers for B48 amplification: Amplification plots (12a) and dissociation curve (12b).
Figure 12B:
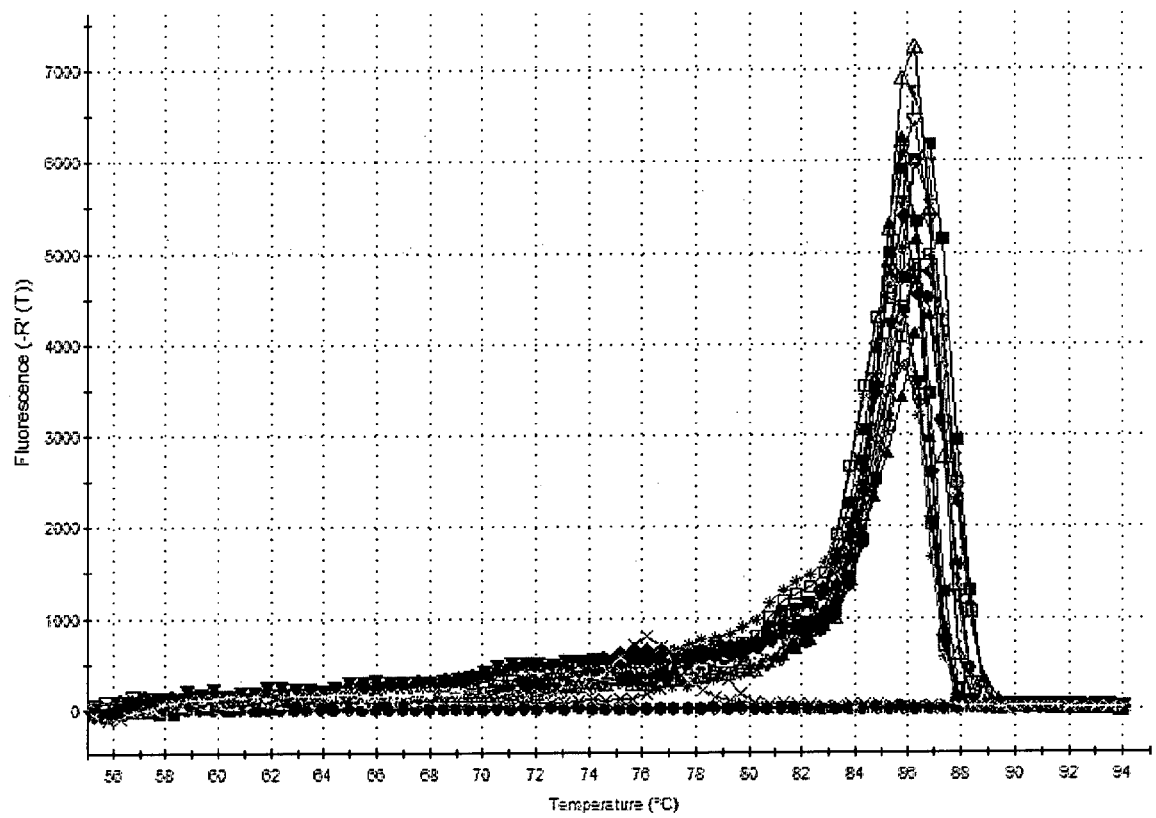
Figure 13A:
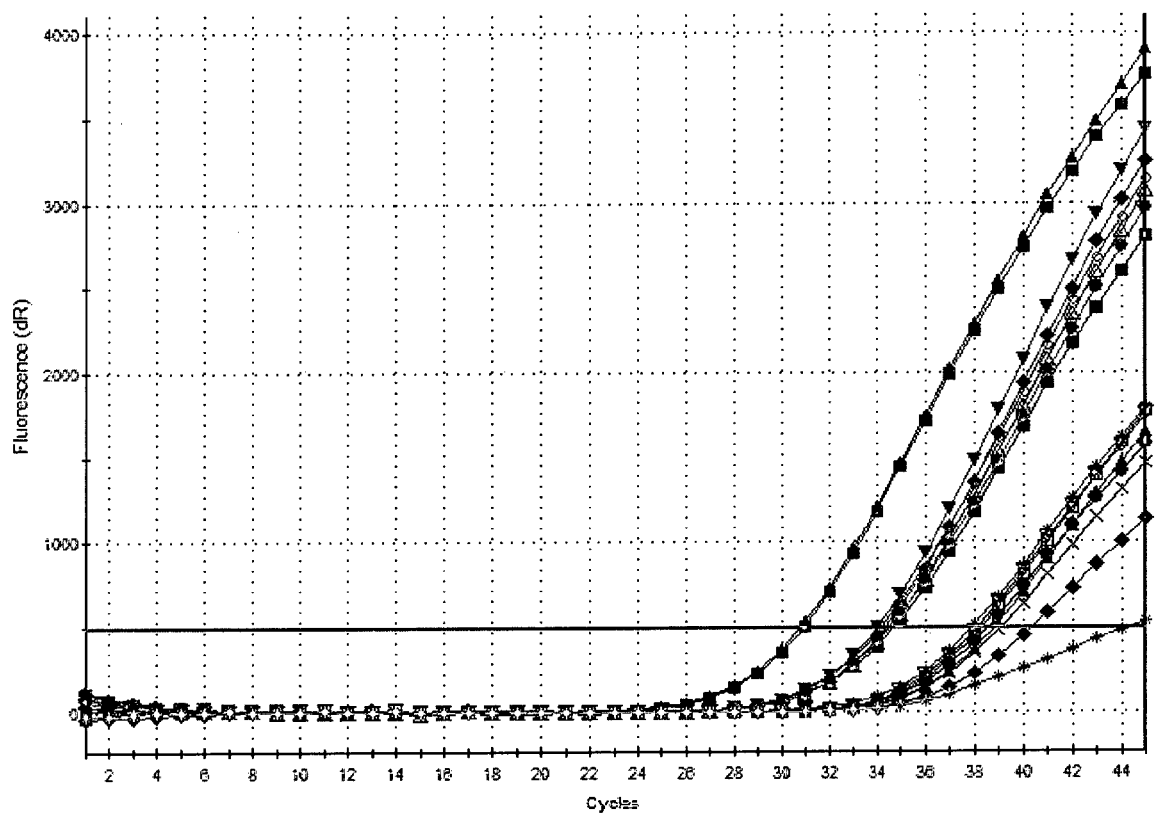
FIG. 13. Validation of primers for B50 amplification: Amplification plots (13a) and dissociation curve (13b).
Figure 13B:
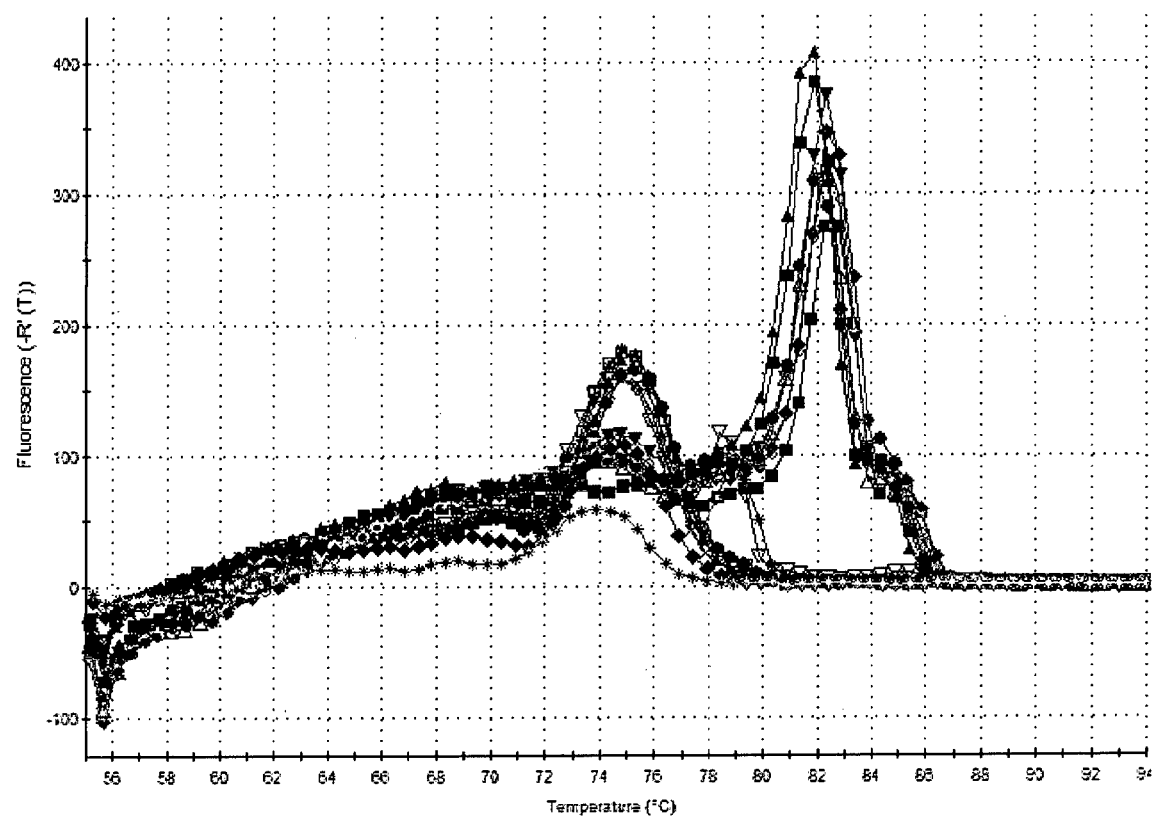

FIG. 6 is graphical representation of ratio of Ct values (SEQ ID NO: 4/SEQ ID NO: 1) and FIG. 7 is a graphical representation of the Ct absolutes (SEQ ID NO: 4).

Example 5: 16S rDNA Biomarkers Analysis in Colorectal Cancer Patients Vs Healthy Subjects Fecal sample were obtained from 27 patients recently diagnosed of a colorectal cancer (CRC) (phase 0-I), and healthy individuals (C). All patients had a colonoscopy at least 15 days before sample collection.

All of them signed up the corresponding informed consent. Exclusion criteria included antibiotic treatment within the 1 month before the study and age<18y.

In Table 5 (see below) is shown that quantification of the four bacterial sequences presented a significant increase in Ct in CRC patient feces. This fact means that there is a lower load of the four bacterial in this group.

The significant decreased load of these four bacteria might be a powerful tool to screening CRC patients. If we analyze the performance of the bacterial markers separately, we appreciate that best results were obtained with B3 which identified CRC patients with 94% specificity and 48% sensitivity and 0.7 of accuracy; and in second place, B46 with 84% specificity and 61.5% sensitivity and 0.698 of accuracy.

B48 and B10 also show an accuracy of 0.69 but 100% specificity and 36% sensitivity, and 57% specificity and 89.5% sensitivity, respectively.

The ratio between Ct of bacterial sequences quantification was calculated. Although, no statistical differences are observed we have to consider that applying this ratio in an increased sample might be an useful algorithm to complete screening of CRC. In this line, the combination of four sequences also must be considered to increase sensitivity and specificity of the test.

TABLE 5

Quantification of the 4 bacterial sequences in healthy individuals and CRC patients (expressed in Ct), statistical analysis through two sample t-test and ROC analysis.

| ID | Group | Condition | B3 | B48 | B10 | B46 |
|---|---|---|---|---|---|---|
| 4 | CRC | 1 | 29.86 | 20.84 | 14.18 | 21.34 |
| 5 | CRC | 1 | 24.3 | 15.88 | 10.34 | 17.53 |
| 6 | CRC | 1 | 27.33 | 20.66 | 15.77 | 23.13 |
| 7 | CRC | 1 | 24.88 | 19.06 | 13.64 | 20.69 |
| 8 | CRC | 1 | 20.61 | 17.78 | 12.92 | 19.7 |
| 11 | CRC | 1 | 27.28 | 25.69 | 17.05 | 24.35 |
| 12 | CRC | 1 | 29.04 | 22.58 | 16.49 | 23.17 |

TABLE 5-continued

Quantification of the 4 bacterial sequences in healthy individuals and CRC patients (expressed in Ct), statistical analysis through two sample t-test and ROC analysis.

| ID | Group | Condition | B3 | B48 | B10 | B46 |
|---|---|---|---|---|---|---|
| 13 | CRC | 1 | 21.98 | 17.52 | 10.97 | 17.34 |
| 14 | CRC | 1 | 27.07 | 19.94 | 13.52 | 19.9 |
| 15 | CRC | 1 | 28.57 | 26.60 | 19.77 | 27.53 |
| 24 | CRC | 1 | 26.77 | 22.64 | 17.84 | 23.83 |
| 25 | CRC | 1 | 21.64 | 17.01 | 11.54 | 18.7 |
| 27 | CRC | 1 | 26.52 | 20.97 | 15.49 | 22.63 |
| 31 | CRC | 1 | 29.91 | 18.92 | 16.44 | 23.8 |
| 35 | CRC | 1 | 23.37 | 18.81 | 12.24 | 18.77 |
| 36 | CRC | 1 | 22.87 | 17.28 | 12.74 | 19.76 |
| 38 | CRC | 1 |  | 16.36 | 24.43 | 30.7 |
| F10 | CRC | 1 | 20.49 | 18.59 | 16.33 | 22.78 |
| F16 | CRC | 1 | 18.24 |  | 14.35 | 20.75 |
| F11 | CRC | 1 | 29.19 | 20.33 | 20.37 | 26.45 |
| F3 | CRC | 1 | 32.48 | 23.52 | 19.80 | 26.20 |
| F4 | CRC | 1 | 21.76 | 16.41 | 14.88 | 20.87 |
| F5 | CRC | 1 | 20.56 | 19.04 | 17.61 | 24.00 |
| F6 | CRC | 1 | 31.6 | 23.22 | 21.82 | 27.67 |
| F7 | CRC | 1 | 27.14 | 23.19 | 22.34 | 28.20 |
| F8 | CRC | 1 | 22.37 | 18.82 | 15.61 | 22.04 |
| 43 | CRC | 1 | 30.9 | 22.46 | 17.12 | 25.57 |
| 16 | C | 0 | 22.97 | 20.21 | 15.54 | 23.12 |
| 17 | C | 0 | 20.4 | 15.84 | 10.71 | 17.54 |
| 18 | C | 0 | 22.05 | 15.72 | 12.06 | 17.67 |
| 23 | C | 0 | 21.79 | 17.16 | 12.59 | 18.89 |
| 28 | C | 0 | 20 | 18.86 | 15.29 | 21.33 |
| 30 | C | 0 | 26.61 | 20.47 | 12.78 | 20.26 |
| 32 | C | 0 | 22.76 | 15.07 | 15.95 | 23.09 |
| 33 | C | 0 | 23.66 | 18.30 | 13.54 | 19.57 |
| 34 | C | 0 | 22.01 | 17.73 | 14.29 | 19.07 |
| 37 | C | 0 | 24.06 | 19.60 | 14.47 | 19.65 |
| F1 | C | 0 | 24.71 | 18.09 | 14.79 | 21.97 |
| F12 | C | 0 | 20.79 | 17.55 | 14.95 | 20.90 |
| F13 | C | 0 | 25.1 | 19.36 | 19.22 | 24.78 |
| F14 | C | 0 | 21.63 | 19.46 | 15.07 | 21.44 |
| F2 | C | 0 | 20.42 | 17.07 | 12.76 | 20.57 |
| F15 | C | 0 | 19.69 | 17.55 | 12.84 | 19.85 |
| F9 | C | 0 | 23.29 | 17.61 | 15.41 | 21.80 |
| 39 | C | 0 |  | 18.03 | 11.95 | 18.97 |
| Mean | | CRC | 25.64346154 | 20.15846154 | 16.13222222 | 22.86666667 |
|  | | C | 22.46705882 | 17.98222222 | 14.12111111 | 20.58166667 |
| Standard Deviation | | CRC | 3.96679613 | 2.887129637 | 3.575465632 | 3.448853767 |
|  | | C | 1.948072011 | 1.514799756 | 1.957886432 | 1.927739456 |
| P-Value (two sample t-test) | | CRC vs C | 0.038 | 0.019 | 0.049 | 0.021 |
| CRC vs C | | Mid-Point | 26.69 | 20.90 | 15.75 | 22.0 |
|  | | AUC | 0.70 | 0.69 | 0.69 | 0.698 |
|  | | Sensitivity | 48% | 36% | 57% | 61.5% |
|  | | Specificity | 94% | 100% | 89.5% | 84% |

FIGS. 14 to 17 provide the graphical representation of absolute Ct values for B3, B10, B46 and B48, respectively, in CRC and healthy (C) groups.

Figure 27:
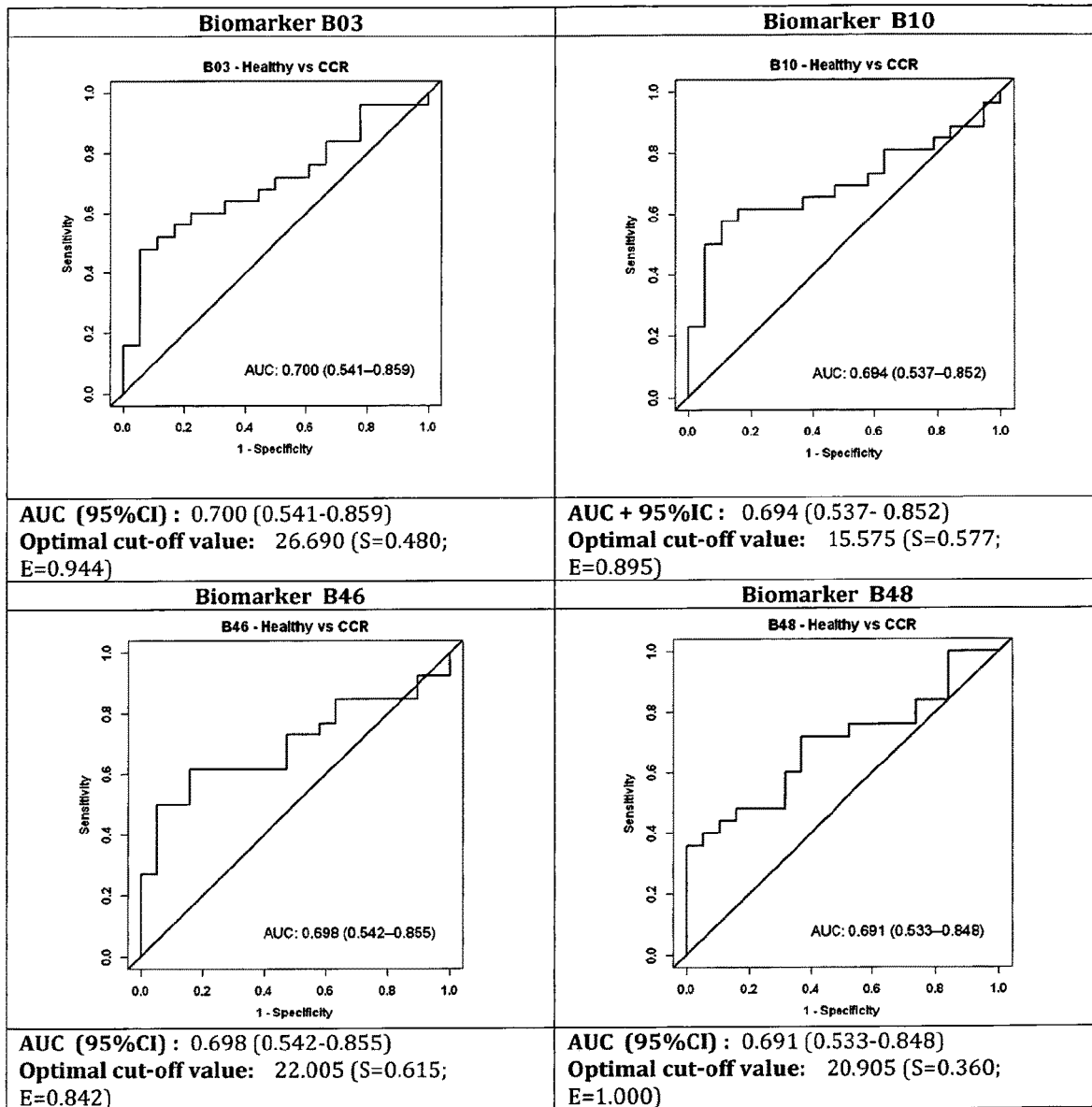
FIG. 27. ROC curves for B3, B10, B46 and B48 in healthy vs CRC analysis.

FIG. 27 provides the ROC curves for B3, B10, B46 and B48 in healthy vs CRC analysis.

Example 6: 16S rDNA Biomarkers Analysis CRC Vs Lynch (No Clinical Sign) Vs Healthy Individuals The aim of this analysis is to determine the biomarkers predictive value for detecting colorectal cancer risk before clinical signs.

Fecal sample were obtained from 27 patients recently diagnosed of a colorectal cancer (CRC) (phase 0-I), 24 patients Lynch syndrome carriers (L) and 19 healthy individuals (C). All patients had a colonoscopy at least 15 days before sample collection.

All of them signed up the corresponding informed consent. Exclusion criteria included antibiotic treatment within the 1 month before the study and age <18 years.

We quantified the four bacterial sequences in fecal samples of healthy individuals, CRC recently diagnosed patients and Lynch syndrome carriers. Lynch syndrome carriers are genetically predisposed to develop cancer, specifically colorectal cancer. This group is composed by individuals with no colorectal cancer neoplasm and no clinical sign, and it is considered as a colorectal cancer risk group.

We observed that Lynch syndrome group present a significantly increase of B3 and B48 Ct value compare to healthy patients groups. So, in Lynch group there is a lower load of B3 and B48 bacterial in feces sample.

Indeed, Lynch group does not show any statistical difference of bacterial sequences quantification compare to CRC except for B10. What implies that microbiological profile of Lynch group is similar to CRC although no clinical signs and neoplasm is observed in this group. This fact means that detection of one or more of these four bacterial sequences might be a potent tool to screen people with CRC risk and who might need colonoscopy exploration.

TABLE 6

Quantification of the 4 bacterial sequences in healthy individuals, CRC patients and syndrome Lynch carriers (expressed in Ct), statistical analysis through one-way ANOVA and ROC analysis.

| ID | Group | Condition | B3 | B48 | B10 | B46 |
|---|---|---|---|---|---|---|
| 4 | CRC | 1 | 29.86 | 20.84 | 14.18 | 21.34 |
| 5 | CRC | 1 | 24.3 | 15.88 | 10.34 | 17.53 |
| 6 | CRC | 1 | 27.33 | 20.66 | 15.77 | 23.13 |
| 7 | CRC | 1 | 24.88 | 19.06 | 13.64 | 20.69 |
| 8 | CRC | 1 | 20.61 | 17.78 | 12.92 | 19.7 |
| 11 | CRC | 1 | 27.28 | 25.69 | 17.05 | 24.35 |
| 12 | CRC | 1 | 29.04 | 22.58 | 16.49 | 23.17 |
| 13 | CRC | 1 | 21.98 | 17.52 | 10.97 | 17.34 |
| 14 | CRC | 1 | 27.07 | 19.94 | 13.52 | 19.9 |
| 15 | CRC | 1 | 28.57 | 26.60 | 19.77 | 27.53 |
| 24 | CRC | 1 | 26.77 | 22.64 | 17.84 | 23.83 |
| 25 | CRC | 1 | 21.64 | 17.01 | 11.54 | 18.7 |
| 27 | CRC | 1 | 26.52 | 20.97 | 15.49 | 22.63 |
| 31 | CRC | 1 | 29.91 | 18.92 | 16.44 | 23.8 |
| 35 | CRC | 1 | 23.37 | 18.81 | 12.24 | 18.77 |
| 36 | CRC | 1 | 22.87 | 17.28 | 12.74 | 19.76 |
| 38 | CRC | 1 |  | 16.36 | 24.43 | 30.7 |
| F10 | CRC | 1 | 20.49 | 18.59 | 16.33 | 22.78 |
| F16 | CRC | 1 | 18.24 |  | 14.35 | 20.75 |
| F11 | CRC | 1 | 29.19 | 20.33 | 20.37 | 26.45 |
| F3 | CRC | 1 | 32.48 | 23.52 | 19.80 | 26.20 |
| F4 | CRC | 1 | 21.76 | 16.41 | 14.88 | 20.87 |
| F5 | CRC | 1 | 20.56 | 19.04 | 17.61 | 24.00 |
| F6 | CRC | 1 | 31.6 | 23.22 | 21.82 | 27.67 |
| F7 | CRC | 1 | 27.14 | 23.19 | 22.34 | 28.20 |
| F8 | CRC | 1 | 22.37 | 18.82 | 15.61 | 22.04 |
| 43 | CRC | 1 | 30.9 | 22.46 | 17.12 | 25.57 |
| 16 | C | 0 | 22.97 | 20.21 | 15.54 | 23.12 |
| 17 | C | 0 | 20.4 | 15.84 | 10.71 | 17.54 |
| 18 | C | 0 | 22.05 | 15.72 | 12.06 | 17.67 |
| 23 | C | 0 | 21.79 | 17.16 | 12.59 | 18.89 |
| 28 | C | 0 | 20 | 18.86 | 15.29 | 21.33 |
| 30 | C | 0 | 26.61 | 20.47 | 12.78 | 20.26 |
| 32 | C | 0 | 22.76 | 15.07 | 15.95 | 23.09 |
| 33 | C | 0 | 23.66 | 18.30 | 13.54 | 19.57 |
| 34 | C | 0 | 22.01 | 17.73 | 14.29 | 19.07 |
| 37 | C | 0 | 24.06 | 19.60 | 14.47 | 19.65 |
| F1 | C | 0 | 24.71 | 18.09 | 14.79 | 21.97 |
| F12 | C | 0 | 20.79 | 17.55 | 14.95 | 20.90 |
| F13 | C | 0 | 25.1 | 19.36 | 19.22 | 24.78 |
| F14 | C | 0 | 21.63 | 19.46 | 15.07 | 21.44 |
| F2 | C | 0 | 20.42 | 17.07 | 12.76 | 20.57 |
| F15 | C | 0 | 19.69 | 17.55 | 12.84 | 19.85 |
| F9 | C | 0 | 23.29 | 17.61 | 15.41 | 21.80 |
| 39 | C | 0 |  | 18.03 | 11.95 | 18.97 |
| 1 | L | 2 | 23.08 | 18.76 | 12.03 | 19.21 |
| 2 | L | 2 | 26.58 | 18.47 | 13.60 | 21.02 |
| 3 | L | 2 | 23.51 | 19.36 | 10.85 | 18.33 |
| 9 | L | 2 |  | 16.94 | 12.89 | 19.77 |
| 10 | L | 2 | 19.91 | 17.68 | 10.44 | 17.84 |
| 19 | L | 2 | 32.81 | 21.60 | 15.72 | 21.67 |
| 20 | L | 2 | 19.9 | 19.77 | 17.81 | 24.2 |
| 21 | L | 2 | 19.66 | 17.05 | 13.55 | 19.7 |
| 22 | L | 2 | 21.28 | 16.04 | 10.22 | 17.48 |
| 26 | L | 2 | 19.57 | 20.73 | 11.79 | 19.36 |
| 29 | L | 2 | 23.67 | 17.92 | 11.30 | 18.2 |
| 40 | L | 2 | 29.14 | 23.47 | 19.42 | 26.3 |
| 41 | L | 2 | 32.14 | 20.18 | 17.27 | 23.72 |
| 42 | L | 2 | 35.19 | 18.34 | 19.63 | 27.07 |
| 44 | L | 2 | 28.83 | 23.16 | 16.15 | 23.42 |
| 45 | L | 2 | 24.79 | 16.85 | 10.84 | 19.02 |
| MIL1 | L | 2 | 37.1 | 22.60 | 14.69 | 25.52 |
| MIL2 | L | 2 | 32.74 | 24.60 | 14.63 | 25.53 |
| MIL3 | L | 2 | 27.80 | 18.00 | 10.34 | 20.28 |
| MIL4 | L | 2 | 29.09 | 20.00 | 18.17 | 29.66 |
| MIL5 | L | 2 | 33.45 | 22.60 |  | 24.81 |
| MIL6 | L | 2 | 31.69 | 20.20 | 14.66 | 24.54 |
| MIL7 | L | 2 | 35.88 | 22.90 | 13.05 | 24.59 |
| MIL8 | L | 2 | 26.2 | 20.60 | 10.85 | 21.87 |
| Mean |  | CRC | 25.64346154 | 20.15846154 | 16.13222222 | 22.86666667 |
|  |  | C | 22.46705882 | 17.98222222 | 14.12111111 | 20.58166667 |
|  |  | Lynch | 27.56585217 | 19.90916667 | 13.9076087 | 22.21291667 |
| Standard Deviation |  | CRC | 3.96679613 | 2.887129637 | 3.575465632 | 3.448853767 |
|  |  | C | 1.948072011 | 1.514799756 | 1.957886432 | 1.927739456 |

TABLE 6-continued

Quantification of the 4 bacterial sequences in healthy individuals,
CRC patients and syndrome Lynch carriers (expressed in Ct), statistical
analysis through one-way ANOVA and ROC analysis.

| ID | Group | Condition | B3 | B48 | B10 | B46 |
|---|---|---|---|---|---|---|
|  |  | Lynch | 5.628873475 | 2.403976627 | 3.02383331 | 3.369239985 |
|  | P-Value | CRC vs C | 0.038 | 0.019 | 0.049 | 0.021 |
|  | (one way ANOVA) | CRC vs L | 0.381 | 0.988 | 0.057 | 0.849 |
|  |  | L vs C | 0.004 | 0.018 | 0.989 | 0.163 |
|  | C vs L | Mid-Point | 25.65 | 19.69 | 11.87 | 23.27 |
|  |  | AUC | 0.73 | 0.746 | 0.55 | 0.629 |
|  |  | Sensitivity | 60.9 | 54.2 | 34.8 | 45.8 |
|  |  | Specificity | 88.9 | 94.1 | 94.7 | 94.7 |
|  | L vs CRC | Mid-Point | 31.65 | 19.21 | 14.78 | 21.95 |
|  |  | AUC | 0.60 | 0.487 | 0.69 | 0.55 |
|  |  | Sensitivity | 96 | 52 | 65.4 | 61.5 |
|  |  | Specificity | 34.8 | 58.3 | 69.6 | 54.2 |
|  | CRC vs C | Mid-Point | 26.69 | 20.90 | 15.75 | 22.0 |
|  |  | AUC | 0.70 | 0.69 | 0.69 | 0.698 |
|  |  | Sensitivity | 48% | 36% | 57% | 61.5% |
|  |  | Specificity | 94% | 100% | 89.5% | 84% |

FIGS. 18 to 21 provide the graphical representation of absolute Ct values in CRC, L and C groups of sequences SEQ ID NO: 1, SEQ ID NO: 4, SEQ ID NO: 7 and SEQ ID NO: 10, respectively.

Figure 28:
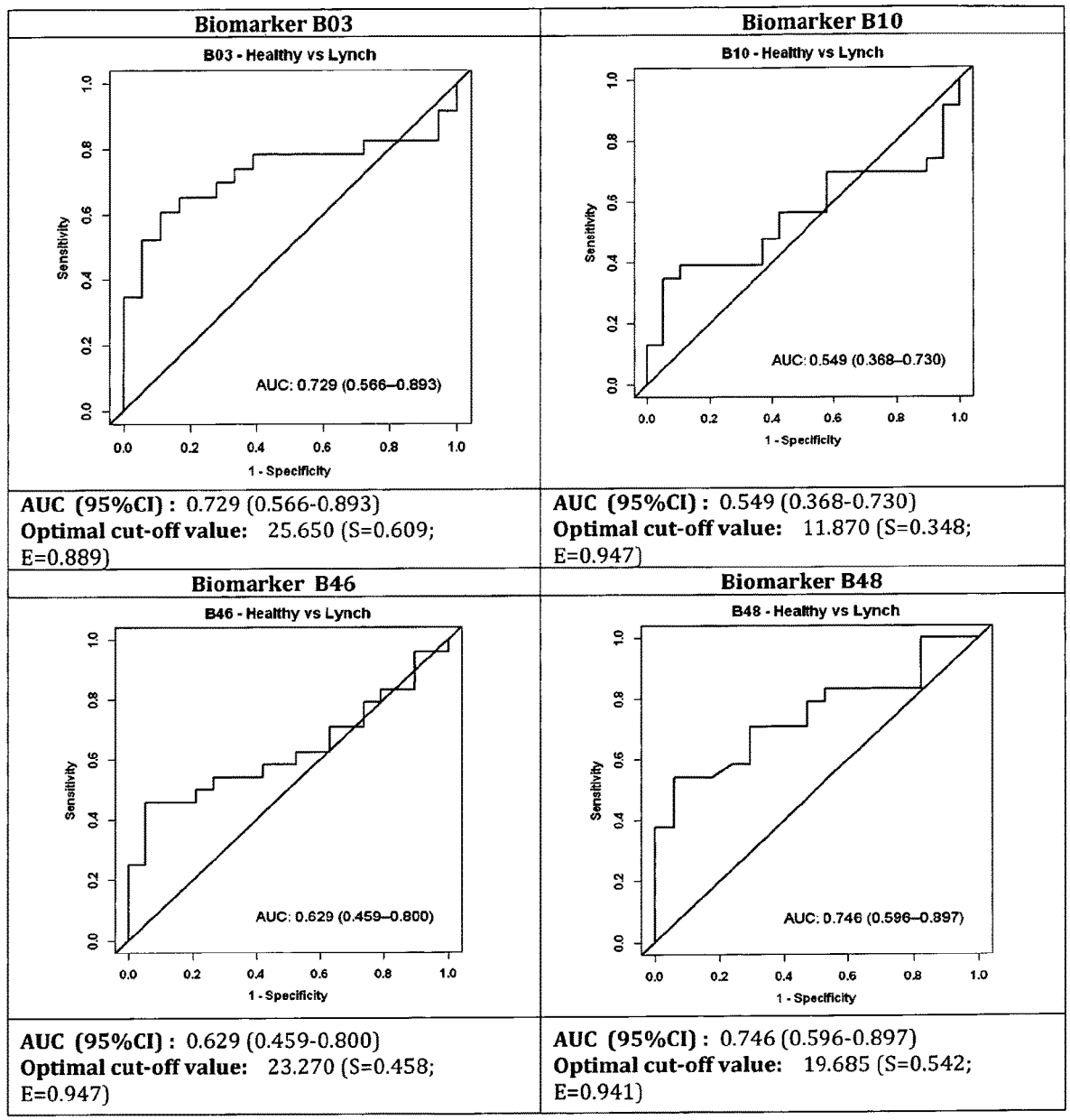
FIG. 28. ROC curves for B3, B10, B46 and B48 in healthy vs Lynch analysis.

FIG. 28 provides the ROC curves for B3, B10, B46 and B48 in healthy (C) vs Lynch (L) analysis.

Figure 30:
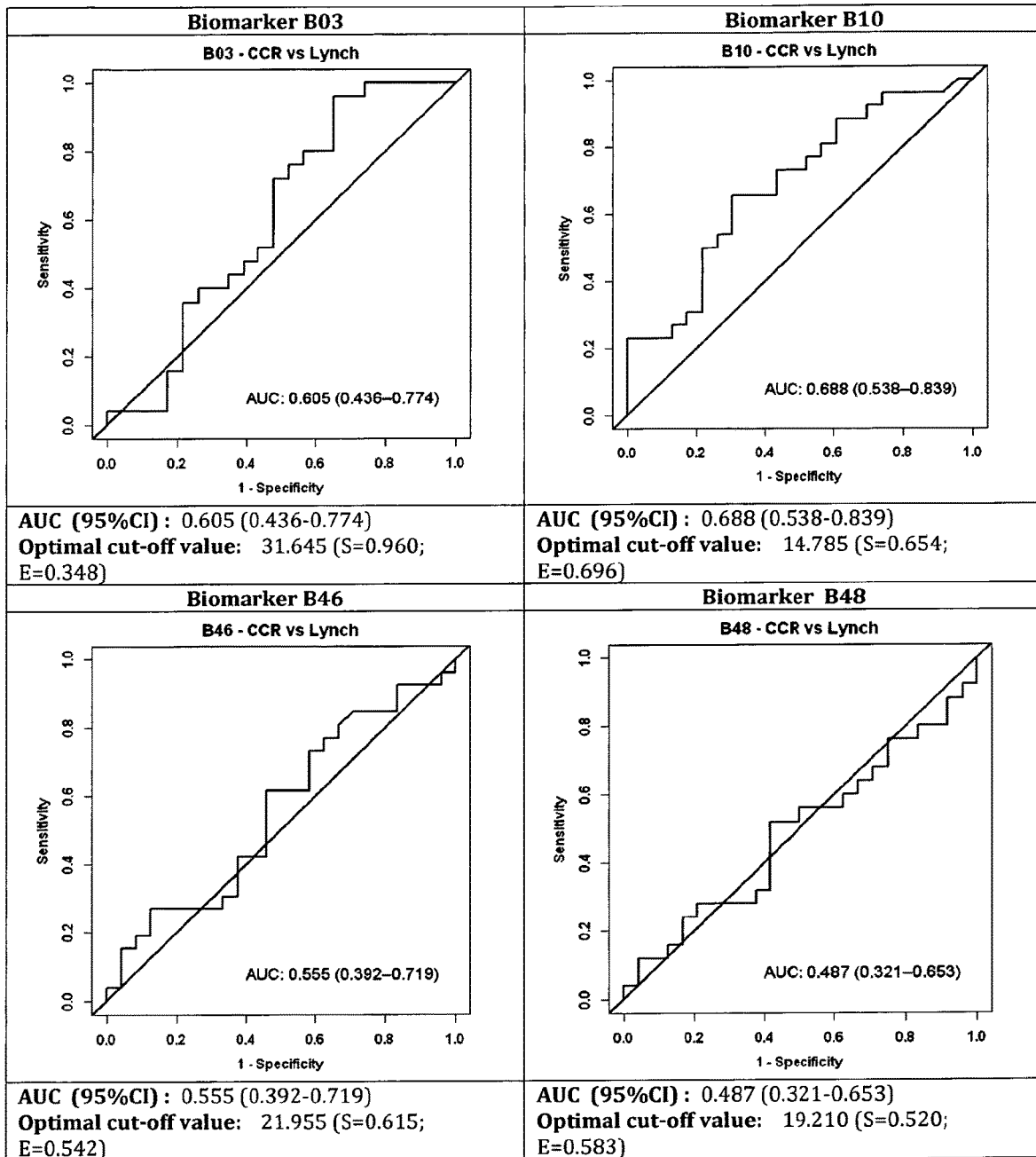
FIG. 30. ROC curves for B3, B10, B46 and B48 in CRC vs Lynch analysis.

FIG. 30 provides the ROC curves for B3, B10, B46 and B48 in CRC vs Lynch analysis.

Example 7: 16S rDNA Biomarkers Analysis CRC+Lynch Vs Healthy Individuals

According to example 6 analysis, Lynch syndrome carriers have a similar microbiological profile in feces to CRC patients. So, in this experiment we aim to test the potential of using quantification detection of the four bacterial sequences for screening colorectal cancer risk individuals in healthy individuals and colorectal cancer risk individuals (CRC+L), before colonoscopy exploration.

In Table 7, we have represented the quantification of bacterial sequences expressed in Ct.

We observe that B3, B48 and B46 significantly increase the Ct value in colorectal cancer risk group (CRC+L). So, level of these bacteria in feces is decreased.

B10 in CRC+L also present a lower level although no statistical differences are observed (p=0.137).

Evaluating the performance of bacterial quantification in detecting colorectal cancer, it is shown that B3 and B48 has the best accuracy (0.7) and, respectively, 56.2% sensitivity-88.9% specificity and 51% sensitivity-84% specificity.

In second place, B46 has an accuracy of 0.665 and 94.7% sensitivity-23.12% specificity. Finally, B10 has an accuracy of 0.58 and 44.9% sensitivity-89.5% specificity.

The ratio between Ct of bacterial sequences quantification was calculated. Although, no statistical differences are observed (B3/B46 p=0.061 with Mann-Whitney U test; B10/B3 p=0.132 with two sample t-test analysis; B46/B10 with two sample t-test analysis p=0.127); we have to consider that applying this ratio in an increased sample might be an useful algorithm to complete screening of CRC.

In this line, the combination of four sequences also must be considered to increase sensitivity and specificity of the test.

TABLE 7

Quantification of the 4 bacterial sequences expressed in Ct of healthy individuals (C) and colorectal cancer risk individuals (CRC + L), statistical analysis through two sample t-test and ROC analysis.

| ID | Group | Condition | B3 | B48 | B10 | B46 |
|---|---|---|---|---|---|---|
| 4 | CRC + L | 3 | 29.86 | 20.84 | 14.18 | 21.34 |
| 5 | CRC + L | 3 | 24.3 | 15.88 | 10.34 | 17.53 |
| 6 | CRC + L | 3 | 27.33 | 20.66 | 15.77 | 23.13 |
| 7 | CRC + L | 3 | 24.88 | 19.06 | 13.64 | 20.69 |
| 8 | CRC + L | 3 | 20.61 | 17.78 | 12.92 | 19.7 |
| 11 | CRC + L | 3 | 27.28 | 25.69 | 17.05 | 24.35 |
| 12 | CRC + L | 3 | 29.04 | 22.58 | 16.49 | 23.17 |
| 13 | CRC + L | 3 | 21.98 | 17.52 | 10.97 | 17.34 |
| 14 | CRC + L | 3 | 27.07 | 19.94 | 13.52 | 19.9 |
| 15 | CRC + L | 3 | 28.57 | 26.60 | 19.77 | 27.53 |
| 24 | CRC + L | 3 | 26.77 | 22.64 | 17.84 | 23.83 |
| 25 | CRC + L | 3 | 21.64 | 17.01 | 11.54 | 18.7 |
| 27 | CRC + L | 3 | 26.52 | 20.97 | 15.49 | 22.63 |
| 31 | CRC + L | 3 | 29.91 | 18.92 | 16.44 | 23.8 |
| 35 | CRC + L | 3 | 23.37 | 18.81 | 12.24 | 18.77 |
| 36 | CRC + L | 3 | 22.87 | 17.28 | 12.74 | 19.76 |
| 38 | CRC + L | 3 |  | 16.36 | 24.43 | 30.7 |
| F10 | CRC + L | 3 | 20.49 | 18.59 | 16.33 | 22.78 |
| F16 | CRC + L | 3 | 18.24 |  | 14.35 | 20.75 |
| F11 | CRC + L | 3 | 29.19 | 20.33 | 20.37 | 26.45 |
| F3 | CRC + L | 3 | 32.48 | 23.52 | 19.80 | 26.20 |
| F4 | CRC + L | 3 | 21.76 | 16.41 | 14.88 | 20.87 |
| F5 | CRC + L | 3 | 20.56 | 19.04 | 17.61 | 24.00 |
| F6 | CRC + L | 3 | 31.6 | 23.22 | 21.82 | 27.67 |
| F7 | CRC + L | 3 | 27.14 | 23.19 | 22.34 | 28.20 |
| F8 | CRC + L | 3 | 22.37 | 18.82 | 15.61 | 22.04 |
| 43 | CRC + L | 3 | 30.9 | 22.46 | 17.12 | 25.57 |
| 1 | CRC + L | 3 | 23.08 | 18.76 | 12.03 | 19.21 |
| 2 | CRC + L | 3 | 26.58 | 18.47 | 13.60 | 21.02 |
| 3 | CRC + L | 3 | 23.51 | 19.36 | 10.85 | 18.33 |
| 9 | CRC + L | 3 |  | 16.94 | 12.89 | 19.77 |
| 10 | CRC + L | 3 | 19.91 | 17.68 | 10.44 | 17.84 |
| 19 | CRC + L | 3 | 32.81 | 21.60 | 15.72 | 21.67 |
| 20 | CRC + L | 3 | 19.9 | 19.77 | 17.81 | 24.2 |
| 21 | CRC + L | 3 | 19.66 | 17.05 | 13.55 | 19.7 |
| 22 | CRC + L | 3 | 21.28 | 16.04 | 10.22 | 17.48 |
| 26 | CRC + L | 3 | 19.57 | 20.73 | 11.79 | 19.36 |
| 29 | CRC + L | 3 | 23.67 | 17.92 | 11.30 | 18.2 |
| 40 | CRC + L | 3 | 29.14 | 23.47 | 19.42 | 26.3 |
| 41 | CRC + L | 3 | 32.14 | 20.18 | 17.27 | 23.72 |
| 42 | CRC + L | 3 | 35.19 | 18.34 | 19.63 | 27.07 |
| 44 | CRC + L | 3 | 28.83 | 23.16 | 16.15 | 23.42 |
| 45 | CRC + L | 3 | 24.79 | 16.85 | 10.84 | 19.02 |
| MIL1 | CRC + L | 3 | 37.1 | 22.60 | 14.69 | 25.52 |
| MIL2 | CRC + L | 3 | 32.74 | 24.60 | 14.63 | 25.53 |
| MIL3 | CRC + L | 3 | 27.80 | 18.00 | 10.34 | 20.28 |

TABLE 7-continued

Quantification of the 4 bacterial sequences expressed in Ct of healthy individuals (C) and colorectal cancer risk individuals (CRC + L), statistical analysis through two sample t-test and ROC analysis.

| ID | Group | Condition | B3 | B48 | B10 | B46 |
|---|---|---|---|---|---|---|
| MIL4 | CRC + L | 3 | 29.09 | 20.00 | 18.17 | 29.66 |
| MIL5 | CRC + L | 3 | 33.45 | 22.60 | | 24.81 |
| MIL6 | CRC + L | 3 | 31.69 | 20.20 | 14.66 | 24.54 |
| MIL7 | CRC + L | 3 | 35.88 | 22.90 | 13.05 | 24.59 |
| MIL8 | CRC + L | 3 | 26.2 | 20.60 | 10.85 | 21.87 |
| 16 | C | 0 | 22.97 | 20.21 | 15.54 | 23.12 |
| 17 | C | 0 | 20.4 | 15.84 | 10.71 | 17.54 |
| 18 | C | 0 | 22.05 | 15.72 | 12.06 | 17.67 |
| 23 | C | 0 | 21.79 | 17.16 | 12.59 | 18.89 |
| 28 | C | 0 | 20 | 18.86 | 15.29 | 21.33 |
| 30 | C | 0 | 26.61 | 20.47 | 12.78 | 20.26 |
| 32 | C | 0 | 22.76 | 15.07 | 15.95 | 23.09 |
| 33 | C | 0 | 23.66 | 18.30 | 13.54 | 19.57 |
| 34 | C | 0 | 22.01 | 17.73 | 14.29 | 19.07 |
| 37 | C | 0 | 24.06 | 19.46 | 14.47 | 19.65 |
| F1 | C | 0 | 24.71 | 18.09 | 14.79 | 21.97 |
| F12 | C | 0 | 20.79 | 17.55 | 14.95 | 20.90 |
| F13 | C | 0 | 25.1 | 19.36 | 19.22 | 24.78 |
| F14 | C | 0 | 21.63 | 19.46 | 15.07 | 21.44 |
| F2 | C | 0 | 20.42 | 17.07 | 12.76 | 20.57 |
| F15 | C | 0 | 19.69 | 17.55 | 12.84 | 19.85 |
| F9 | C | 0 | 23.29 | 17.61 | 15.41 | 21.80 |
| 39 | C | 0 | | 18.03 | 11.95 | 18.97 |
| Mean | CRC + L | | 26.54 | 20.03 | 15.10 | 22.56 |
| | C | | 22.46 | 17.98 | 14.12 | 20.58 |
| Standard Deviation | CRC + L | | 4.86 | 2.64 | 3.48 | 3.39 |
| | C | | 1.94 | 1.51 | 1.96 | 1.93 |
| P-Value (Two sample t-test) | CRC + L vs C | | 0.0001 | 0.001 | 0.137 | 0.004 |
| | Mid-Point | | 25.65 | 19.69 | 15.58 | 23.13 |
| | AUC | | 0.71 | 0.70 | 0.580 | 0.665 |
| | Sensitivity | | 56.2 | 51 | 44.9 | 94.7 |
| | Specificity | | 88.9 | 84 | 89.5 | 23.12 |

FIG. 22 provides the graphical representation of absolute Ct values of sequences SEQ ID NO: 1, SEQ ID NO: 4, SEQ ID NO: 7 and SEQ ID NO: 10, respectively, in CRC+Lynch (L) and healthy (C) groups.

Figure 29:
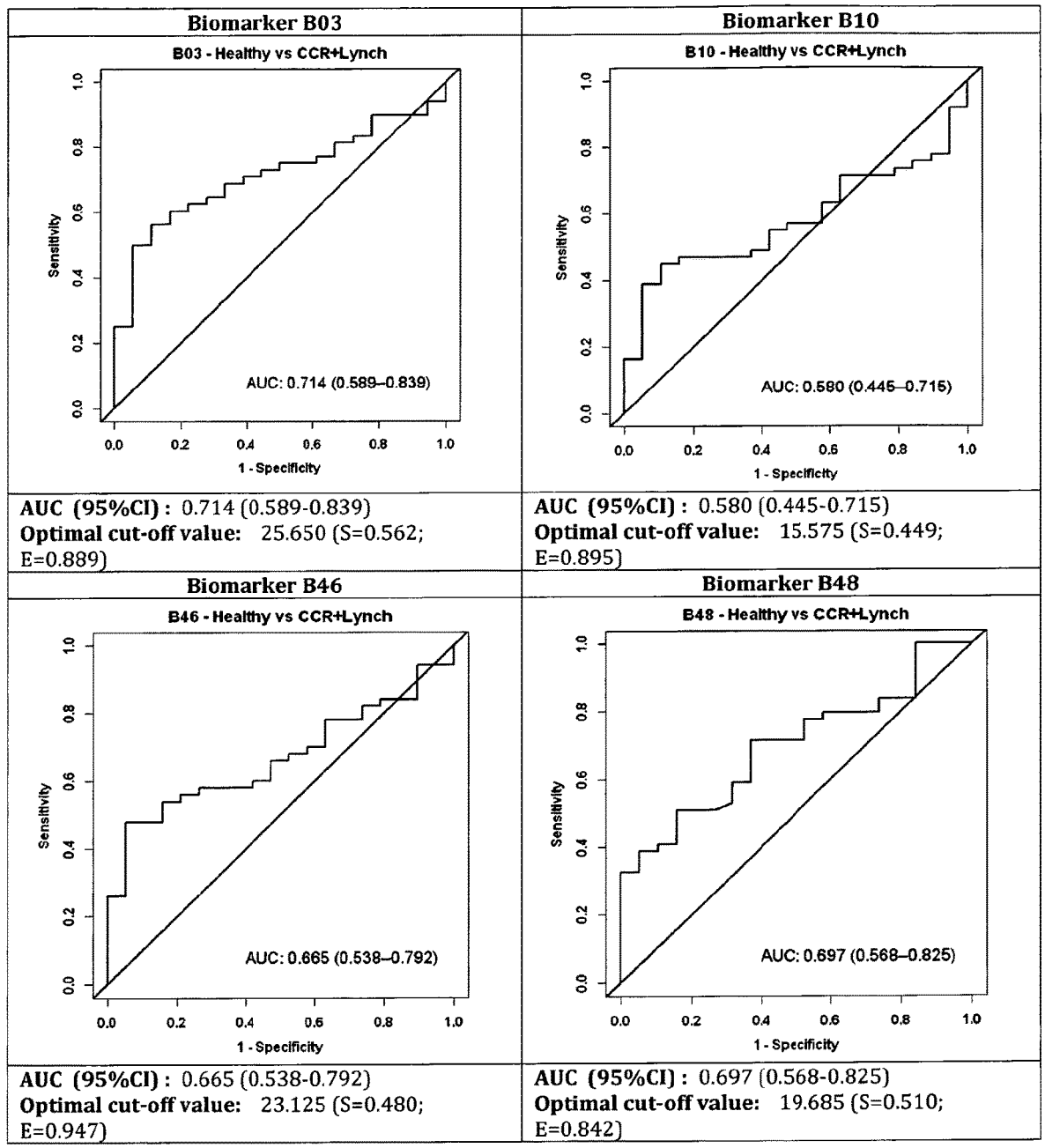
FIG. 29. ROC curves for B3, B10, B46 and B48 in healthy vs CRC+Lynch analysis.

FIG. 29 provides the ROC curves for B3, B10, B46 and B48 in healthy vs CCR+Lynch analysis.

Example 8: 16S rDNA Biomarkers Analysis CRC Vs L-High Risk Vs L-Low Risk Vs Healthy Individuals In this example, we aim to define different grades of colorectal cancer risk using quantification of bacterial sequences in Lynch syndrome carriers.

We classified Lynch syndrome carriers in High risk (L-High Risk) and Low risk (L-Low risk) colorectal cancer according his colorectal neoplasm background and the presence of adenomas in his last colonoscopy. We have 6 High risk and 18 Low risk individuals.

The quantification of the four bacterial sequences was performed and no statistically differences were observed between the different groups. Only for B3 levels, there was tendency of a Ct decreased comparing C vs L-Low risk (p=0.088, Kruskal-Wallis test) and C vs L-High risk (p=0.143, Kruskal-Wallis test).

The ratio between Ct of bacterial sequences quantification was calculated.

Kruskal-Wallis test was applied and B3/B10 and B10/B46 ratios present a significant difference between C and L-Low risk. B3/B48 ratio shows significant difference comparing C vs L-High risk. B3/B10 and B48/B10 ratios were significantly different in CRC vs L-High Risk. ROC analyses were not performed because of sample size, but considering the statistical analyses we might forecast that the best ratio might be B3/B10 because is able to distinguish L-Low risk group In this line, the combination of four sequences also must be considered to increase powerful of the test, and a multivariable logistic regression analyses must be performed but an increased sample size is required.

TABLE 8

Quantification of the 4 bacterial sequences expressed in Ct of healthy individuals (C), L-Low risk, L-High risk and CRC

| ID | Group | Condition | B3 | B48 | B10 | B46 | B3/B10 | B48/B10 | B3/B48 | B10/B46 |
|---|---|---|---|---|---|---|---|---|---|---|
| 4 | CRC | 1 | 29.86 | 20.84 | 14.18 | 21.34 | 2.11 | 1.47 | 1.43 | 0.66 |
| 5 | CRC | 1 | 24.3 | 15.88 | 10.34 | 17.53 | 2.35 | 1.54 | 1.53 | 0.59 |
| 6 | CRC | 1 | 27.33 | 20.66 | 15.77 | 23.13 | 1.73 | 1.31 | 1.32 | 0.68 |
| 7 | CRC | 1 | 24.88 | 19.06 | 13.64 | 20.69 | 1.82 | 1.40 | 1.31 | 0.66 |
| 8 | CRC | 1 | 20.61 | 17.78 | 12.92 | 19.7 | 1.60 | 1.38 | 1.16 | 0.66 |
| 11 | CRC | 1 | 27.28 | 25.69 | 17.05 | 24.35 | 1.60 | 1.51 | 1.06 | 0.70 |
| 12 | CRC | 1 | 29.04 | 22.58 | 16.49 | 23.17 | 1.76 | 1.37 | 1.29 | 0.71 |
| 13 | CRC | 1 | 21.98 | 17.52 | 10.97 | 17.34 | 2.00 | 1.60 | 1.25 | 0.63 |
| 14 | CRC | 1 | 27.07 | 19.94 | 13.52 | 19.9 | 2.00 | 1.47 | 1.36 | 0.68 |
| 15 | CRC | 1 | 28.57 | 26.60 | 19.77 | 27.53 | 1.45 | 1.35 | 1.07 | 0.72 |
| 24 | CRC | 1 | 26.77 | 22.64 | 17.84 | 23.83 | 1.50 | 1.27 | 1.18 | 0.75 |
| 25 | CRC | 1 | 21.64 | 17.01 | 11.54 | 18.7 | 1.88 | 1.47 | 1.27 | 0.62 |
| 27 | CRC | 1 | 26.52 | 20.97 | 15.49 | 22.63 | 1.71 | 1.35 | 1.26 | 0.68 |
| 31 | CRC | 1 | 29.91 | 18.92 | 16.44 | 23.8 | 1.82 | 1.15 | 1.58 | 0.69 |
| 35 | CRC | 1 | 23.37 | 18.81 | 12.24 | 18.77 | 1.91 | 1.54 | 1.24 | 0.65 |
| 36 | CRC | 1 | 22.87 | 17.28 | 12.74 | 19.76 | 1.80 | 1.36 | 1.32 | 0.64 |
| 38 | CRC | 1 | | 16.36 | 24.43 | 30.7 | | 0.67 | | 0.80 |
| F10 | CRC | 1 | 20.49 | 18.59 | 16.33 | 22.78 | 1.25 | 1.14 | 1.10 | 0.72 |
| F16 | CRC | 1 | 18.24 | | 14.35 | 20.75 | 1.27 | | | 0.69 |
| F11 | CRC | 1 | 29.19 | 20.33 | 20.37 | 26.45 | 1.43 | 1.00 | 1.44 | 0.77 |
| F3 | CRC | 1 | 32.48 | 23.52 | 19.80 | 26.20 | 1.64 | 1.19 | 1.38 | 0.76 |
| F4 | CRC | 1 | 21.76 | 16.41 | 14.88 | 20.87 | 1.46 | 1.10 | 1.33 | 0.71 |
| F5 | CRC | 1 | 20.56 | 19.04 | 17.61 | 24.00 | 1.17 | 1.08 | 1.08 | 0.73 |
| F6 | CRC | 1 | 31.6 | 23.22 | 21.82 | 27.67 | 1.45 | 1.06 | 1.36 | 0.79 |
| F7 | CRC | 1 | 27.14 | 23.19 | 22.34 | 28.20 | 1.21 | 1.04 | 1.17 | 0.79 |
| F8 | CRC | 1 | 22.37 | 18.82 | 15.61 | 22.04 | 1.43 | 1.21 | 1.19 | 0.71 |

TABLE 8-continued

Quantification of the 4 bacterial sequences expressed in Ct
of healthy individuals (C), L-Low risk, L-High risk and CRC

| ID | Group | Condition | B3 | B48 | B10 | B46 | B3/B10 | B48/B10 | B3/B48 | B10/B46 |
|---|---|---|---|---|---|---|---|---|---|---|
| 43 | CRC | 1 | 30.9 | 22.46 | 17.12 | 25.57 | 1.80 | 1.31 | 1.38 | 0.67 |
| 16 | C | 0 | 22.97 | 20.21 | 15.54 | 23.12 | 1.48 | 1.30 | 1.14 | 0.67 |
| 17 | C | 0 | 20.4 | 15.84 | 10.71 | 17.54 | 1.90 | 1.48 | 1.29 | 0.61 |
| 18 | C | 0 | 22.05 | 15.72 | 12.06 | 17.67 | 1.83 | 1.30 | 1.40 | 0.68 |
| 23 | C | 0 | 21.79 | 17.16 | 12.59 | 18.89 | 1.73 | 1.36 | 1.27 | 0.67 |
| 28 | C | 0 | 20 | 18.86 | 15.29 | 21.33 | 1.31 | 1.23 | 1.06 | 0.72 |
| 30 | C | 0 | 26.61 | 20.47 | 12.78 | 20.26 | 2.08 | 1.60 | 1.30 | 0.63 |
| 32 | C | 0 | 22.76 | 15.07 | 15.95 | 23.09 | 1.43 | 0.94 | 1.51 | 0.69 |
| 33 | C | 0 | 23.66 | 18.30 | 13.54 | 19.57 | 1.75 | 1.35 | 1.29 | 0.69 |
| 34 | C | 0 | 22.01 | 17.73 | 14.29 | 19.07 | 1.54 | 1.24 | 1.24 | 0.75 |
| 37 | C | 0 | 24.06 | 19.60 | 14.47 | 19.65 | 1.66 | 1.35 | 1.23 | 0.74 |
| F1 | C | 0 | 24.71 | 18.09 | 14.79 | 21.97 | 1.67 | 1.22 | 1.37 | 0.67 |
| F12 | C | 0 | 20.79 | 17.55 | 14.95 | 20.90 | 1.39 | 1.17 | 1.18 | 0.72 |
| F13 | C | 0 | 25.1 | 19.36 | 19.22 | 24.78 | 1.31 | 1.01 | 1.30 | 0.78 |
| F14 | C | 0 | 21.63 | 19.46 | 15.07 | 21.44 | 1.44 | 1.29 | 1.11 | 0.70 |
| F2 | C | 0 | 20.42 | 17.07 | 12.76 | 20.57 | 1.60 | 1.34 | 1.20 | 0.62 |
| F15 | C | 0 | 19.69 | 17.55 | 12.84 | 19.85 | 1.53 | 1.37 | 1.12 | 0.65 |
| F9 | C | 0 | 23.29 | 17.61 | 15.41 | 21.80 | 1.51 | 1.14 | 1.32 | 0.71 |
| 39 | C | 0 | | 18.03 | 11.95 | 18.97 | | 1.51 | | 0.63 |
| 1 | L-Low Risk | 4 | 23.08 | 18.76 | 12.03 | 19.21 | 1.92 | 1.56 | 1.23 | 0.63 |
| 3 | L-Low Risk | 4 | 23.51 | 19.36 | 10.85 | 18.33 | 2.17 | 1.78 | 1.21 | 0.59 |
| 9 | L-Low Risk | 4 | | 16.94 | 12.89 | 19.77 | | 1.31 | | 0.65 |
| 10 | L-Low Risk | 4 | 19.91 | 17.68 | 10.44 | 17.84 | 1.91 | 1.69 | 1.13 | 0.58 |
| 19 | L-Low Risk | 4 | 32.81 | 21.60 | 15.72 | 21.67 | 2.09 | 1.37 | 1.52 | 0.73 |
| 20 | L-Low Risk | 4 | 19.9 | 19.77 | 17.81 | 24.2 | 1.12 | 1.11 | 1.01 | 0.74 |
| 21 | L-Low Risk | 4 | 19.66 | 17.05 | 13.55 | 19.7 | 1.45 | 1.26 | 1.15 | 0.69 |
| 26 | L-Low Risk | 4 | 19.57 | 20.73 | 11.79 | 19.36 | 1.66 | 1.76 | 0.94 | 0.61 |
| 29 | L-Low Risk | 4 | 23.67 | 17.92 | 11.30 | 18.2 | 2.09 | 1.59 | 1.32 | 0.62 |
| 40 | L-Low Risk | 4 | 29.14 | 23.47 | 19.42 | 26.3 | 1.50 | 1.21 | 1.24 | 0.74 |
| 42 | L-Low Risk | 4 | 35.19 | 18.34 | 19.63 | 27.07 | 1.79 | 0.93 | 1.92 | 0.73 |
| 44 | L-Low Risk | 4 | 28.83 | 23.16 | 16.15 | 23.42 | 1.79 | 1.43 | 1.24 | 0.69 |
| MIL1 | L-Low Risk | 4 | 37.1 | 22.60 | 14.69 | 25.52 | 2.53 | 1.54 | 1.64 | 0.58 |
| MIL2 | L-Low Risk | 4 | 32.74 | 24.60 | 14.63 | 25.53 | 2.24 | 1.68 | 1.33 | 0.57 |
| MIL3 | L-Low Risk | 4 | 27.80 | 18.00 | 10.34 | 20.28 | 2.69 | 1.74 | 1.54 | 0.51 |
| MIL6 | L-Low Risk | 4 | 31.69 | 20.20 | 14.66 | 24.54 | 2.16 | 1.38 | 1.57 | 0.60 |
| MIL7 | L-Low Risk | 4 | 35.88 | 22.90 | 13.05 | 24.59 | 2.75 | 1.75 | 1.57 | 0.53 |
| MIL8 | L-Low Risk | 4 | 26.2 | 20.60 | 10.85 | 21.87 | 2.41 | 1.90 | 1.27 | 0.50 |
| 2 | L-High Risk | 5 | 26.58 | 18.47 | 13.60 | 21.02 | 1.95 | 1.36 | 1.44 | 0.65 |
| 22 | L-High Risk | 5 | 21.28 | 16.04 | 10.22 | 17.48 | 2.08 | 1.57 | 1.33 | 0.58 |
| 41 | L-High Risk | 5 | 32.14 | 20.18 | 17.27 | 23.72 | 1.86 | 1.17 | 1.59 | 0.73 |
| 45 | L-High Risk | 5 | 24.79 | 16.85 | 10.84 | 19.02 | 2.29 | 1.55 | 1.47 | 0.57 |
| MIL4 | L-High Risk | 5 | 29.09 | 20.00 | 18.17 | 29.66 | 1.60 | 1.10 | 1.45 | 0.61 |
| MIL5 | L-High Risk | 5 | 33.45 | 22.60 | | 24.81 | | | 1.48 | |
| Mean | | CRC | 25.64 | 20.16 | 16.13 | 22.87 | 1.66 | 1.28 | 1.28 | 0.70 |
| | | C | 22.47 | 17.98 | 14.12 | 20.58 | 1.60 | 1.29 | 1.25 | 0.68 |
| | | L-Low Risk | 27.45 | 20.20 | 13.88 | 22.08 | 2.02 | 1.50 | 1.34 | 0.63 |
| | | L-High Risk | 27.89 | 19.02 | 14.02 | 22.62 | 1.96 | 1.35 | 1.46 | 0.63 |
| Standard Deviation | | CRC | 3.97 | 2.89 | 3.58 | 3.45 | 0.29 | 0.21 | 0.14 | 0.05 |
| | | C | 1.95 | 1.51 | 1.96 | 1.93 | 0.21 | 0.16 | 0.11 | 0.05 |
| | | L-Low Risk | 6.08 | 2.40 | 2.96 | 3.09 | 0.44 | 0.27 | 0.25 | 0.08 |
| | | L-High Risk | 4.59 | 2.41 | 3.62 | 4.42 | 0.26 | 0.22 | 0.09 | 0.06 |
| P-Value | | CRC vs C | 0.32 | | | | | | | |
| Kruskal-Wallis test | | CRC vs LL | 1 | | | | 0.017 | 0.022 | | |
| | | CRC vs LH | 1 | | | | | | | |
| | | C vs LL | 0.088 | | | | 0.016 | | | 0.01 |
| | | C vs LH | 0.143 | | | | | | 0.031 | |
| | | LL vs LH | 1 | | | | | | | |

FIGS. 23 to 26 provide the graphical representation of the following absolute Ct values ratios B48/B10, B3/B10, B46/B10 and B3/B48, respectively in CRC, High Risk L, Low Risk L and C groups.

The invention claimed is:

1. A method of screening for colorectal cancer (CRC) in a human subject, the method comprising:
   i. quantifying in a feces sample from said human subject the concentration of at least one 16S rDNA bacterial sequence selected from the group consisting of SEQ ID NO: 7 and SEQ ID NO: 10;
   ii. comparing the quantified concentration of the at least one 16S rDNA bacterial sequence in the subject sample in (i) with a reference concentration in a control sample; and
   iii. diagnosing, early detecting, or determining recurrence for CRC in said human subject when there is a deviation of the value of the quantified concentration of the at least one of said sequences in the human subject sample from the values of the reference concentration in said control sample;
   wherein
   SEQ ID NO: 7 concentration is determined using primers with at least 90% sequence identity with respect to SEQ ID NO: 8 and SEQ ID NO: 9 respectively; and
   SEQ ID NO: 10 concentration is determined using primers with at least 90% sequence identity with respect to SEQ ID NO: 11 and SEQ ID NO: 12, respectively.

2. The method according to claim 1, wherein said method comprises
   quantifying the concentration of at least two of said bacterial sequences in step (i); and determining the value of at least one of the ratios of concentration of said sequences; and comparing the value of at least one of said ratios in said subject with a reference ratio in a control sample, wherein a deviation of the ratio value in said subject sample from the reference ratio in said control sample is indicative of CRC.

3. The method according to claim 1, wherein DNA is extracted from the feces sample prior to quantifying the concentration of said bacterial sequences.

4. The method according to claim 1, wherein the quantification of said bacterial sequences is performed by quantitative PCR.

5. The method according to claim 4, wherein the quantified concentrations are expressed as the cycle threshold (Ct) value.

6. The method according to claim 1, wherein
SEQ ID NO: 7 concentration is determined using primers comprising the sequences of SEQ ID NO: 8 and SEQ ID NO: 9; and
SEQ ID NO: 10 concentration is determined using primers comprising the sequences of SEQ ID NO: 11 and SEQ ID NO: 12.

7. The method according to claim 1, wherein said method comprises quantifying the concentration of SEQ ID NO: 7 and SEQ ID NO: 10, and further comprises quantifying the concentration of SEQ ID NO: 1 and SEQ ID NO: 4, wherein
SEQ ID NO: 1 concentration is determined using primers with at least 90% sequence identity with respect to SEQ ID NO: 2 and SEQ ID NO: 13, respectively; and
SEQ ID NO: 4 concentration is determined using primers with at least 90% sequence identity with respect to SEQ ID NO: 5 and SEQ ID NO: 6, respectively.

8. The method according to claim 1, wherein said method further comprises detecting and/or quantifying one or more additional molecular biomarkers which are known to be indicative of CRC.

9. The method according to claim 1, wherein said method further comprises storing the method results in a computer readable medium.

10. The method according to claim 1, wherein said method further comprises conducting an additional test selected from the group consisting of:
  i. the guaiac-based fecal occult blood test ("gFOBT");
  ii. the fecal immunochemical test ("FIT"); and
  iii. the stool DNA (sDNA) test.

11. The method of claim 1, further comprising treating the human subject diagnosed in step (iii) as having CRC.

12. The method of claim 1, further comprising conducting a colonoscopy in a human subject diagnosed in step (iii) as having CRC.

13. The method of claim 1, wherein step (i) comprises quantifying in a feces sample from said human subject the concentration of SEQ ID NO: 7 and SEQ ID NO: 10.

14. The method of claim 1, further comprising, prior to step (ii), normalizing the quantified concentration of at least one 16S rDNA bacterial sequence in (i) with one or more internal reference sequences in the human subject sample, and further comprising:
  ii. comparing the normalized concentration of at least one 16S rDNA bacterial sequence in the subject sample with a reference concentration in a control sample; and
  iii. diagnosing, early detecting, or determining recurrence for CRC in said human subject when there is a deviation of the value of the normalized concentration of at least one of said sequences in the human subject sample from the values of the reference concentration in said control sample.

15. A method of screening for CRC in a human subject, the method comprising:
  i. determining, by quantitative PCR in a feces sample from said human subject, the concentration of at least one 16S rDNA bacterial sequence selected from the group consisting of SEQ ID NO: 7 and SEQ ID NO: 10, wherein said concentration is expressed as Ct value;
  ii. comparing the Ct value of the at least one 16S rDNA bacterial sequence in the subject sample in (i) with a cut-off Ct value; and
  iii. diagnosing, early detecting, or determining recurrence for CRC in said human subject, when there is an increase in the Ct value of the at least one of the sequences in step (i) in the subject sample with respect to said cut-off Ct value;
wherein
SEQ ID NO: 7 concentration is determined using primers with at least 90% sequence identity with respect to SEQ ID NO: 8 and SEQ ID NO: 9 respectively; and
SEQ ID NO: 10 concentration is determined using primers with at least 90% sequence identity with respect to SEQ ID NO: 11 and SEQ ID NO: 12, respectively.

16. The method of claim 15, further comprising treating the human subject diagnosed in step (iii) as having CRC.

17. The method of claim 15, further comprising conducting a colonoscopy in a human subject diagnosed in step (iii) as having CRC.

18. The method of claim 15, wherein step (i) comprises determining, by quantitative PCR in a feces sample from said human subject, the concentration of SEQ ID NO: 7 and SEQ ID NO: 10.

19. The method of claim 15, further comprising, prior to step (ii), normalizing the determined Ct value of at least one 16S rDNA bacterial sequence in (i) with one or more internal reference sequences in the human subject sample, and further comprising:
  ii. comparing the normalized Ct value with a cut-off Ct value; and
  iii. diagnosing, early detecting, or determining recurrence for CRC in said human subject, when there is an increase in the normalized Ct value of at least one of the sequences in step (i) in the subject sample with respect to said cut-off Ct value.

20. The method of claim 15, wherein said method comprises quantifying the concentrations of SEQ ID NO: 7 and SEQ ID NO: 10, and further comprises quantifying the concentrations of SEQ ID NO: 1 and SEQ ID NO: 4, wherein
SEQ ID NO: 1 concentration is determined using primers with at least 90% sequence identity with respect to SEQ ID NO: 2 and SEQ ID NO: 13, respectively; and
SEQ ID NO: 4 concentration is determined using primers with at least 90% sequence identity with respect to SEQ ID NO: 5 and SEQ ID NO: 6, respectively.

21. A method of screening for polyps in a human subject, the method comprising:
  i. quantifying the concentration of the 16S rDNA bacterial sequence of SEQ ID NO: 7 in a feces sample from said subject;
  ii. comparing the quantified concentration of the 16S rDNA bacterial sequence of SEQ ID NO: 7 in said subject in (i) with a reference concentration in a control sample; and iii. diagnosing, early detecting, or determining recurrence of polyps in said human subject, when there is a deviation in concentration of the 16S rDNA bacterial sequence of SEQ ID NO: 7 in the subject sample compared to the reference concentration in said control sample;

wherein

SEQ ID NO: 7 concentration is determined using primers with at least 90% sequence identity with respect to SEQ ID NO: 8 and SEQ ID NO: 9, respectively.

22. The method of claim 21, further comprising conducting a colonoscopy in a human subject identified in step (iii) as having polyps.

23. The method of claim 21, further comprising, prior to step (ii), normalizing the quantified concentration of at least one 16S rDNA bacterial sequence in (i) with one or more internal reference sequences in the subject sample, and further comprising:
   ii. comparing the normalized concentration with a reference concentration in a control sample; and
   iii. diagnosing, early detecting, or determining recurrence of polyps in said human subject, when there is a deviation in the normalized concentration of the at least one 16S rDNA bacterial sequence in the subject sample compared to the reference concentration in said control sample.

24. The method of claim 21, wherein step (i) comprises quantifying the concentrations of the 16S rDNA bacterial sequences of SEQ ID NO: 7 and SEQ ID NO: 4 in a feces sample from said subject; and wherein said method further comprises:
   ii. comparing the quantified concentrations of the 16S rDNA bacterial sequences of SEQ ID NO: 7 and SEQ ID NO: 4 in said subject in (i) with a corresponding reference concentration in a control sample; and
   iii. diagnosing, early detecting, or determining recurrence of polyps in said human subject, when there is a deviation in concentration of the 16S rDNA bacterial sequences of SEQ ID NO: 7 and SEQ ID NO: 4 in the subject sample compared to the corresponding reference concentration in said control sample.

25. The method of claim 24, wherein SEQ ID NO: 4 concentration is determined using primers with at least 90% sequence identity with respect to SEQ ID NO: 5 and SEQ ID NO: 6, respectively.

26. A method of screening for polyps in a human subject, the method comprising:
   i. determining, by quantitative PCR in a feces sample from said subject, the concentration of the 16S rDNA bacterial sequence of SEQ ID NO: 7, wherein said concentration is expressed as Ct value;
   ii. comparing the Ct value of the 16S rDNA bacterial sequence of SEQ ID NO: 7 in the subject sample in (i) with a cut-off Ct value; and
   iii. diagnosing, early detecting, or determining recurrence for polyps in said human subject, when there is an increase in the Ct value of the sequence of SEQ ID NO: 7 in step (i) in the subject sample with respect to said cut-off Ct value;

wherein

SEQ ID NO: 7 concentration is determined using primers with at least 90% sequence identity with respect to SEQ ID NO: 8 and SEQ ID NO: 9, respectively.

27. The method of claim 26, further comprising conducting a colonoscopy in a human subject identified in step (iii) as having polyps.

28. The method of claim 26, further comprising, prior to step (ii), normalizing the determined Ct value of at least one 16S rDNA bacterial sequence in (i) with one or more internal reference sequences in the subject sample; and further comprising:
   ii. comparing the normalized Ct value with a cut-off Ct value; and
   iii. diagnosing, early detecting, or determining recurrence for polyps in said human subject, when there is an increase in the normalized Ct value of at least one of the sequences in step (i) in the subject sample with respect to said cut-off Ct value.

29. The method of claim 26, wherein step (i) comprises determining, by quantitative PCR in a feces sample from said subject, the concentration of the 16S rDNA bacterial sequences of SEQ ID NO: 7 and SEQ ID NO: 4, wherein said concentration is expressed as Ct value;
   ii. comparing the Ct value of the 16S rDNA bacterial sequences of SEQ ID NO: 7 and SEQ ID NO: 4 in the subject sample in (i) with a corresponding cut-off Ct value; and
   iii. diagnosing, early detecting, or determining recurrence for polyps in said human subject, when there is an increase in the Ct value of the sequences of SEQ ID NO: 7 and SEQ ID NO: 4 in step (i) in the subject sample with respect to the corresponding cut-off Ct value.

30. The method of claim 29, wherein SEQ ID NO: 4 concentration is determined using primers with at least 90% sequence identity with respect to SEQ ID NO: 5 and SEQ ID NO: 6, respectively.

* * * * *

SEQUENCE LISTING

<160> NUMBER OF SEQ ID NOS: 13

<210> SEQ ID NO 1
<211> LENGTH: 489
<212> TYPE: DNA

<213> ORGANISM: Artificial Sequence
<220> FEATURE:
<223> OTHER INFORMATION: B3 16S ribosomal DNA sequence, accession number
      GQ411111.1

<400> SEQUENCE: 1

```
acggaggcct tcgggtcgta accgctttca gcagggaaga gtcaagactg tacctgcaga      60
agaagccccg gctaactacg tgccagcagc cgcggtaata cgtaggggc gagcgttatc      120
cggattcatt gggcgtaaag cgcgcgtagg cggcccggca ggccggggt cgaagcgggg      180
ggctcaaccc cccgaagccc cggaacctc cgcggcttgg gtccggtagg ggagggtgga      240
acacccggtg tagcggtgga atgcgcagat atcgggtgga acaccggtgg cgaaggcggc      300
cctctgggcc gagaccgacg ctgaggcgcg aaagctgggg gagcgaacag gattagatac      360
cctggtagtc ccagccgtaa acgatggacg ctaggtgtgg ggggacgatc cccccgtgcc      420
gcagccaacg cattaagcgt cccgcctggg gagtacggcc gcaaggctaa aactcaaagg      480
aattgacgg                                                              489
```

<210> SEQ ID NO 2
<211> LENGTH: 19
<212> TYPE: DNA
<213> ORGANISM: Artificial Sequence
<220> FEATURE:
<223> OTHER INFORMATION: B3 16S ribosomal DNA sequence forward primer

<400> SEQUENCE: 2

```
ggaggccttc gggtcgtaa                                                   19
```

<210> SEQ ID NO 3
<211> LENGTH: 18
<212> TYPE: DNA
<213> ORGANISM: Artificial Sequence
<220> FEATURE:
<223> OTHER INFORMATION: B3 16S ribosomal DNA sequence reverse primer

<400> SEQUENCE: 3

```
ccgaagcccc cggaacct                                                    18
```

<210> SEQ ID NO 4
<211> LENGTH: 485
<212> TYPE: DNA
<213> ORGANISM: Artificial Sequence
<220> FEATURE:
<223> OTHER INFORMATION: B10 16S ribosomal DNA sequence, accession
      number GQ411118.1

<400> SEQUENCE: 4

```
cttcggattg taaactcctg ttgttgagga gataatgacg gtactcaaca aggtaagtga      60
cggctaacta cgtgccagca gccgcggtaa aacgtaggtc acaagcgttg tccggaatta     120
ctgggtgtaa agggagcgca ggcgggaaga caagttggaa gtgaaatcca tgggctcaac     180
ccatgaactg ctttcaaaac tgttttttctt gagtagtgca caggtaggcg gaattcccgg     240
tgtagcggtg gaatgcgtag atatcgggag gaacaccagt ggcgaaggcg gcctactggg     300
caccaactga cgctgaggct cgaaagtgtg ggtagcaaac aggattagat accctggtag     360
tccacactgt aaacgatgat tactaggtgt tggaggattg acccccttcag tgccgcagtt     420
aacacaataa gtaatccacc tggggagtac gaccgcaagg ttgaaactca aggaattga     480
cggac                                                                  485
```

<210> SEQ ID NO 5
<211> LENGTH: 19
<212> TYPE: DNA
<213> ORGANISM: Artificial Sequence
<220> FEATURE:
<223> OTHER INFORMATION: B10 16S ribosomal DNA sequence forward primer

<400> SEQUENCE: 5
caacaaggta agtgacggc                                                    19

<210> SEQ ID NO 6
<211> LENGTH: 20
<212> TYPE: DNA
<213> ORGANISM: Artificial Sequence
<220> FEATURE:
<223> OTHER INFORMATION: B10 16S rDNA sequence reverse primer

<400> SEQUENCE: 6
cgcctacctg tgcactactc                                                   20

<210> SEQ ID NO 7
<211> LENGTH: 474
<212> TYPE: DNA
<213> ORGANISM: Artificial Sequence
<220> FEATURE:
<223> OTHER INFORMATION: B46 16S ribosomal DNA sequence, accession
      number GQ411150.1

<400> SEQUENCE: 7
gtaacatttc tgtaacaaga catacagcag tttctcagag ttcccaaact caaaggaatt        60
gacggaagcc gcggttccac gtaagtcaca agcgttgtcc ggaattactg ggtgtaaagg      120
gagcgcaggc gggaagacaa gttggaagtg aaatccatgg gctcaaccca taaactgctt     180
tcctaactgt ttttcttgag tagtgcacag gtaggcggaa ttcccggtgt agcggtggaa      240
tgcctagata tcgggaggaa caccattggc gaaggcggcc tactggactg caactgacgc     300
tgaggctcga aagtgtgggt agcaaacagg attagatacc ctggtagtcc actccgtaaa    360
ccatgattac tacgtgttgg aggattgacc ccttctgtgc cgcagataac acaataagta    420
atccacctgg ggagtacgac cgcccggttg agactcacag gaattgacgg actc          474

<210> SEQ ID NO 8
<211> LENGTH: 19
<212> TYPE: DNA
<213> ORGANISM: Artificial Sequence
<220> FEATURE:
<223> OTHER INFORMATION: B46 16S ribosomal DNA sequence forward primer

<400> SEQUENCE: 8
tccacgtaag tcacaagcg                                                    19

<210> SEQ ID NO 9
<211> LENGTH: 20
<212> TYPE: DNA
<213> ORGANISM: Artificial Sequence
<220> FEATURE:
<223> OTHER INFORMATION: B46 16S ribosomal DNA sequence reverse primer

<400> SEQUENCE: 9
cgcctacctg tgcactactc                                                   20

<210> SEQ ID NO 10
<211> LENGTH: 566
<212> TYPE: DNA
<213> ORGANISM: Artificial Sequence

```
<220> FEATURE:
<223> OTHER INFORMATION: B48 16S ribosomal DNA sequence, accession
      number GQ411152.1

<400> SEQUENCE: 10
tctcttacgg ggagcagcag tggggaatat tgcacaatgg gggaaaccct gatgcagcga     60
cgccgcgtga gcgatgaagt atttcggtat gtaaagctct atcagcaggg aagaaaatga    120
cggtacctga ctaagaagcc ccggctaaat acgtgccagc agccgcggta atacgtatgg    180
tgcaagcgtt atccggattt actgggtgta aagggagcgt agacggagtg gcaagtctga    240
tgtgaaaacc cggggctcaa ccccgggact gcattggaaa ctgtgcatct agagtgtcgg    300
agaggtaagc ggaattccta gtgtagcggt gaaatgcgta gatattagga ggaacaccag    360
tggcgaaggc ggcttactgg acgataactg acgctgaggc tcgaaagcgt ggggagcaaa    420
caggattaga taccctggta gtccacgccg taaacgatga ctactaggtg tcggggagca    480
cagctcttcg gtgccgcagc aaacgcaata agtattccac ctggggagta cgttcgcaag    540
aatgaaactc acagaatttg acggag                                         566

<210> SEQ ID NO 11
<211> LENGTH: 18
<212> TYPE: DNA
<213> ORGANISM: Artificial Sequence
<220> FEATURE:
<223> OTHER INFORMATION: B48 16S ribosomal DNA sequence forward primer

<400> SEQUENCE: 11
gtacggggag cagcagtg                                                   18

<210> SEQ ID NO 12
<211> LENGTH: 23
<212> TYPE: DNA
<213> ORGANISM: Artificial Sequence
<220> FEATURE:
<223> OTHER INFORMATION: B48 16S ribosomal DNA sequence reverse primer

<400> SEQUENCE: 12
gacactctag atgcacagtt tcc                                             23

<210> SEQ ID NO 13
<211> LENGTH: 18
<212> TYPE: DNA
<213> ORGANISM: Artificial Sequence
<220> FEATURE:
<223> OTHER INFORMATION: B3 16S ribosomal DNA sequence reverse primer

<400> SEQUENCE: 13
aggttccggg ggcttcgg                                                   18
```